US010501474B2

(12) United States Patent
Sampson et al.

(10) Patent No.: US 10,501,474 B2
(45) Date of Patent: Dec. 10, 2019

(54) HPK1 INHIBITORS AND METHODS OF USING SAME

(71) Applicant: University Health Network, Toronto (CA)

(72) Inventors: Peter Brent Sampson, Oakville (CA); Narendra Kumar B. Patel, Brampton (CA); Heinz W. Pauls, Oakville (CA); Sze-Wan Li, Toronto (CA); Grace Ng, Markham (CA); Radoslaw Laufer, Oakville (CA); Yong Liu, Oakville (CA); Yunhui Lang, Markham (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 15/738,286

(22) PCT Filed: Jun. 23, 2016

(86) PCT No.: PCT/CA2016/050734
§ 371 (c)(1),
(2) Date: Dec. 20, 2017

(87) PCT Pub. No.: WO2016/205942
PCT Pub. Date: Dec. 29, 2016

(65) Prior Publication Data

US 2018/0179221 A1 Jun. 28, 2018

Related U.S. Application Data

(60) Provisional application No. 62/184,348, filed on Jun. 25, 2015.

(51) Int. Cl.

| | |
|---|---|
| ***C07D 495/04*** | (2006.01) |
| ***A61K 39/395*** | (2006.01) |
| ***A61K 31/496*** | (2006.01) |
| ***A61K 31/551*** | (2006.01) |
| ***C07K 16/28*** | (2006.01) |
| ***A61P 35/00*** | (2006.01) |
| ***A61K 31/5377*** | (2006.01) |
| ***A61K 45/06*** | (2006.01) |
| ***A61K 31/4355*** | (2006.01) |
| ***A61K 31/5355*** | (2006.01) |
| *A61K 39/00* | (2006.01) |

(52) U.S. Cl.
CPC ........ *C07D 495/04* (2013.01); *A61K 31/4355* (2013.01); *A61K 31/496* (2013.01); *A61K 31/5355* (2013.01); *A61K 31/5377* (2013.01); *A61K 31/551* (2013.01); *A61K 39/395* (2013.01); *A61K 45/06* (2013.01); *A61P 35/00* (2018.01); *C07K 16/2818* (2013.01); *A61K 2039/505* (2013.01)

(58) Field of Classification Search
CPC .................................................... C07D 495/04
USPC ..................................... 544/362; 514/253.04
See application file for complete search history.

(56) References Cited

U.S. PATENT DOCUMENTS

| | | | |
|---|---|---|---|
| 7,138,409 | B2 | 11/2006 | Renhowe et al. |
| 8,501,750 | B2 | 8/2013 | Kuroita et al. |
| 2004/0034054 | A1 | 2/2004 | Wilson |
| 2005/0038068 | A1 | 2/2005 | Iyengar et al. |
| 2012/0202785 | A1 | 8/2012 | Heald et al. |

FOREIGN PATENT DOCUMENTS

| | | | |
|---|---|---|---|
| WO | 2002/018383 | A2 | 3/2002 |
| WO | 2004/014375 | A2 | 2/2004 |
| WO | 2009/124636 | A1 | 10/2009 |

(Continued)

OTHER PUBLICATIONS

Frazier et al., Design and structure-activity relationship of heterocyclic analogs of 4-amino-3-benzimidazol-2-ylhydroquinolin-2-ones as inhibitors of receptor tyrosine kinases. Bioorg Med Chem Lett. Apr. 15, 2006;16(8)2247-51.

(Continued)

*Primary Examiner* — Patricia L Morris
(74) *Attorney, Agent, or Firm* — McCarter & English, LLP; Steven G. Davis; Wei Song

(57) ABSTRACT

Thienopyridinone compounds of Formula (I) and pharmaceutically acceptable salts thereof are described. In these compounds, one of $X_1$; $X_2$, and $X_3$ is S and the other two are each independently CR, wherein R and all other variables are as defined herein. The compounds are shown to inhibit HPK1 kinase activity and to have in vivo antitumor activity. The compounds can be effectively combined with pharmaceutically acceptable carriers and also with other immunomodulatory approaches, such as checkpoint inhibition or inhibitors of tryptophan oxidation. Formula (I).

Formula (I)

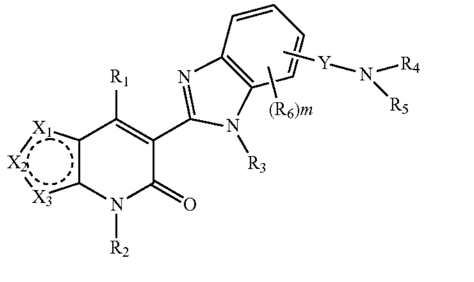

2 Claims, 3 Drawing Sheets

(56) References Cited

FOREIGN PATENT DOCUMENTS

WO 2009/135580 A1 11/2009

OTHER PUBLICATIONS

Song et al., Design, synthesis and biological evaluation of thienopyridinones as Chk1 inhibitors. Bioorg Med Chem. Sep. 1, 2014;22(17):4882-92.

International Search Report and Written Opinion for Application No. PCT/CA2016/050734, dated Sep. 8, 2016, 13 pages.

HPK1 INHIBITORS AND METHODS OF USING SAME

RELATED APPLICATIONS

This application is a U.S. national stage application filed under 35 U.S.C. § 371(c), of International Application No. PCT/CA2016/050734, filed on Jun. 23, 2016, which claims the benefit of U.S. Provisional Application No. 62/184,348, filed on Jun. 25, 2015. The entire teachings of each of the aforementioned applications are incorporated herein by reference.

BACKGROUND

Hematopoietic progenitor kinase 1 (HPK1) is a hematopoietic cell-restricted Ste20 serine/threonine kinase. HPK1 kinase activity can be induced by activation signals generated by various different cell surface receptors found in hematopoietic cells upon ligand engagement. Ligand engagement or antibody-mediated crosslinking of T cell receptors (TCR), B cell antigen receptor (BCR) (Liou et al., 2000, *Immunity* 12:399), transforming growth factor β receptor (TGF-βR) (Wang et al., 1997. *J. Biol. Chem.* 272:22771; Zhou et al., 1999, *J. Biol. Chem.* 274:13133), erythropoietin receptor (EPOR) (Nagata et al., 1999, *Blood* 93:3347), and Fas (Chen et al., 1999, *Oncogene* 18:7370) can induce HPK1 kinase activity. Each receptor utilizes unique, but sometimes overlapping, signaling mechanisms to activate HPK1. HPK1 acts as a down-modulator of T and B cell functions through the AP-1, NFKB, Erk2, and Fos pathways; for example, HPK1 has been implicated as a negative regulator of signal transduction in T-cells through phosphorylation and activation of the T-cell receptor adaptor protein SLP-76 (Di Bartolo et al., 2007, *Exp. Med.* 204:681), which leads to subsequent downregulation of the AP-1 and Erk2 pathways. In B-cells, HPK1 downregulates B-cell receptor (BCR) signaling through phosphorylation of the SLP-76 paralog BLINK (Wang et al., 2012, *J. Biol. Chem.* 287:11037).

Thus, HPK1 is now viewed as a possible target for therapeutic intervention. For example, it has been reported that HPK1 can be a novel target for cancer immunotherapy (Sawasdikosol et al., *Immunol Res.* 2012 December; 54(1-3):262-5). Specifically, targeted disruption of HPK1 alleles confers T cells with an elevated Th1 cytokine production in response to TCR engagement. HPK1 (−/−) T cells proliferate more rapidly than the haplotype-matched wild-type counterpart and are resistant to prostaglandin E2 (PGE(2))-mediated suppression. Most strikingly, mice that received adoptive transfer of HPK1 (−/−) T cells became resistant to lung tumor growth. Also, the loss of HPK1 from dendritic cells (DCs) endows them with superior antigen presentation ability, enabling HPK1 (−/−) DCs to elicit a more potent anti-tumor immune response when used as cancer vaccine.

When evaluating if a small-molecule inhibitor of HPK1 would capture the phenotype of mice with targeted disruption of the gene, it is important to consider the non-catalytic roles of the protein. In particular, while full-length HPK1 can promote TCR-mediated activation of the nuclear factor kappa-light-chain-enhancer of activated B cells (NF-κB) pathway, the catalytically inactive cleavage product HPK1-C can suppress NF-κB activation upon TCR restimulation, leading to activation-induced cell death (AICD) (Brenner et al., *EMBO J.* 2005, 24:4279). Taking together the catalytic and non-catalytic roles of HPK1, it is possible that blocking the HPK1 kinase activity with a small-molecule inhibitor may promote activation of B- and T-cells, leading to superior anti-tumor immunity, while also facilitating AICD, helping to maintain peripheral immune tolerance. The exact effects of an HPK1 inhibitor would be borne out by testing in mouse models of cancer, such as syngeneic tumor xenografts. Given that HPK1 is not expressed in any major organs, outside the hematopoietic system, it is less likely that an inhibitor of HPK1 kinase activity would cause any serious side effects.

In view of the above, there is a need in the art for novel compounds that can inhibit HPK1.

SUMMARY OF THE INVENTION

Applicant has now discovered that certain thienopyridinone compounds are HPK1 inhibitors (see Example B). They also have inhibitory activities against FLT3 and LCK (see Example C). Additionally, it has been demonstrated that certain thienopyridinone compounds as HPK1 inhibitors alone, and in combination with anti-PD-1 antibodies are effective in pre-clinical models with certain cancer cell types (see Example E). The particular combination therapies disclosed herein demonstrate surprising biological activity with significant anticancer effects. Specifically, with the combination of HPK1 inhibitors and anti-PD-1 antibodies, significant responses following PD-1/PD-L1 blockade have now been demonstrated in CT26.WT colon carcinoma. Based on these discoveries, thienopyridinone compounds, pharmaceutical compositions thereof, and methods of using the same are disclosed herein.

One embodiment of the invention is a compound represented by Structural Formula (I).

(I)

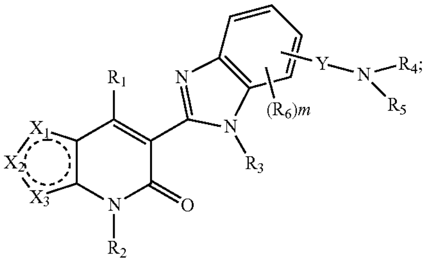

or a pharmaceutically acceptable salt thereof. Values for each of the variables are provided below.

Another embodiment of the invention is a pharmaceutical composition comprising a pharmaceutically acceptable carrier or diluent and a compound represented by Structural Formula (I) described above or a pharmaceutically acceptable salt thereof.

Another embodiment of the invention is a method of treating a subject with a disease which can be regulated by HPK1 comprising administering to the subject an effective amount of a compound of Structural Formula (I) or a pharmaceutically acceptable salt thereof.

Another embodiment of the invention is a method of inhibiting HPK1 activity in a subject in need of inhibition of HPK1 activity, comprising administering to the subject an effective amount of a compound represented by Structural Formula (I) or a pharmaceutically acceptable salt thereof.

Another embodiment of the invention is a compound represented by Structural Formula (I) or a pharmaceutically acceptable salt thereof for use in therapy. In some embodiments, the therapy is for treating a subject with cancer.

Alternatively, the therapy is for inhibiting HPK1 activity in a subject in need of inhibition of HPK1 activity.

Another embodiment of the invention is the use of a compound represented by Structural Formula (I) or a pharmaceutically acceptable salt thereof for the manufacture of a medicament for treating a subject with cancer.

Another embodiment of the invention the use of a compound represented by Structural Formulas (I) or a pharmaceutically acceptable salt thereof for the manufacture of a medicament for inhibiting HPK1 activity in a subject in need of inhibition of HPK1 activity.

The present invention is also directed to a method of treating a subject with cancer, comprising administering to the subject an effective amount of a HPK1 inhibitor (e.g., a compound represented by Structural Formula (I)), or a pharmaceutically acceptable salt thereof, and an effective second anti-cancer treatment (e.g., a chemotherapeutic agent, a targeted therapeutic agent, radiation or surgery). In one example, the second anti-cancer treatment is a PD-1 inhibitor.

The present invention is also directed to a method of treating a subject with cancer, comprising administering to the subject an effective amount of a HPK1 inhibitor (e.g., a compound represented by Structural Formula (I)), or a pharmaceutically acceptable salt thereof, and an effective amount of an immunomodulatory agent such as a checkpoint inhibitor (e.g., anti-PD-1 antibody, anti-CTLA4 antibody or anti-PD-L1 antibody) or an inhibitor of tryptophan oxidation (e.g. IDO1, IDO2 or TDO2 inhibitor). In one example, the immunomodulatory agent is anti-PD-1 antibody.

In an embodiment, the present invention further provides the use of a HPK1 inhibitor (e.g., a compound represented by Structural Formula (I), or a pharmaceutically acceptable salt thereof), for the manufacture of a medicament for the treatment of a subject with cancer, in combination with a PD-1 inhibitor such as nivolumab, pembrolizumab, pidilizumab, BMS936559, MPDL3280A, MSB0010718C or MEDI4736. Preferably, the PD-1 inhibitor is nivolumab. Alternatively, the PD-1 inhibitor is pembrolizumab. In one embodiment, the PD-1 inhibitor is anti-PD1 antibody.

In one alternative, the HPK1 inhibitor is administered with an effective amount of one or more other anti-cancer therapies, and preferably in combination with PD-1 inhibitor.

DETAILED DESCRIPTION OF THE INVENTION

Figure 1:
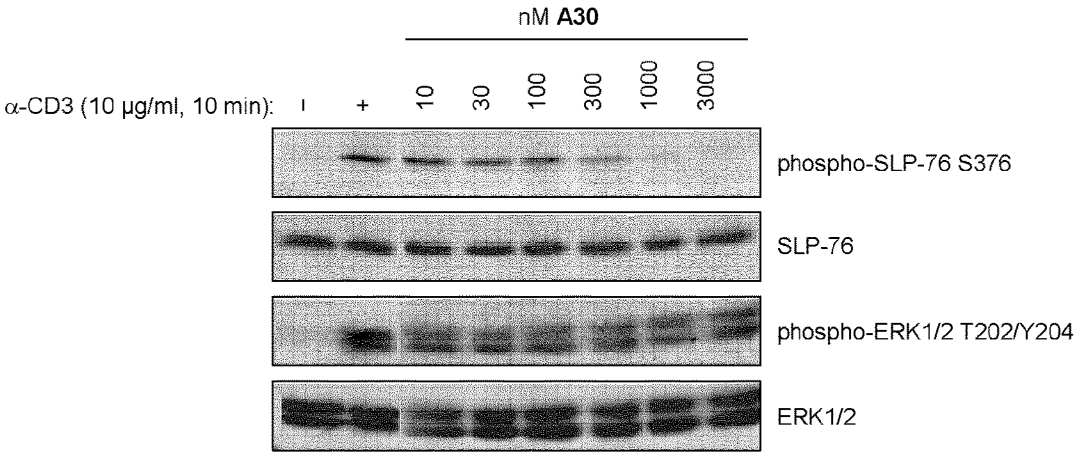
FIG. 1 shows the inhibitory effect of compound example A30 against SLP-76 serine 376 phosphorylation in α-CD3 stimulated Jurkat E6.1 cells.

In a first embodiment, the invention is directed to a compound represented by Formula (I):

(I)

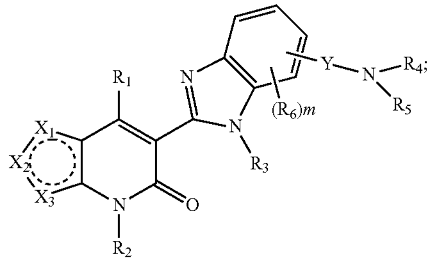

or a pharmaceutically acceptable salt thereof, wherein:

one of $X_1$, $X_2$, and $X_3$ is S, the other two are each independently CR, wherein R is —H, —F, —Cl, —Br, —CN, —OH, optionally substituted ($C_1$-$C_6$)alkyl, optionally substituted ($C_1$-$C_6$)alkoxy, optionally substituted —$(CH_2)_n$($C_3$-$C_{10}$)cycloalkyl, optionally substituted —$(CH_2)_n$-3-7 membered monocyclic heterocyclyl, optionally substituted —$(CH_2)_n$phenyl, optionally substituted —$(CH_2)_n$-5-7 membered monocyclic heteroaryl, optionally substituted —$(CH_2)_n$-bridged ($C_6$-$C_{12}$)cycloalkyl, optionally substituted —$(CH_2)_n$-6-12 membered bridged heterocyclyl, optionally substituted —$(CH_2)_n$-7-12 membered bicyclic heteroaryl, or optionally substituted —$(CH_2)_n$-7-12 membered bicyclic heteroaryl;

Y is a bond, —$CH_2$—, —C(═O)—;

$R_1$ is $NR^aR^b$ or —$OR^{a1}$;

$R^a$ for each occurrence is independently —H, optionally substituted ($C_1$-$C_6$)alkyl, optionally substituted —$(CH_2)_n$($C_3$-$C_{10}$)cycloalkyl, optionally substituted —$(CH_2)_n$-3-10 membered heterocyclyl, optionally substituted —$(CH_2)_n$($C_6$-$C_{10}$)aryl, optionally substituted —$(CH_2)_n$-5-10 membered heteroaryl, optionally substituted —$(CH_2)_n$-bridged ($C_6$-$C_{12}$)cycloalkyl, or optionally substituted —$(CH_2)_n$-6-12 membered bridged heterocyclyl;

$R^b$ for each occurrence is independently —H or —($C_1$-$C_6$)alkyl; or, $R^a$ and $R^b$, together with the nitrogen to which they are attached, form optionally substituted —($C_3$-$C_{10}$)heterocyclyl;

$R^{a1}$ for each occurrence is independently —H, optionally substituted ($C_1$-$C_6$)alkyl, optionally substituted ($C_3$-$C_{10}$)cycloalkyl, optionally substituted 3-10 membered heterocyclyl, optionally substituted ($C_6$-$C_{10}$)aryl, or optionally substituted 3-10 membered heteroaryl; or $R_2$ and $R_3$ are each independently —H or —($C_1$-$C_6$)alkyl;

$R_4$ and $R_5$ are each independently —H, optionally substituted ($C_1$-$C_6$)alkyl, optionally substituted ($C_3$-$C_{10}$)cycloalkyl, optionally substituted 3-10 membered heterocyclyl, optionally substituted ($C_6$-$C_{10}$)aryl, optionally substituted 5-10 membered heteroaryl, optionally substituted bridged ($C_6$-$C_{12}$)cycloalkyl, or optionally substituted 6-12 membered bridged heterocyclyl; or $R_4$ and $R_5$, together with the nitrogen to which they are attached, form optionally substituted 4-10 membered heterocyclyl, optionally substituted 5-10 membered heteroaryl, or optionally substituted 6-12 membered bridged heterocyclyl;

$R_6$ for each occurrence is independently —F, —Cl, —Br, —CN, —$NH_2$, —OH, —($C_1$-$C_6$)alkyl, —($C_1$-$C_6$)haloalkyl, —($C_2$-$C_6$)alkenyl, —($C_2$-$C_6$)alkynyl, ($C_3$-$C_6$)cycloalkyl, —($C_1$-$C_6$)alkoxy, —($C_1$-$C_6$)haloalkoxy, —($C_1$-$C_6$)alkylene-OH, or —($C_1$-$C_6$)alkylene-$NH_2$;

m is 0, 1, 2, or 3; and n is 0, 1, or 2.

In a second embodiment, the invention provides a compound represented by structural formula (I-A)-(I-C), (II-A)-(II-C), or (III-A)-(III-C):

(I-A)

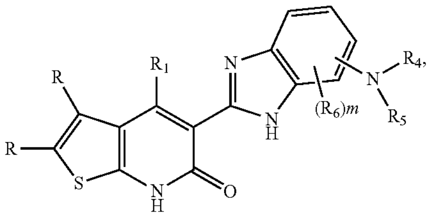

(I-B)

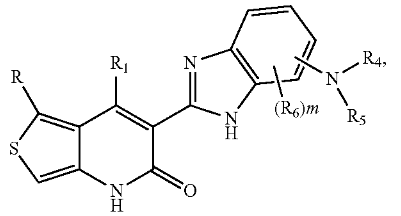

(I-C)

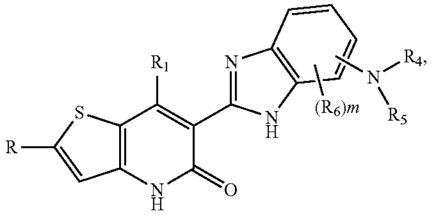

(II-A)

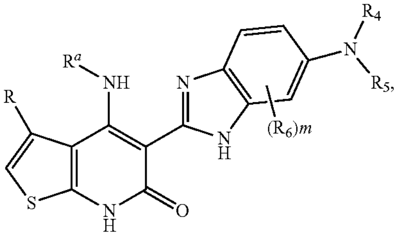

(II-B)

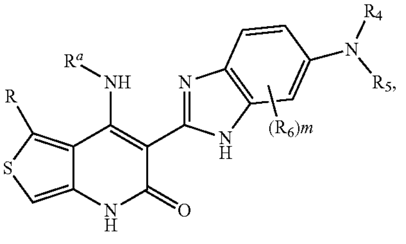

(II-C)

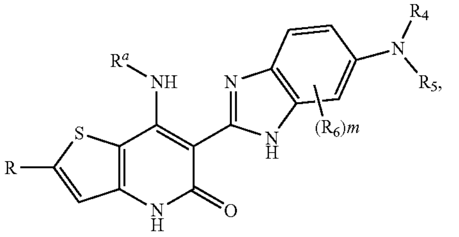

-continued (III-A)

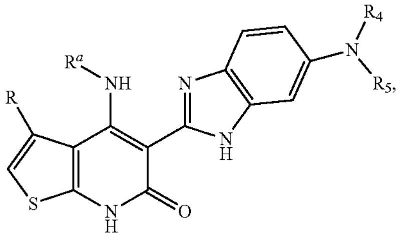

(III-B)

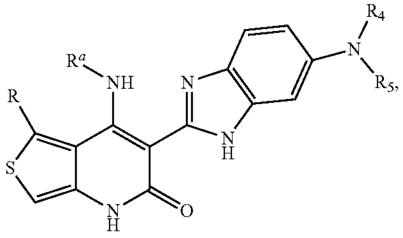

or (III-C)

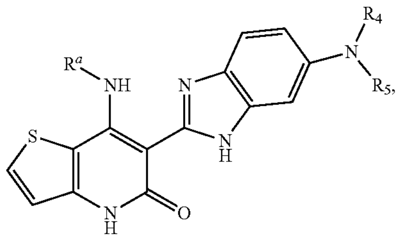

or a pharmaceutically acceptable salt thereof. Values for the variables in Structural Formulae (I-A)-(I-C), (II-A)-(II-C), and (III-A)-(III-C) are as described for Structural Formula (I).

In a third embodiment, the invention provides a compound represented by structural formula (I), (I-A)-(I-C), (II-A)-(II-C), or (III-A)-(III-C), wherein $R_4$ and $R_5$, together with the nitrogen to which they are attached, form 4-7 membered monocyclic heterocyclyl or 6-12 membered bridged heterocyclyl, wherein the 4-7 membered monocyclic heterocyclyl or 6-12 membered bridged heterocyclyl is optionally substituted with 1-3 groups selected from —F, —Cl, —Br, —CN, —$NH_2$, —OH, oxo, —($C_1$-$C_4$)alkyl, —($C_1$-$C_4$)haloalkyl, —($C_1$-$C_4$)alkoxy, —($C_1$-$C_4$)haloalkoxy, —($C_1$-$C_4$)alkylene-OH, or —($C_1$-$C_4$)alkylene-$NH_2$. Values for the remainder of the variables are as described for Structural Formula (I).

In a fourth embodiment, the invention provides a compound represented by structural formula (I), (I-A)-(I-C), (II-A)-(II-C), or (III-A)-(III-C), wherein $R^a$ for each occurrence is independently —H, —($C_1$-$C_6$)alkyl, —$(CH_2)_n$—($C_3$-$C_7$)cycloalkyl, —$(CH_2)_n$-4-7 membered monocyclic heterocyclyl, —$(CH_2)_n$-bridged ($C_6$-$C_{12}$)cycloalkyl, optionally substituted —$(CH_2)_n$-5-10 membered heteroaryl; or —$(CH_2)_n$-6-12 membered bridged heterocyclyl, wherein —($C_1$-$C_6$)alkyl, —$(CH_2)_n$—($C_3$-$C_7$)cycloalkyl, —$(CH_2)_n$-4-7 membered monocyclic heterocyclyl, —$(CH_2)_n$-bridged ($C_6$-$C_{12}$)cycloalkyl, —$(CH_2)_n$-5-10 membered heteroaryl, or —$(CH_2)_n$-6-12 membered bridged heterocyclyl, is optionally substituted with 1-3 groups selected from —F, —Cl, —Br, —CN, —OH, oxo, —($C_1$-$C_4$)alkyl, —($C_1$-$C_4$)haloalkyl, —($C_1$-$C_4$)alkoxy, —($C_1$-$C_4$)haloalkoxy, —($C_1$-$C_4$)alkylene-OH, or —($C_1$-$C_4$)alkylene-$NH_2$, and values for the remainder of the variables are as described above for Structural Formula (I) or in the third embodiment.

In a fifth embodiment, the invention provides a compound represented by structural formula (I), (I-A)-(I-C), (II-A)-(II-C), or (III-A)-(III-C), wherein R is H, —F, —Cl, —Br, —OH, —$(C_1-C_4)$alkyl, —$(C_1-C_4)$haloalkyl, —$(C_1-C_4)$alkoxy, —$(C_1-C_4)$alkylene-OH or 4-7 membered monocyclic heterocyclyl optionally substituted with 1-3 groups selected from —F, —Cl, —Br, —OH, —$(C_1-C_4)$alkyl, —$(C_1-C_4)$haloalkyl, or —$(C_1-C_4)$alkoxy, and values for the remainder of the variables are as described above for Structural Formula (I) or in the third or fourth embodiment.

In a sixth embodiment, the invention provides a compound represented by structural formula (I), (I-A)-(I-C), (II-A)-(II-C), or (III-A)-(III-C), wherein $R_4$ and $R_5$, together with the nitrogen to which they are attached, form N-alkylpiperazinyl or morpholinyl, wherein the piperazinyl or morpholinyl is optionally substituted with 1-2 groups selected from —F, —Cl, —Br, —OH, —$(C_1-C_4)$alkyl, —$(C_1-C_4)$haloalkyl, or —$(C_1-C_4)$alkoxy, and values for the remainder of the variables are as described above for Structural Formula (I), or in the third, fourth, or fifth embodiment.

In a seventh embodiment, the invention provides a compound represented by structural formula (I), (I-A)-(I-C), (II-A)-(II-C), or (III-A)-(III-C), wherein $R^a$ for each occurrence is independently —H, —$(CH_2)_n$—$(C_3-C_6)$cycloalkyl, —$(CH_2)_n$-3-6 membered heterocyclyl, wherein the —$(CH_2)_n$—(C3-C6)cycloalkyl or —$(CH_2)_n$-3-6 membered heterocyclyl is optionally substituted with 1-3 groups selected from —F, —Cl, —Br, —CN, —$NH_2$, —OH, —$(C_1-C_4)$alkyl, or —$(C_1-C_4)$alkoxy; and n is 0 or 1, and values for the remainder of the variables are as described above for Structural Formula (I), or in the third, fourth, fifth, or sixth embodiment.

In an eighth embodiment, the invention provides a compound represented by structural formula (I), (I-A)-(I-C), (II-A)-(II-C), or (III-A)-(III-C), wherein R is H, —$(C_1-C_4)$alkyl, —$(C_1-C_4)$alkoxy, N-piperazinyl optionally substituted with —$CO_2$—$(C_1-C_4)$alkyl, and values for the remainder of the variables are as described above for Structural Formula (I), or in the third, fourth, fifth, sixth, or seventh embodiment. Alternatively, R is H.

In a ninth embodiment, the invention provides a compound represented by structural formula (I), (I-A)-(I-C), (II-A)-(II-C), or (III-A)-(III-C), wherein $R_4$ and $R_5$, together with the nitrogen to which they are attached, form N-methylpiperazinyl or morpholinyl, both of which are optionally substituted with one or two methyl, and values for the remainder of the variables are as described above for Structural Formula (I), or in the third, fourth, fifth, sixth, seventh, or eighth embodiment.

In a tenth embodiment, the invention provides a compound represented by structural formula (I), (I-A)-(I-C), (II-A)-(II-C), or (III-A)-(III-C), wherein $R^a$ for each occurrence is independently —H; —$(C_3-C_6)$cycloalkyl optionally substituted with —OH; —$(CH_2)_n$-tetrahydro-2H-pyran; morpholinyl; piperidinyl optionally substituted with —F, —OH or methyl; or tetrahydrofuran; and n is 0 or 1, and values for the remainder of the variables are as described above for Structural Formula (I), or in the third, fourth, fifth, sixth, seventh, eighth or ninth embodiment.

The invention also includes the compounds depicted by structure and/or described by name in the Exemplification. The invention includes both the neutral form (free base) of these compounds as well as pharmaceutically acceptable salts thereof. Treatments with and/or uses of these compounds includes the neutral form of these compounds as well as pharmaceutically acceptable salts thereof.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-6 carbon atoms, i.e. $(C_1-C_6)$alkyl. As used herein, a "$(C_1-C_6)$alkyl" group means a radical having from 1 to 6 carbon atoms in a linear or branched arrangement. Examples include methyl, ethyl, n-propyl, iso-propyl etc.

"Alkoxy" means an alkyl radical attached through an oxygen linking atom, represented by —O-alkyl. For example, "$(C_1-C_4)$alkoxy" includes methoxy, ethoxy, propoxy, and butoxy.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

"Alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e. $(C_2-C_6)$alkenyl. For example, "$(C_2-C_6)$alkenyl" means a radical having from 2-6 carbon atoms in a linear or branched arrangement.

"Alkynyl" means branched or straight-chain monovalent hydrocarbon radical containing at least one triple bond. Unless otherwise specified, an alkynyl group typically has 2-6 carbon atoms, i.e. $(C_2-C_6)$alkynyl. For example, "$(C_2-C_6)$alkynyl" means a radical having from 2-6 carbon atoms in a linear or branched arrangement.

"Cycloalkyl" means a saturated aliphatic cyclic hydrocarbon radical, typically containing from 3-8 ring carbon atoms, i.e., $(C_3-C_8)$cycloalkyl. $(C_3-C_8)$cycloalkyl includes, but is not limited to, cyclopropyl, cyclobutyl, cyclopentyl, cyclohexyl, cycloheptyl and cyclooctyl.

As used herein, the term "bridged" used alone or as part of a larger moiety as in "bridged cycloalkyl" or "bridged heterocyclyl" refers to a ring system which includes two rings that share at least three adjacent ring atoms. Bridged cycloalkyl typically contains 6-12 ring carbon atoms. Bridged heterocyclyl typically have 6-12 ring atoms selected from carbon and at least one (typically 1 to 4, more typically 1 or 2) heteroatom (e.g., oxygen, nitrogen or sulfur).

The term "aryl" used alone or as part of a larger moiety as in "arylalkyl", "arylalkoxy", or "aryloxyalkyl", means a carbocyclic aromatic ring. It also includes a phenyl ring fused with a cycloalkyl group. The term "aryl" may be used interchangeably with the terms "aryl ring" "carbocyclic aromatic ring", "aryl group" and "carbocyclic aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

The term "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroarylalkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aryl, heterocyclyl or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

"Heterocyclyl" means a saturated or unsaturated non-aromatic 3-12 membered ring radical optionally containing one or more double bonds. It can be monocyclic, bicyclic, tricyclic, or fused. The heterocycloalkyl contains 1 to 4 heteroatoms, which may be the same or different, selected from N, O or S. The heterocyclyl ring optionally contains one or more double bonds and/or is optionally fused with one or more aromatic rings (e.g., phenyl ring). The term "heterocyclyl" is intended to include all the possible isomeric forms. Examples of heterocycloalkyl include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. Examples of polycyclic heterocycloalkyl groups include dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, dihydrobenzisoxazolyl, chroman, chromene, isochroman and isochromene.

Certain of the compounds described herein may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, geometric isomers, including essentially pure stereo or geometric isomers, as well as combination thereof.

In certain instances tautomeric forms of the disclosed compounds exist, such as the tautomeric structures shown below:

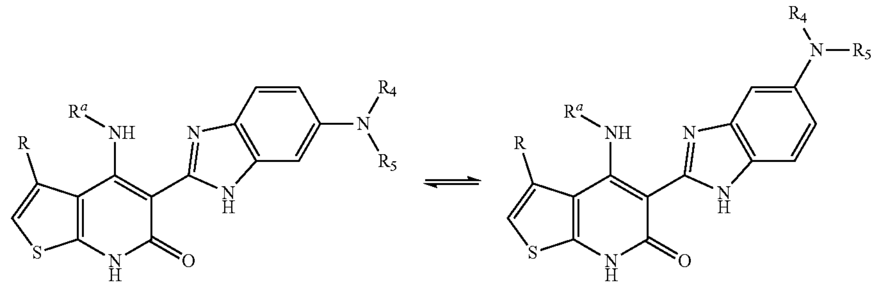

Tautomer

It is to be understood that when a compound herein is represented by a structural formula or designated by a chemical name herein, all other tautomeric forms which may exist for the compound are encompassed by the structural formula.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. "Geometric isomers" are stereoisomers that differ in the orientation of substituent atoms in relationship to a carbon-carbon double bond, to a carbocyclyl ring, or to a bridged bicyclic system.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure (also referred to as "enantiomerically pure"). Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and e.g., the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, acetates, succinates, benzoates and salts with amino acids such as glutamic acid.

Compounds described herein can inhibit HPK1. Thus, generally, compounds described herein are useful in the treatment of diseases or conditions associated with such kinases.

In one embodiment, the compounds described herein are HPK1 inhibitors, and are useful for treating diseases, such as cancer, associated with such kinase(s).

Another aspect of the present teachings relates to a method of treating a subject with cancer comprising administering to the subject an effective amount of a compound described herein. In one embodiment, the compounds described herein inhibit the growth of a tumor.

Cancers that can be treated (including reduction in the likelihood of recurrence) by the methods of the present teachings include breast cancer, colorectal cancer, lung cancer, ovarian cancer, uterine cancer, prostate cancer, leukemias, lymphomas, brain cancer (including glioblastoma multiforme and neuroblastoma), head and neck cancer, pancreatic cancer, melanoma, hepatocellular carcinoma, renal cancer, and soft tissue sarcomas. In one embodiment, the cancer is breast cancer, colon cancer, and ovarian cancer. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma multiforme or ovarian cancer. In another embodiment, the cancer is lung cancer, breast cancer, colon cancer, brain cancer, neuroblastoma, prostate cancer, melanoma, glioblastoma multiforme or ovarian cancer. In yet another embodiment, the cancer is breast cancer, colon cancer and lung cancer. In another embodiment, the cancer is a breast cancer. In yet another embodiment, the cancer is a basal sub-type breast cancer or a luminal B sub-type breast cancer. In yet another embodiment, the cancer is a basal sub-type breast cancer. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

The present teachings also provide methods of treating a subject with a disease comprising administering to the subject an effective amount of a compound represented by Structural Formula (I) in combination with an effective immunomodulatory therapy (also referred as immunotherapy). Immunotherapy is the treatment of disease by using an immunomodulatory agent to induce, enhance, or suppress an immune response. Immunotherapies designed to elicit or amplify an immune response are classified as activation immunotherapies, while immunotherapies that reduce or suppress are classified as suppression immunotherapies. The disease described herein is a cancer.

Immunomodulatory therapies, used alone or in combination approaches, include i) immune checkpoint blockade inhibitors, including but not limited to anti-CTLA4 (cytotoxic T-lymphocyte-associated protein 4) antibodies (e.g. Ipilimumab), agents that disrupt the PD-1/PD-L1 and PD-L2 interaction, e.g. Nivolumab (Opdivo—Bristol Myers Squibb), Pembrolizumab (Keytruda, KM-3475, Merck), Pidilizumab (CT-011, Cure Tech), BMS 936559 (BMS) and MPDL328OA (Roche); and other immune response inhibitory receptors e.g. anti-CD47; ii) cell based therapies (including, but not limited to, dendritic cell therapy (e.g. Sipuleucel T (Provenge) and adoptive T-cell therapies, iii) vaccination strategies; iv) Adoptive T-cell therapy; v) agents that prevent metabolic inhibition of the immune response, including inhibitors of indoleamine 2, 3-dioxygenase (e.g. INCB024360 (Incyte), 1-methyl-D-tryptophan, indoximod (NewLink Genetics)) or arginase; and vi) cytokine-based therapy, e.g., interferons (in particular type I interferon) and interleukins (e.g. interleukin-2).

In one embodiment, the immunomodulatory agent used for the immunomodulatory therapy is a PD-1 inhibitor, for example, an anti-PD1 antibody.

Programmed cell death protein 1, also known as PD-1 and CD279 (cluster of differentiation 279), is a protein that in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2, both of which are members of the B7 family.

PD-1 and its ligands play an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

The PD-1 inhibitor used in the present invention includes, but is not limited to, nivolumab, pembrolizumab, pidilizumab, BMS 936559, MPDL3280A, MSB0010718C or MEDI4736. Among them, BMS 936559, MPDL3280A, MSB0010718C, and MEDI4736 bind ligand PD-L1, all of which are antibodies. Both nivolumab and pembrolizumab are approved by the Food and Drug Administration for treatment of unresectable or metastatic melanoma which no longer responds to other drugs.

Vaccination strategies include anti-microbial immunotherapy, which includes vaccination, involves activating the immune system to respond to an infectious agent.

Adoptive T-cell therapy uses T cell-based cytotoxic responses to attack cancer cells. T cells that have a natural or genetically engineered reactivity to a patient's cancer are generated in vitro and then transferred back into the cancer patient. One study using autologous tumor-infiltrating lymphocytes was an effective treatment for patients with metastatic melanoma. This can be achieved by taking T cells that are found with the tumor of the patient, which are trained to attack the cancerous cells. These T cells are referred to as tumor-infiltrating lymphocytes (TIL) are then encouraged to multiply in vitro using high concentrations of IL-2, anti-CD3 and allo-reactive feeder cells. These T cells are then transferred back into the patient along with exogenous administration of IL-2 to further boost their anti-cancer activity.

The present teachings also provide methods of treating a subject with a cancer comprising administering to the subject an effective amount of a compound represented by Structural Formula (I) in combination with an effective anti-cancer therapy. In one embodiment, the cancer is a metastatic cancer. A "metastatic cancer" is a cancer that has spread from its primary site to other parts of the body.

The anti-cancer therapy described herein includes co-administration of an effective amount of a second anti-cancer agent together with a disclosed HPK-1 inhibitor. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agents suitable for use in the methods described herein include any anti-cancer agents that have been approved for the treatment of cancer. In one embodiment, the anti-cancer agent includes, but is not limited to, a targeted antibody, an angiogenesis inhibitor, an alkylating agent, an antimetabolite, a vinca alkaloid, a taxane, a podophyllotoxin, a topoisomerase inhibitor, a hormonal antineoplastic agent and other antineoplastic agents. In one embodiment, the anti-cancer agent is a PD-1 inhibitor, for example, an anti-PD1 antibody.

In one embodiment, the anti-cancer agents that can be used in methods described herein include, but are not limited to, paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan, cytarabine, etoposide, daunorubicin, bleomycin, mitomycin and adriamycin and a combination thereof.

In one embodiment, the anti-cancer agent and the compound represented by Structural Formula (I) are administered contemporaneously. When administered contemporaneously, the anti-cancer agent and the compound can be administered in the same formulation or in different formulations. Alternatively, the compound and the additional anti-cancer agent are administered separately at different times.

As used herein, "treating a subject with a cancer" includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

In an embodiment, an effective amount of a compound taught herein ranges from about 0.1 to about 1000 mg/kg body weight, alternatively about 1 to about 500 mg/kg body weight. In another embodiment, an effective amount of a compound taught herein ranges from about 0.5 to about 5000 $mg/m^2$, alternatively about from 5 to about 2500 $mg/m^2$, and in another alternative from about 50 to about 1000 $mg/m^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds taught herein can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multi-dose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

The compounds of invention may be prepared by methods known to those skilled in the art, as illustrated by the general schemes and procedures below and by the preparative examples that follow. All starting materials are either commercially available or prepared by methods known to those skilled in the art and the procedures described below.

General synthetic approaches to the claims compounds are provided in the exemplification below, as illustrated in Schemes 1 and 2.

EXEMPLIFICATION

Example A

Synthesis

General Methods

Commercially available starting materials, reagents, and solvents were used as received. In general, anhydrous reactions were performed under an inert atmosphere such as nitrogen or Argon. PoraPak® Rxn CX refers to a commercial cation-exchange resin available from Waters.

Microwave reactions were performed with a Biotage Initiator microwave reactor. Reaction progress was generally monitored by LCMS (Broker Exquire 4000 or Waters Acquity UPLC system). Flash column chromatographic purification of intermediates or final products was performed using a Biotage Isolera with KP-SIL or HP-SIL silica cartridges, or KP-NH basic modified silica and corresponding samplets. Reverse-phase HPLC purification was performed on a Varian PrepStar model SD-1 HPLC system with a Varian Monochrom 10μ C-18 reverse-phase column using a gradient of 10% MeOH/0.05% TFA-$H_2O$ to 90% MeOH/0.05% TFA in $H_2O$ over a 40-min period at a flow rate of 40 mL/min. Reverse phase purification was also performed using a Biotage Isolera equipped with a KP-C18-H column using a between 10-95% MeOH or CH3CN/0.1% TFA in $H_2O$. Proton NMRs were recorded on a Broker 400 MHz spectrometer, and mass spectra were obtained using a Broker Esquire 4000 spectrometer or Waters Acquity UPLC system.

Compound names were generated using the software built into CambridgeSoft-PerkinElmer's ChemBioDraw Ultra version 12.0.

ABBREVIATIONS aq aqueous
anh anhydrous
Ar argon
Boc tert-butoxycarbonyl
br. broad
calcd calculated
d doublet (only when used within 1H NMR spectra)
DCM dichloromethane
de diastereomeric excess
DIPEA diisopropylethylamine
DMF N,N-dimethylformamide
DMSO dimethylsulfoxide
dppf 1,1'-bis(diphenylphosphino) ferrocene
equiv equivalent
Flt3 fms-related tyrosine kinase 3
h hour
HPK1 hematopoietic progenitor kinase 1
HPLC high performance liquid chromatography
IPA isopropanol
KHMDS potassium hexamethyldisilazide
Lck lymphocyte-specific protein tyrosine kinase
LC-MS liquid chromatography coupled to mass spectrometry
LDA lithium diisopropyllamide
LiHMDS lithium hexamethyldisilazide
min minute
m multiplet
MeCN acetonitrile
MS ESI mass spectra, electrospray ionization
NMR nuclear magnetic resonance
O/N overnight
PMB para-methoxybenzyl
prep preparative
rt room temperature
Rt retention time
RP reverse phase
s singlet
satd saturated
t triplet
temp. temperature
TFA trifluoroacetic acid
THF tetrahydrofuran Scheme 1

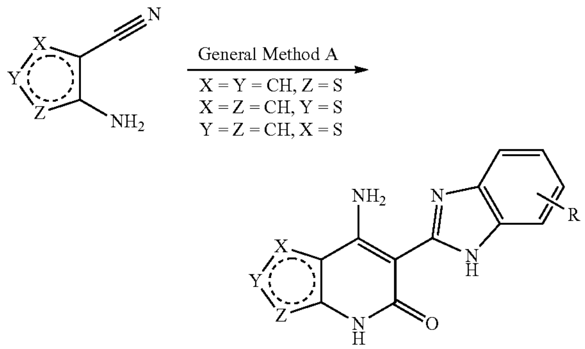

Scheme 2

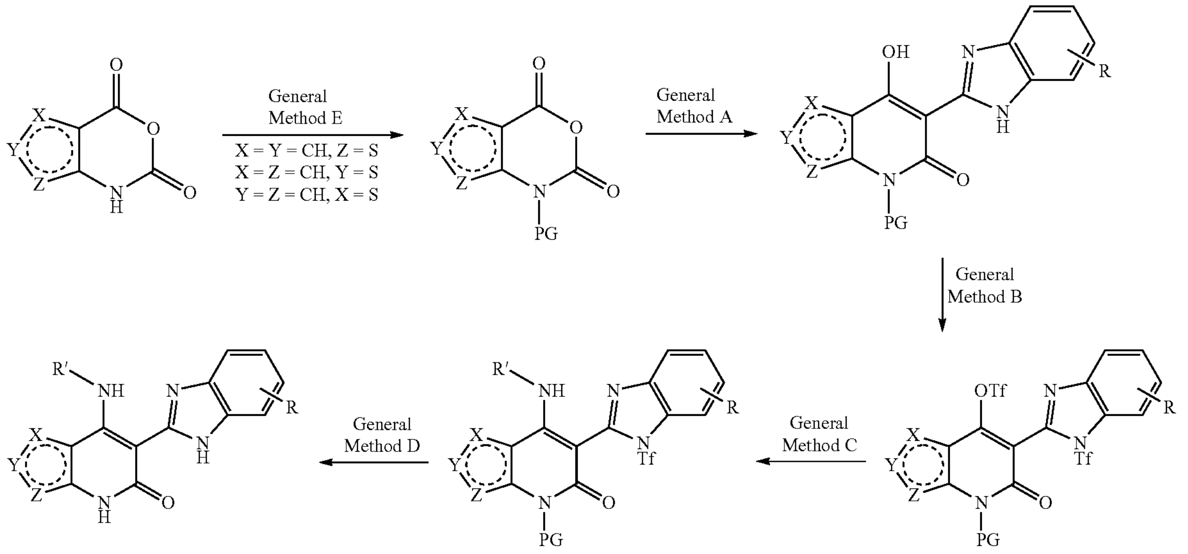

Preparation of Starting Materials

General Method A1 (Base-Induced Cyclization using Benzimidazole Ester)

A solution of aryl oxazine-2,4-dione (1 equiv), or aminoaryl nitrile and substituted 1H-benzo[d]imidazol-2-yl)acetate (1-1.2 equiv) in THF was treated with KHMDS, LiHMDS, or LDA (3-5 equiv). The reaction was stirred at 45° C. for 4-24 h. The reaction was then cooled to rt and quenched with satd aq $NH_4Cl$. The aqueous layer was extracted with EtOAc or DCM, and the combined organic extracts were dried over $MgSO_4$, filtered and concentrated. Crude product was purified by column chromatography or prep-HPLC to give the desired product.

General Method A2 (Two-Step, Base-Induced Cyclization using Benzimidazole Ester)

A solution of aryl oxazine-2,4-dione (1 equiv), or aminoaryl nitrile and substituted 1H-benzo[d]imidazol-2-yl)acetate (1-1.2 equiv) in was treated with KHMDS, LiHMDS, $KOBu^t$ or LDA (3-5 equiv) at 45° C. for 2-4 h. The reaction was then cooled to rt and quenched with satd aq $NH_4Cl$. The aqueous layer was extracted with EtOAc or DCM, and the combined organic extracts were dried over $MgSO_4$, filtered and concentrated. The uncyclized addition adduct was separated by column chromatography, dissolved in THF and treated with KHMDS, LiHMDS, or LDA (3-5 equiv). The reaction was stirred at 45° C. for 1-4 h. The reaction was then cooled to rt and quenched with satd aq $NH_4Cl$. The aqueous layer was extracted with EtOAc or DCM, and the combined organic extracts were dried over $MgSO_4$, filtered and concentrated. Crude product was purified by column chromatography or prep-HPLC to give the desired product.

General Method A3 (Two-Step, Base-Induced Cyclization using Benzimidazole Ester)

A solution of aminoaryl nitrile and substituted 1H-benzo[d]imidazol-2-yl)acetate (1 equiv) in THF was treated with LiHMDS, or LDA (5 equiv) (step 1). The reaction was stirred at 35-40° C. for 1-1.5 h. The reaction was then cooled to rt and quenched with satd aq $NH_4Cl$ and concentrated. Crude product was purified by prep-HPLC to give uncyclized intermediate that was neutralized, dried and subjected to the conditions described in general method A1 using LiHMDS (step 2).

General Method B (Triflate Formation)

A solution of benzimidazol-2-yl arylpyridinone derivate (1 equiv) and pyridine (20 equiv) in DCM was treated with $Tf_2O$ (8 equiv). The reaction was stirred at 0° C. for 2-8 h. The reaction was then quenched with satd aq $NaHCO_3$. The aqueous layer was extracted with DCM, and the combined organic extracts were dried over $MgSO_4$, filtered and concentrated. Crude product was used in the next step without further purification.

General Method C (Amine Substitution)

A solution of benzoimidazol-2-yl arylpyridinone bistriflate derivate (1 equiv) in MeCN, DCM, or DMF was treated with amine (1.2-3 equiv). In the case where the amine is a salt (e.g. HCl), the amine salt was dissolved in MeOH or DMF and passed through a PoraPak Rxn CX ion exchange column to yield the free base which was added to the reaction mixture. The reaction mixture was stirred at rt or up to 45° C. for 1-48 h. Solvent was removed and the crude product was purified by column chromatography or prep-HPLC to give the desired product.

General Method D (Global Deprotection)

A solution of protected benzoimidazol-2-yl arylpyridinone derivate (1 equiv) in TFA/conc. HCl (7:1 v/v) was heated at 80-100° C. for 3-24 h. Solvent was removed and the crude product was purified by column chromatography (free base) or prep-HPLC (TFA salt) to give the desired product. To generate the desired product as a HCl salt, the free base was dissolved in MeOH and 1 M HCl-$Et_2O$ (2-4 equiv) was added at rt. The solution was stirred for 5 min and azeotroped twice with MeOH.

General Method E (PMB-Protection)

A solution of thiaisatoic anhydride (1 equiv), 1-(chloromethyl)-4-methoxybenzene (1-1.2 equiv), $K_2CO_3$ (1-1.2 equiv) and/or KI (1-1.2 equiv) in DMF was stirred at rt for 4-24 h. The reaction mixture was then slowly added to $H_2O$, precipitate was collected by vacuum filtration to give the desired.

INTERMEDIATES 1H-thieno[3,4-d][1,3]oxazine-2,4-dione

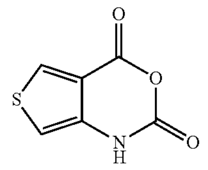 [SMILES: O=c1[nH]c2cscc2c(=O)o1]

To a solution of 4-tert-butoxycarbonylamino-thiophene-3-carboxylic acid (2.5 g, 10.2 mmol) in PhMe (25 mL) was added oxalyl chloride (1.29 mL, 15.3 mmol) at rt. The reaction mixture was gradually heated to 95° C. and stirred at 95° C. for 1 h. After reaction completion, the reaction was cooled to rt and filtered. The solid was washed with hexanes (2×5 mL), and dried under vacuum to afford the title compound as a cream solid (1.61 g, 93%). $^1H$ NMR (400 MHz, DMSO-$d_6$) δ 11.57 (s, 1H), 8.64 (d, J=3.2 Hz, 1H), 6.89 (d, J=2.8 Hz, 1H); MS ESI $[M+H]^+$ 170.0, calcd for $[C_6H_3NO_3S+H]^+$ 169.9.

1-(4-methoxybenzyl)-1H-thieno[3,4-d][1,3]oxazine-2,4-dione

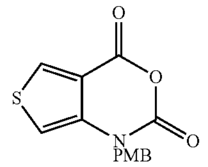

According to general method E, to a solution of 1H-thieno[3,4-d][1,3]oxazine-2,4-dione (1.6 g, 9.45 mmol) in anh DMF (20 mL), $K_2CO_3$ (1.56 g, 11.3 mmol) was added followed by KI (0.62 g, 3.78 mmol) under stirring at rt. PMBCl (1.54 mL, 11.3 mmol) was added dropwise over 10 min and the reaction mixture was stirred for a further 2 h. After reaction completion the reaction mixture was poured into $H_2O$ (200 mL) to precipitate the product which was filtered, washed with $H_2O$ and dried to afford the title compound as an off-white solid (2.3 g, 84%). $^1H$ NMR (400 MHz, $CDCl_3$) δ 8.35 (d, J=3.2 Hz, 1H), 7.31 (d, J=8.8 Hz, 2H), 6.89 (d, J=8.8 Hz, 2H), 6.62 (d, J=3.2 Hz, 1H), 5.08 (s, 2H), 3.80 (s, 3H); MS ESI $[M+H]^+$ 291.2, calcd for $[C_{14}H_{11}NO_4S+H]^+$ 290.0.

7-hydroxy-4-(4-methoxybenzyl)-6-(6-(4-methylpiperazin-1-yl)-1H-benzo[d]imidazol-2-yl)thieno[3,2-b]pyridin-5(4H)-one

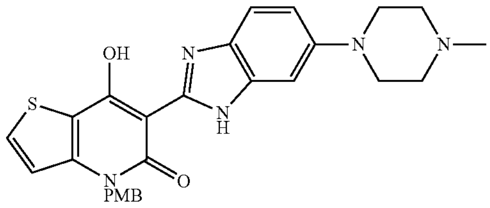

According to general method A1, to a solution of 1-(4-methoxybenzyl)-1H-thieno[3,2-d][1,3]oxazine-2,4-dione [Tetrahedron (1999) 55 6167-6174] (2.89 g, 10 mmol), ethyl 2-(6-(4-methylpiperazin-1-yl)-1H-benzo[d]imidazol-2-yl) acetate [J. Med. Chem. (2009), 52, 278-292] (3.02 g, 10 mmol), LiHMDS (1 M in THF, 4 mL, 4 mmol) were used to generate the title compound as an orange solid (2.65 g, 51%). $^1$H NMR (400 MHz, $CDCl_3$) δ 13.68 (br.s., 1H), 12.57 (s, 1H), 7.55 (dd, J=5.2, 2.0 Hz, 1H), 7.40-7.32 (m, 1H), 7.23 (d, J=8.8 Hz, 2H), 7.04-6.93 (m, 3H), 6.85 (d, J=8.8 Hz, 2H), 5.37 (s, 2H), 3.77 (s, 3H), 3.30-3.19 (m, 4H), 2.69-2.58 (m, 4H), 2.39 (s, 3H); MS ESI $[M+H]^+$ 502.1, calcd for $[C_{27}F_{27}N_5O_3S+H]^+$ 502.2.

4-hydroxy-7-(4-methoxybenzyl)-5-(6-(4-methylpiperazin-1-yl)-1H-benzo[d]imidazol-2-yl)thieno[2,3-b]pyridin-6(7H)-one

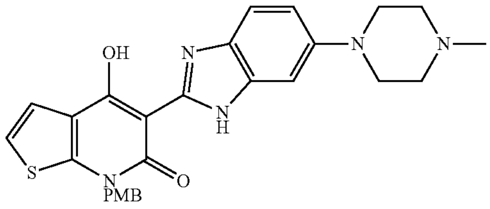

According to general method A2, a solution of 1(4-methoxybenzyl)-1H-thieno[2,3-d][1,3]oxazine-2,4-dione (0.40 g, 1.4 mmol), ethyl 2-(6-(4-methylpiperazin-1-yl)-1H-benzo[d]imidazol-2-yl)acetate (0.46 g, 1.5 mmol), and LDA (1 M in THF, 6.2 mL, 4.5 mmol) were used to generate the title compound as a brown solid (0.220 g, 32%). $^1$H NMR (400 MHz, $CDCl_3$) δ 13.87 (br.s., 1H), 12.52 (s, 1H), 7.49 (dd, J=14.9 Hz, 1H), 7.40-7.24 (m, 3H), 7.03-6.64 (m, 5H), 5.28 (d, J=13.8 Hz, 2H), 3.76 (s, 3H), 3.21 (d, J=18.8 Hz, 4H), 2.65 (m, d, J=19.1 Hz, 4H), 2.41 (s, 3H); MS ESI $[M+H]^+$ 502.3, calcd for $[C_{27}H_{27}N_5O_3S+H]^+$ 502.2.

| | | |
|---|---|---|
| 7-hydroxy-4-(4-methoxybenzyl)-6-(6-morpholino-1H-benzo[d]imidazol-2-yl)thieno[3,2-b]pyridin-5(4H)-one | 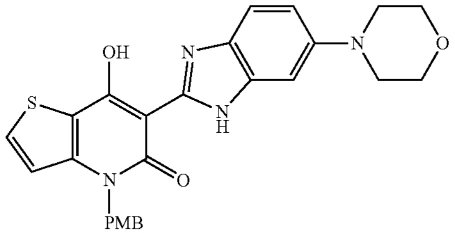 | 325 mg (48%) Brown solid; free base |
| Reagents (General Method A1): 1-(4-methoxybenzyl)-1H-thieno[3,2-d][1,3]oxazine-2,4-dione [Tetrahedron (1999) 55 6167-6174] (0.4 g, 1.4 mmol), ethyl 2-(6-morpholino-1H-benzo[d]imidazol-2-yl)acetate [*J. Med. Chem.* (2009), 52, 278-292] (0.4 g, 1.4 mmol), LiHMDS (5.5 mL, 5.5 mmol)<br>$^1$H NMR (400 MHz, $CDCl_3$) δ 13.73-13.60 (m, 1H), 12.64-12.52 (m, 1H), 7.54 (d, J = 5.3 Hz, 1H), 7.42-7.29 (m, 2H), 7.21 (d, J = 7.8 Hz, 2H), 7.03-6.89 (m, 2H), 6.85 (d, J = 9.0 Hz, 2H), 5.37 (br. s, 2H), 3.83-3.98 (m, 4H), 3.77 (s, 3H), 3.23-3.09 (m, 4H); MS ESI $[M + H]^+$ 489.2, calcd for $[C_{26}H_{24}N_4O_4S + H]^+$ 489.2. | | |
| 4-hydroxy-7-(4-methoxybenzyl)-5-(6-morpholino-1H-benzo[d]imidazol-2-yl)thieno[2,3-b]pyridin-6(7H)-one | 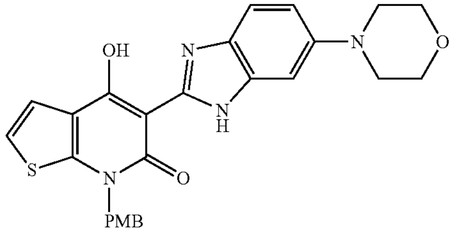 | 445 mg (24%) brown solid; Free base |
| Reagents (General Method A1): 1-(4-methoxybenzyl)-1H-thieno[2,3-d][1,3]oxazine-2,4-dione (0.40 g, 1.4 mmol), ethyl 2-(6-morpholino-1H-benzo[d]imidazol-2-yl)acetate (0.4 g, 1.4 mmol), LDA (17 mL, 17 mmol). MS ESI $[M + H]^+$ 489.2, calcd for $[C_{26}H_{24}N_4O_4S + H]^+$ 489.1. | | |

ethyl 3-(4-((4-methoxybenzyl)amino)thiophen-3-yl)-2-(6-(4-methylpiperazin-1-yl)-1H-benzo [d]imidazol-2-yl)-3-oxopropanoate

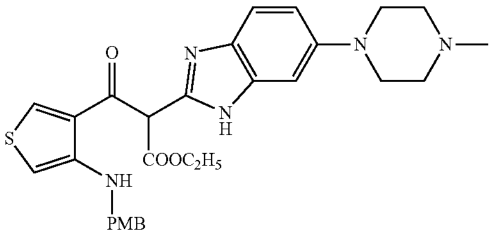

To a solution of ethyl 2-(6-(4-methylpiperazin-1-yl)-1H-benzo[d]imidazol-2-yl)acetate (2.58 g, 8.55 mmol) and 1-(4-methoxy benzyl)-1H-thieno[3,4-d][1,3]oxazine-2,4-dione (2.46 g, 8.55 mmol) in anh THF (48 mL), 1 M LDA (34 mL, 1 M in THF/hexane, 34 mmol) was added dropwise at 40° C. under Ar. The resulting brown solution was stirred at 40° C. for 1 h and then quenched with aq $NH_4Cl$ (50 mL) at rt. The reaction mixture was diluted with $H_2O$ (50 mL) and extracted with DCM (2×200 mL). The combined organic layers were washed once with $H_2O$, dried over $Na_2SO_4$, and concentrated to give crude ester. The crude product was purified by flash chromatography (gradient: EtOAc/hex 0-40%, followed by MeOH/DCM 0-25%) to give the title compound as a light brown solid (3.05 g, 65%). MS ESI $[M+H]^-$ 548.2, calcd for $[C_{29}H_{33}N_5O_4S+H]^+$ 548.2.

4-hydroxy-1-(4-methoxybenzyl)-3-(6-(4-methylpiperazin-1-yl)-1H-benzo[d]imidazol-2-yl)thieno[3,4-b]pyridin-2(1H)-one

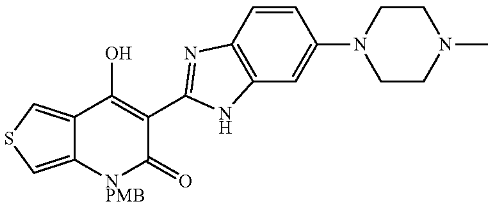

Ethyl 3-(4-((4-methoxybenzyl)amino)thiophen-3-yl)-2-(6-(4-methylpiperazin-1-yl)-1H-benzo[d]imidazol-2-yl)-3-oxopropanoate (3.05 g, 5.57 mmol), described above, was dissolved in anh THF (30 mL) at rt under Ar. A solution of LDA (16.8 mL, 1 M in THF/hexane, 16.71 mmol) was added dropwise at 40° C. The resulting brown solution was stirred at 40° C. for 1 h and then quenched with aq $NH_4Cl$ (25 mL) at rt. The mixture was diluted with $H_2O$ (25 mL) and extracted with DCM (2×250 mL). The combined organic layers were washed once with $H_2O$, dried over $Na_2SO_4$, and concentrated to give crude product. The crude product was purified by flash chromatography (gradient: MeOH/DCM 0-20%) to give the title compound as a light brown solid (1.81 g, 65%). $^1H$ NMR (400 MHz, DMSO-$d_6$) δ 13.8-13.25 (m, 1H), 8.13 (d, J=3.6 Hz, 1H), 7.58 (d, J=8.8 Hz, 1H), 7.36-7.29 (m, 3H), 7.06-7.02 (m, 1H), 6.97 (d, J=3.6 Hz, 1H), 6.86 (d, J=8.4 Hz, 2H), 5.19 (s, 2H), 3.69 (s, 3H), 3.16 (br.s, 4H), 2.60 (br.s, 4H), 2.31 (s, 3H); a signal due to OH group cannot be readily detected. MS ESI 502.1 $[M+H]^+$, calcd for $[C_{27}H_{27}N_5O_3S+H]^+$ 502.2.

7-(4-methoxybenzyl)-5-(5 and/or 6)-(4-methylpiperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate

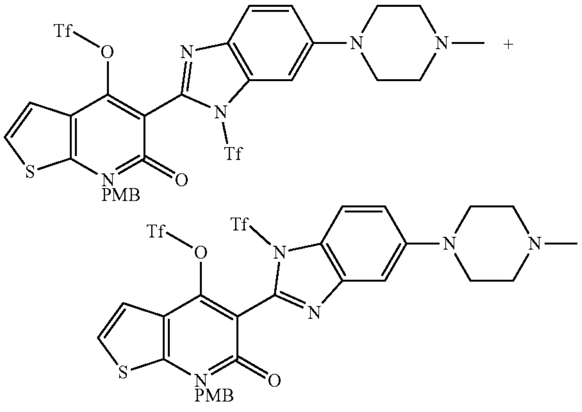

Synthesized according to general method B using 4-hydroxy-7-(4-methoxybenzyl)-5-(6-(4-methylpiper-azin-1-yl)-1H-benzo [d]imidazol-2-yl)thieno[2,3-b]py-ridin-6 (7H)-one (0.22 g, 0.44 mmol), $Tf_2O$ (0.60 mL, 3.5 mmol), and pyridine (0.72 mL, 8.8 mmol). The title compounds obtained as an indeterminate mixture of regioisomers, were used in the next step without purification. MS ESI $[M+H]^+$ 766.1, calcd for $[C_{29}H_{25}F_6N_5O_7S_3+H]^+$ 766.1.

1-(4-methoxybenzyl)-3-(5 and/or 6-(4-methylpiperazin-1-yl)-1-((trifluoromethyl)sulfonyl)-1H-benzo [d]-imidazol-2-yl)-2-oxo-1,2-dihydrothieno[3,4-b] pyridin-4-yl trifluoromethanesulfonate

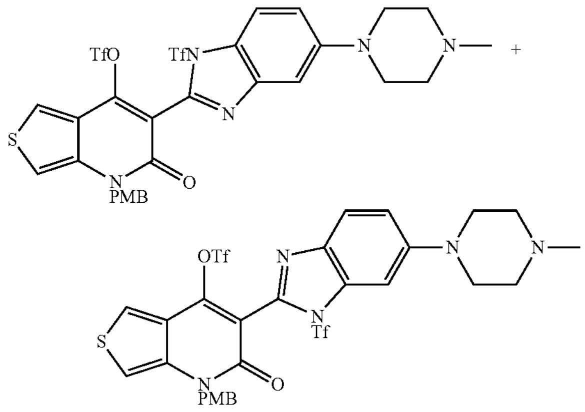

According to general method B, a solution of 4-hydroxy-1-(4-methoxybenzyl)-3-(6-(4-methylpiperazin-1-yl)-1H-benzo [d]imidazol-2-yl)thieno[3,4-b]pyridin-2(1H)-one (220 mg, 0.43 mmol) and pyridine (708 mL, 8.76 mmol) in DCM (12 mL) was added $Tf_2O$ (558 mL, 3.50 mmol) at −5° C. The reaction was stirred between −5 and 0° C. for 1 h. The reaction was quenched with satd aq $NaHCO_3$. The aqueous layer was extracted with DCM, and the combined organic extracts were dried over $Na_2SO_4$, and concentrated under vacuum to give dark brown oil. The crude product, obtained as an indeterminate mixture of regioisomers, was used directly in the next step without further purification. MS ESI $[M+H]^+$ 766.0, calcd for $[C_{29}H_{25}F_6N_5O_7S_3+H]^+$ 766.1.

7-(4-methoxybenzyl)-5-(5 and/or 6-morpholino-1-((trifluoromethyl)sulfonyl)-1H-benzo[d]imidazol-2-yl)-6-oxo-6,7-dihydrothieno[2,3-b]pyridin-4-yl trifluoromethanesulfonate

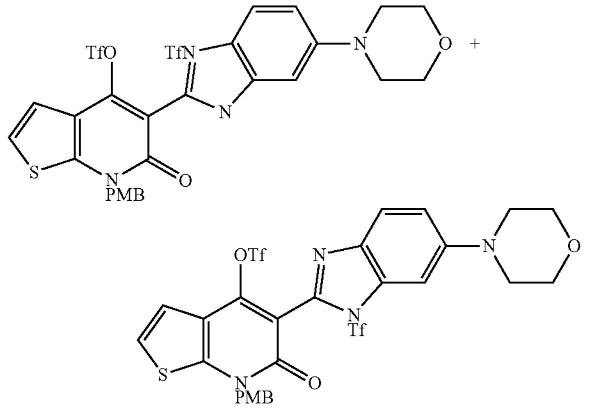

According to general method B, a solution of 4-hydroxy-7-(4-methoxybenzyl)-5-(6-morpholino-1H-benzo[d]imidazol-2-yl)-thieno[2,3-b]pyridin-6(7H)-one (200 mg, 0.41 mmol) and pyridine (0.66 mL, 8.2 mmol) in DCM (20 mL) was added $Tf_2O$ (0.55 mL, 3.28 mmol) at 0° C. The reaction mixture was stirred at 0° C. for 2 h and then quenched with satd aq $NaHCO_3$. The aqueous layer was extracted with DCM. The combined organic extracts were dried over $Na_2SO_4$, and concentrated to give the crude title compound (mixture of two regioisomers) as brown oil which was used directly in the subsequent step without further purification considering quantitative yield. MS ESI $[M+H]^+$ 753.0, calcd for $[C_{28}H_{22}F_6N_4O_8S_3+H]^+$ 752.9.

5-methyl-1H-thieno[2,3-d][1,3]oxazine-2,4-dione

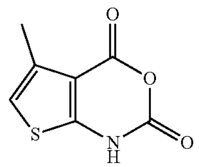

To a solution of KOH (0.49 g, 8.76 mmol) in $H_2O$ (20 mL) was added methyl 2-amino-4-methyl-3-thiophene carboxylate (1.0 g, 5.84 mmol) at rt. The resulting reaction was heated to 90° C. for 2 h and then cooled to 0° C. A solution of triphosgene (0.866 g, 2.92 mmol) in PhMe (12 mL) was added dropwise over 10 min. The resulting solution was gradually warmed to rt and stirred for 2 h. The resulting solid was filtered, washed with $H_2O$ and dried to afford the title compound as a light pink solid (0.65 g, 61%). $^1H$ NMR (400 MHz, $CD_3OD$) δ 6.65 (d, J=1.2 Hz, 1H), 2.42 (d, J=1.2 Hz, 3H); MS ESI $[M+H]^+$ 184.0, calcd for $[C_7H_5NO_3S+H]^+$ 184.0.

1-(4-methoxybenzyl)-5-methyl-1H-thieno[2,3-d][1,3]oxazine-2,4-dione

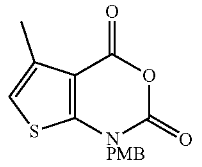

To a solution of 5-methyl-1H-thieno[2,3-d][1,3]oxazine-2,4-dione (0.625 g, 3.41 mmol) in anh DMF (9 mL), $K_2CO_3$ (0.566 g, 4.09 mmol) was added followed by KI (0.142 g, 0.85 mmol) under stirring at rt. PMB-Cl (0.56 mL, 4.06 mmol) was added dropwise to the reaction over 10 min and stirred for further 2 h. The reaction mixture was poured into $H_2O$ (100 mL) to precipitate the product which was filtered, washed with $H_2O$ and dried to afford the title compound as a light brown solid (0.935 g, 91%). $^1H$ NMR (400 MHz, $CDCl_3$) δ 8 7.38 (d, J=8.8 Hz, 2H), 6.90-6.88 (m, 2H), 6.46 (d, J=1.2 Hz, 1H), 5.05 (s, 2H), 3.80 (s, 3H), 2.42 (d, J=1.2 Hz, 3H); MS ESI $[M+H]^-$ 304.2, calcd for $[C_{15}H_{13}NO_4S+H]^-$ 304.1.

4-hydroxy-7-(4-methoxybenzyl)-3-methyl-5-(6-(4-methylpiperazin-1-yl)-1H-benzo[d]imidazol-2-yl)thieno[2,3-b]pyridin-6(7H)-one

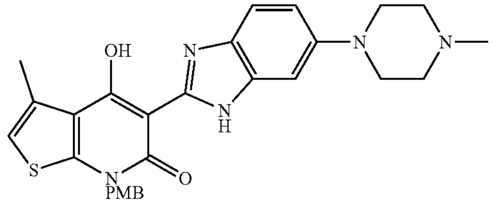

A solution of LDA (34 mL, 1 M in THF/hexane, 34 mmol) was added dropwise to a solution of ethyl 2-(6-(4-methylpiperazin-1-yl)-1H-benzo[d]imidazol-2-yl)acetate (922 mg, 3.04 mmol) and 1-(4-methoxy benzyl)-5-methyl-1H-thieno[2,3-d][1,3]oxazine-2,4-dione (925 mg, 3.04 mmol) in anh THF (28 mL) at 40° C. under Ar. The resulting brown solution was stirred at 40° C. for 2 h and then quenched with aq, $NH_4Cl$ (25 mL) at rt. The reaction mixture was diluted with $H_2O$ (25 mL) and extracted with DCM (2×100 mL). The combined organic layers were washed once with $H_2O$, dried over $Na_2SO_4$, and concentrated to give mixture of product and uncyclized ester. The crude mass was purified by flash chromatography (gradient: EtOAc/hex 0-40%, followed by MeOH/DCM 0-25%) to give mixture of product and uncyclized ester (900 mg).

Above mixture of product and uncyclized ester (900 mg) was dissolved in anh THF (9 mL) at rt under Ar. A solution of LDA (5 mL, 1 M in THF/hexane) was added dropwise at 40° C. The resulting brown solution was stirred at 40° C. for 1 h and worked up it as per above to give crude product. The crude product was purified by flash chromatography (gradient: MeOH/DCM 0-20%) to give the title compound as a cream solid (325 mg, 21%). $^1H$ NMR (400 MHz, $CDCl_3$) δ 12.54 (s, 1H), 7.38 (d, J=8.4 Hz, 1H), 7.33 (d, J=8.4 Hz, 2H), 7.01-6.98 (m, 2H), 6.85 (d, J=8.8 Hz, 2H), 6.40 (s, 1H), 5.26

(s, 2H), 3.80-3.61 (m, 6H), 3.60-3.51 (m, 4H), 2.89-2.88 (m, 4H), 2.63 (s, 3H); the signal due to OH group cannot be readily detected. MS ESI [M+H] 516.2, calcd for $[C_{28}H_{29}N_5O_3S+H]^+$ 516.2.

7-(4-methoxybenzyl)-3-methyl-5-(5 and/or 6)-(4-methylpiperazin-1-yl)-1-((trifluoromethyl)sulfonyl)-1H-benzo[d]imidazol-2-yl)-6-oxo-6,7-dihydrothieno [2,3-b]pyridin-4-yl trifluoromethanesulfonate

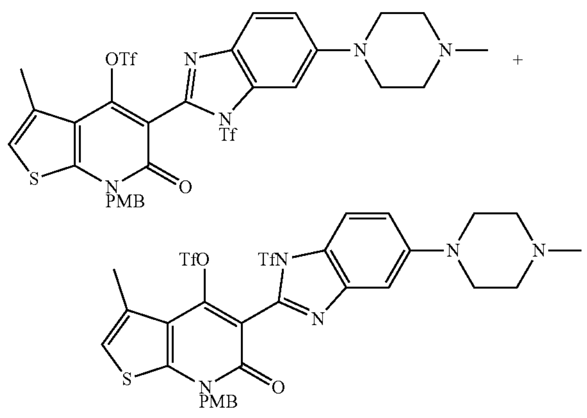

The title compound was prepared according to general method B by utilizing 4-hydroxy-7-(4-methoxy-benzyl)-3-methyl-5-(6-(4-methylpiper-azin-1-yl)-1H-benzo[d]imidazol-2-yl) thieno[2,3-b]pyridin-6(7H)-one (320 mg, 0.62 mmol), pyridine (1.0 mL, 12.4 mmol), $Tf_2O$ (0.833 mL, 4.96 mmol) in DCM (12 mL) to give a dark brown oil. The crude product, obtained as an indeterminate mixture of 2 regioisomers, was used directly in the next step without further purification. MS ESI $[M+H]^+$ 780.0, calcd for $[C_{30}H_{27}F_6N_5O_7S_3+H]^+$780.1.

ethyl 2-(6-((3r,5s)-rel-3,4,5-trimethylpiperazin-1-yl)-1H-benzo[d]imidazol-2-yl)acetate A. 2-nitro-5-((3r,5s)-rel-3,4,5-trimethylpiperazin-1-yl)aniline

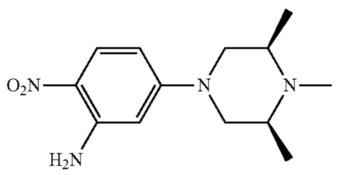

A mixture of 5-chloro-2-nitroaniline (1.73 g, 10 mmol), (3r,5s)-rel-1,2,6-trimethylpiperazine (1.41 g, 11 mmol) and $K_2CO_3$ (2.72 g, 20 mmol) was irradiated in microwave at 140° C. for 4 h. $H_2O$ (150 mL) was then added with stirring, suction filtered, rinsed with $H_2O$ and dried to give the title compound as a brown solid (2.47 g, 94%). $^1H$ NMR (400 MHz, DMSO-$d_6$) δ 7.79 (d, J=10.0 Hz, 1H), 7.23 (s, 2H, $NH_2$), 6.41 (dd, J=9.6, 1.6 Hz, 1H), 6.20 (d, J=2.4 Hz, 1H), 3.77 (d, J=12.4 Hz, 2H), 2.59 (t, J=11.8 Hz, 2H), 2.19-2.11 (m, 2H), 2.16 (s, 3H), 1.05 (d, J=6.0 Hz, 6H); MS ESI $[M+H]^+$ 265.3, calcd for $[C_{13}H_{20}N_4O_2+H]^+$ 265.2.

B. 4-((3r,5s)-rel-3,4,5-trimethylpiperazin-1-yl)benzene-1,2-diamine

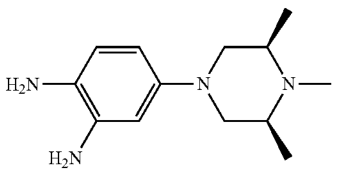 [SMILES: C[C@@H]1CN(c2ccc([N+](=O)[O-])c(N)c2)C[C@H](C)N1C]

To a suspension of 2-nitro-5-((3r,5s)-rel-3,4,5-trimethyl-piperazin-1-yl)aniline (2.47 g, 9.4 mmol) in MeOH (30 mL) was added 10% Pd/C (247 mg, 10% wt.). The resulting mixture was hydrogenated under $H_2$ balloon O/N. After additional 10% Pd/C (124 mg, 5% wt.) was added, it was hydrogenated under $H_2$ balloon O/N, filtered, concentrated and dried to give the title compound as a dark brown solid (2.25 g, quantitative). $^1H$ NMR (400 MHz, $CD_3OD$) δ 6.66 (d, J=8.4 Hz, 1H), 6.47 (d, J=2.4 Hz, 1H), 6.31 (dd, J=8.4, 2.8 Hz, 1H), 3.35-3.25 (m, 2H), 2.47-2.40 (m, 4H), 2.34 (s, 3H), 1.18 (d, J=5.6 Hz, 6H); MS ESI $[M+H]^+$ 235.3, calcd for $[C_{13}H_{22}N_4+H]^+$ 235.2.

C. ethyl 2-(6-((3r,5s)-rel-3,4,5-trimethylpiperazin-1-yl)-1H-benzo[d]imidazol-2-yl)acetate

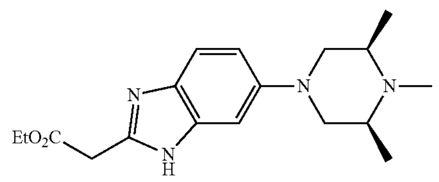 [SMILES: CCOC(=O)Cc1nc2ccc(N3C[C@@H](C)N(C)[C@@H](C)C3)cc2[nH]1]

To a solution of 4-((3r,5s)-rel-3,4,5-trimethylpiperazin-1-yl)benzene-1,2-diamine (2.25 g, 9.4 mmol) in EtOH (40 mL) was added ethyl 3-ethoxy-3-iminopropionate hydrochloride (2.93 g, 15 mmol). The resulting mixture was heated at 80° C. for 2 h. After removal of solvents, it was diluted with DCM/MeOH (100 mL/10 mL), basified with satd aq $NaHCO_3$ (30 mL) and separated. The aqueous layer was extracted with DCM (60 mL×2) and the combined extracts were concentrated and purified by flash chromatography (gradient: 100% EtOAc, then MeOH/DCM 0-20%) to give the title compound as a dark orange solid (2.32 g, 73%). $^1H$ NMR (400 MHz, $CDCl_3$) δ 10.13 (br s, 1H, NH), 7.53-6.88 (m, 3H), 4.25 (q, J=7.2 Hz, 2H), 4.03 (s, 2H), 3.43 (d, J=11.2 Hz, 2H), 2.61 (t, J=11.2 Hz, 2H), 2.50-2.41 (m, 2H), 2.35 (s, 3H), 1.32 (t, J=7.2 Hz, 3H), 1.19 (d, J=6.0 Hz, 6H); MS ESI $[M+H]^+$ 331.3, calcd for $[C_{18}H_{26}N_4O_2+H]^+$ 331.2.

7-hydroxy-4-(4-methoxy benzyl)-6-(6-((3r,5s)-rel-3,4,5-trimethylpiperazin-1-yl)-1H-benzo[d]imidazol-2-yl)thieno[3,2-b]pyridin-5(4H)-one

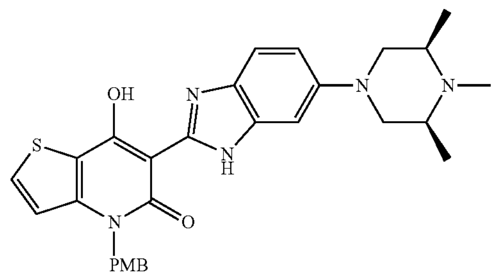

To a mixture of 1-(4-methoxybenzyl)-1H-thieno[3,2-d][1,3]oxazine-2,4-dione (1.16 g, 4 mmol) and ethyl 2-(6-((3r,5s)-rel-3,4,5-trimethylpiperazin-1-yl)-1H-benzo[d]imidazol-2-yl)acetate (990 mg, 3 mmol) in THF (20 mL) was added LDA (1.0 M in THF/hex, 10 mL, 10 mmol) dropwise at rt. After addition, the resulting mixture was stirred at 40° C. for 1 h, diluted with DCM, quenched with satd aq $NH_4Cl$ and extracted with DCM. The combined extracts were concentrated and purified by flash chromatography (gradient: 20-100% EtOAc/hex, then MeOH (0.5% $NH_3$)/DCM 0-20%) to give a mixture of cyclized and uncyclized product as a brown foam (1.10 g). The mixture was redissolved in THF (15 mL) and LDA (1.0 M in THF/hex, 6 mL, 6 mmol) was added dropwise at rt. The process and workup were both the same as above. The title compound was obtained as an orange solid (630 mg, 40%). MS ESI $[M+H]^+$ 530.3, calcd for $[C_{29}H_{31}N_5O_3S+H]^+$ 530.2.

4-(4-methoxybenzyl)-5-oxo-6-(1-((trifluoromethyl)sulfonyl)-(5 and/or 6)-((3r,5s)-rel-3,4,5-trimethylpiperazin-1-yl)-1H-benzo[d]imidazol-2-yl)-4,5-dihydrothieno[3,2-b]pyridin-7-yl trifluoromethane sulfonate

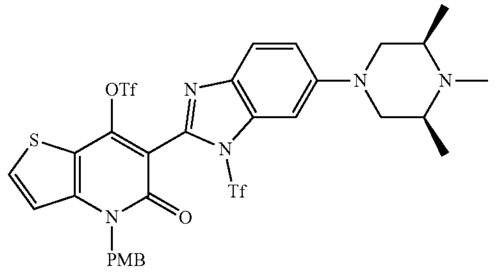

+

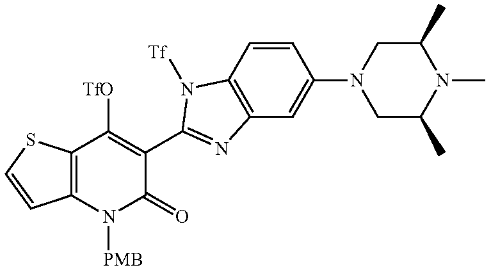

According to general method B, a solution of 7-hydroxy-4-(4-methoxybenzyl)-6-(6-((3r,5s)-rel-3,4,5-trimethyl-piperazin-1-yl)-1H-benzo[d]imidazol-2-yl)thieno[3,2-b]pyridin-5(4H)-one (106 mg, 0.2 mmol) in DCM (15 mL) at 0° C. was added pyridine (0.32 mL, 4 mmol), followed by $Tf_2O$ (0.27 mL, 1.2 mmol). The resulting mixture was stirred at 0° C. for 1 h, diluted with DCM (10 mL), quenched with satd aq $NaHCO_3$ (15 mL), extracted with DCM (20 mL×2) and concentrated to give the crude title compound (an indeterminate mixture of two regioisomers) as a brown oil which was used directly in the subsequent steps. MS ESI $[M+H]^+$ 794.1, calcd for $[C_{31}H_{29}F_6N_5O_7S_3+H]^+$ 794.11.

Synthesis of 2-amino-4-ethoxythiophene-3-carbonitrile

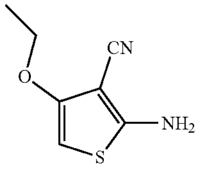

The mixture of $MeC(OMe)_3$ (2.26 mL, 12.3 mmol) and $CH_2(CN)_2$ (0.78 mL, 12.3 mmol) was stirred at 65° C. for 3 h before cooled down to rt. THF (10 mL) and sulfur (395 mg) was added followed by addition of $Et_3N$ (1.72 mL, 12.3 mmol) dropwise. The resulting reaction mixture was stirred at 60° C. for 15 min and concentrated under reduced pressure. The residue was partitioned between EtOAc and $H_2O$, extracted with EtOAc, dried over $Na_2SO_4$, filtered, and concentrated to dryness. The residue was triturated with DCM and filtered to give the title compound as a brown solid (1.23 g, 60%). $^1H$ NMR (400 MHz, $CD_3OD$) δ 5.27 (s, 1H), 3.99 (q, J=7.0 Hz, 2H), 1.38 (t, J=7.0 Hz, 3H); MS ESI $[M+H]^+$ 169.0, calcd for $[C_7H_8N_2OS+H]^+$ 169.0.

tert-Butyl 4-(5-amino-4-cyanothiophen-3-yl)piperazine-1-carboxylate

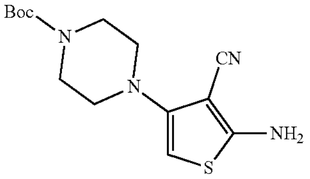 [SMILES: CC(C)(C)OC(=O)N1CCN(c2csc(N)c2C#N)CC1]

A mixture of $MeC(OMe)_3$ (1.3 mL, 10 mmol) and $CH_2(CN)_2$ (0.66 g, 10 mmol) was heated in closed vial at 80° C. for 17 h. The reaction was cooled to rt and tert-butyl piperazine-1-carboxylate (2.79 g, 15.0 mmol) was added. Heating with stirring was continued at 65° C. for 5 h. The reaction mixture was then concentrated in vacuo. $S_8$ (0.34 g) and anh THF (10 mL) were added. The suspension was heated with stirring at 40° C. $Et_3N$ (1.3 mL, 9.3 mmol) was added dropwise over 15 min. The oil bath temperature was increased to 60° C. and stirring was continued for 11 h. The reaction was then concentrated under reduced pressure and purified by flash chromatography ($SiO_2$, hexanes:EtOAc 5-50%) to afford tert-butyl 4-(5-amino-4-cyanothiophen-3-yl)piperazine-1-carboxylate as a light orange solid (0.71 g, 23%). $^1H$ NMR (400 MHz, DMSO-$d_6$) δ 7.12 (s, 2H), 5.46 (s, 1H), 3.45-3.37 (m, 4H), 2.90-2.81 (m, 4H), 1.40 (s, 9H). MS ESI $[M+H]^-$ 309.3, calcd for $[C_{14}H_{20}N_4O_2S+H]^+$ 309.1.

tert-butyl 4-(4-amino-5-(6-(4-methylpiperazin-1-yl)-1H-benzo[d]imidazol-2-yl)-6-oxo-6,7-dihydrothieno-[2,3-b]pyridin-3-yl)piperazine-1-carboxylate

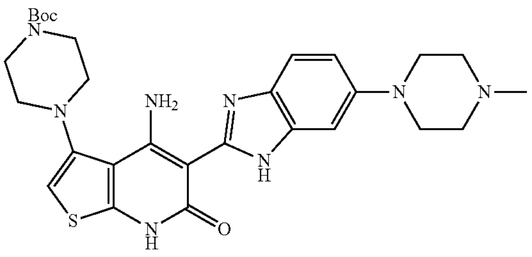 [SMILES: CN1CCN(c2ccc3nc(-c4c(N)c5c(N6CCN(C(=O)OC(C)(C)C)CC6)csc5[nH]c4=O)[nH]c3c2)CC1]

LiHMDS (1.0 M in THF, 2.8 mL, 2.8 mmol) was added dropwise at rt to a stirred suspension of ethyl 2-(6-(4-methylpiperazin-1-yl)-1H-benzo[d]imidazol-2-yl)acetate (0.170 g, 0.56 mmol) and tert-butyl 4-(5-amino-4-cyanothiophen-3-yl)piperazine-1-carboxylate (0.175 g, 0.56 mmol) in anh THF (10 mL) under Ar. The reaction was stirred at rt for additional 5 min and then heated in an oil bath at 40° C. for 1 h. The reaction was cooled to rt, quenched with satd aq $NH_4Cl$, concentrated under reduced pressure and purified by flash chromatography (MeOH/DCM 0-20%) to give the title compound as a light tan solid (83 mg, 26%). $^1H$ NMR (400 MHz, $CD_3OD$) δ 7.45 (d, J=8.8 Hz, 1H), 7.10 (d, J=2.3 Hz, 1H), 7.03 (dd, J=8.8, 2.3 Hz, 1H), 6.18 (s, 1H), 3.62-3.50 (m, 4H), 3.24-3.18 (m, 4H), 3.05-2.98 (m, 4H), 2.75-2.67 (m, 4H), 2.41 (s, 3H), 1.49 (s, 9H); MS ESI [M+H]- 565.3, calcd for $[C_{28}H_{36}N_8O_3S+H]^+$ 565.4.

ethyl 2-(6-(4-methylpiperazine-1-carbonyl)-1H-benzo[d]imidazol-2-yl)acetate

A. (3,4-Dinitrophenyl)(4-methylpiperazin-1-yl)methanone

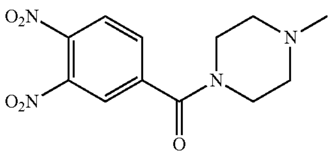 [SMILES: CN1CCN(C(=O)c2ccc([N+](=O)[O-])c([N+](=O)[O-])c2)CC1]

To a suspension of 3,4-dinitrobenzoic acid (1.23 g, 5.8 mmol) in anh DCM (20 mL) at rt was added dropwise oxalyl chloride (1.0 mL, 11.7 mmol) followed by anh DMF (2 drops). The reaction was stirred overnight and then concentrated at rt. The residue was dissolved in anh THF (40 mL) at 0° C. under Ar. 1-Methylpiperazine (1.3 mL, 11.7 mmol) was added dropwise (thick white suspension was stirred with intermittent shaking). After the addition the cooling was continued for 10 min before the cooling bath was removed. After stirring the reaction at rt for 3 h, $H_2O$ was added. THF was removed under reduced pressure and the aqueous residue was extracted ($CH_2Cl_2$; 2% MeOH in $CH_2Cl_2$. 2×). The combined organic extracts were dried over $Na_2SO_4$ and concentrated under reduced pressure to afford (3,4-dinitrophenyl)(4-methylpiperazin-1-yl) methanone as a light orange solid (1.77 g, quant). $^1H$ NMR (400 MHz, DMSO-$d_6$) δ 8.29 (d, J=8.3 Hz, 1H), 8.27 (d, J=1.5 Hz, 1H), 7.97 (dd, J=8.3, 1.8 Hz, 1H), 3.59-3.68 (m, 2H), 3.24-2.53 (m, 2H), 2.42-2.35 (m, 2H), 2.21-2.32 (m, 2H), 2.20 (s, 3H). MS ESI $[M+H]^-$ 295.2, calcd for $[C_{12}H_{14}N_4O_5+H]^+$ 295.1.

B. (3,4-Diaminophenyl)(4-methylpiperazin-1-yl)methanone

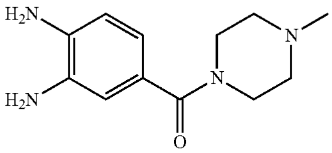 [SMILES: CN1CCN(C(=O)c2ccc(N)c(N)c2)CC1]

A solution of (3,4-dinitrophenyl)(4-methylpiperazin-1-yl) methanone (0.53 g, 1.8 mmol) in THF (25 mL) and EtOH (50 mL) was degassed with $N_2$. Pd/C (191 mg, 0.18 mmol) was added and the reaction was stirred under $H_2$ (1 atm) overnight at rt. The reaction mixture was then filtered through Celite and concentrated under reduced pressure to afford (3,4-diaminophenyl)(4-methylpiperazin-1-yl)methanone as a purple solid (0.44 g, quant). $^1H$ NMR (400 MHz, DMSO-$d_6$) δ 6.61-6.55 (m, 1H), 6.47-6.45 (m, 2H), 4.81 (br.s, 2H), 4.58 (br.s, 2H), 3.50-3.39 (m, 4H), 2.34-2.22 (m, 4H), 2.18 (s, 3H). MS ESI $[M+H]^+$ 235.1, calcd for $[C_{12}H_{18}N_4O+H]^+$ 235.1.

C. ethyl 2-(6-(4-methylpiperazine-1-carbonyl)-1H-benzo[d]imidazol-2-yl)acetate

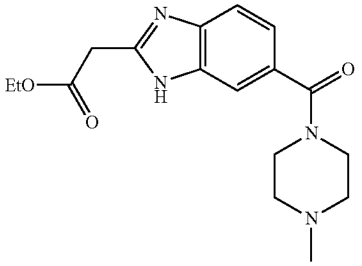 [SMILES: CCOC(=O)Cc1nc2ccc(C(=O)N3CCN(C)CC3)cc2[nH]1]

(3,4-Diaminophenyl)(4-methylpiperazin-1-yl) methanone (0.44 g, 1.8 mmol) and 3-ethoxy-3-iminopropanoic acid hydrochloride (1.07 g, 5.5 mmol) in anh EtOH (100 mL) under Ar were heated with stirring overnight at 65° C. The reaction mixture was then concentrated under reduced pressure. The residue was taken in to $H_2O$ (15 mL), neutralized with 10% aq $Na_2CO_3$, extracted with $CH_2Cl_2$ (2×), washed (brine) and dried over $Na_2SO_4$. Purification by flash chromatography (0-50% MeOH in $CH_2Cl_2$) afforded the title compound as a yellow foam (0.31 g, 52%). $^1H$ NMR (400 MHz, $CD_3OD$) δ 7.71-7.57 (m, 2H), 7.33 (d, J=8.2 Hz, 1H), 4.23 (q, J=7.2 Hz, 2H), 3.91-3.40 (m, 4H), 2.62-2.38 (m, 4H), 2.34 (s, 3H), 1.28 (t, J=7.1 Hz, 3H); Signals due to $CH_2$-ester are absent in $CD_3OD$. MS ESI $[M+H]^+$ 331.2, calcd for $[C_{17}H_{22}N_4O_3+H]^+$ 331.2.

ethyl 2-(6-(morpholine-4-carbonyl)-1H-benzo[d]imidazol-2-yl)acetate

A. (3,4-dinitrophenyl)(morpholino)methanone

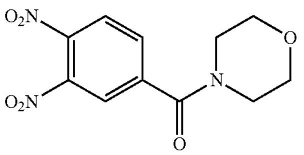 [SMILES: O=C(c1ccc([N+](=O)[O-])c([N+](=O)[O-])c1)N1CCOCC1]

To a suspension of 3,4-dinitrobenzoic acid (1.30 g, 6.1 mmol) in anh DCM (50 mL) at rt was added dropwise $(COCl)_2$ (1.0 mL, 11.7 mmol) followed by anh DMF (2 drops). The reaction was stirred overnight and then concentrated at rt. The residue was dissolved in anh THF (24 mL) at 0° C. under Ar. morpholine (1.0 mL, 11.6 mmol) was added dropwise (thick white suspension was stirred with intermittent shaking). After the addition the cooling was continued for 10 min before the cooling bath was removed. After stirring the reaction at rt for 3 h, $H_2O$ was added. THF was removed under reduced pressure and the aqueous residue was extracted ($CH_2Cl_2$. 2×). The combined organic extracts were dried ($Na_2SO_4$) and concentrated under reduced pressure to afford (3,4-dinitrophenyl)(morpholino) methanone as a light orange solid (1.8 g, quant). $^1H$ NMR (400 MHz, DMSO-$d_6$) δ 8.28-8.31 (m, 2H), 8.00 (dd, J=8.28, 1.76 Hz, 1H), 3.39-3.80 (m, 8H).

B. ethyl 2-(6-(morpholine-4-carbonyl)-1H-benzo[d]imidazol-2-yl)acetate

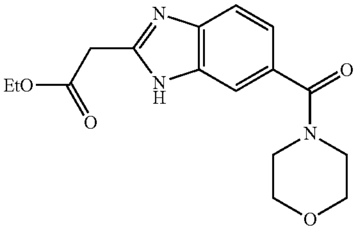 [SMILES: CCOC(=O)Cc1nc2ccc(C(=O)N3CCOCC3)cc2[nH]1]

A solution of (3,4-dinitropenyl)(morpholino)methanone (0.83 g, 2/9 mmol) in THF (30 mL) and EtOH (60 mL) was degassed with $N_2$. Pd/C (0.31 mg, 0.29 mmol) was added and the reaction was stirred under $H_2$ (1 atm) overnight at rt. The reaction mixture was then filtered through Celite and concentrated under reduced pressure to afford (3,4-diaminophenyl)(morpholino)methanone as a purple foam. LCMS (ESI) m/z calcd for $[C_{11}H_{15}N_3O_2+H]^+$ 222.1; found 222.2. The material and ethyl 3-ethoxy-3-iminopropanoate hydrochloride (1.2 g, 6.2 mmol) in anh EtOH (100 mL) under Ar were heated with stirring overnight at 65° C. The reaction mixture was then concentrated under reduced pressure. Purification by flash chromatography (0-20% MeOH in $CH_2Cl_2$) afforded the title compound as a pale red foam (0.43 g, 47%). $^1H$ NMR (400 MHz, $CD_3OD$) δ 7.52-7.76 (m, 2H), 7.33 (dd, J=8.28, 1.51 Hz, 1H), 4.22 (q, J=7.19 Hz, 2H), 4.00-4.05 (m, 2H), 3.70 (br.s., 8H), 1.28 (t, J=7.15 Hz, 3H); Signals due to $CH_2$-ester are absent in $CD_3OD$; MS ESI $[M+H]^-$ 318.2, calcd for $[C_{17}H_{22}N_4O_3+H]^+$ 318.1.

ethyl 2-(5-methyl-6-(4-methylpiperazin-1-yl)-1H-benzo[d]imidazol-2-yl)acetate A. 4-methyl-5-(4-methylpiperazin-1-yl)-2-nitroaniline

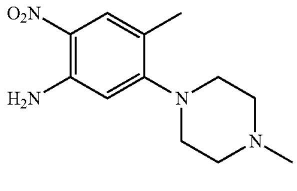 [SMILES: Cc1cc([N+](=O)[O-])c(N)cc1N1CCN(C)CC1]

5-Chloro-4-methyl-2-nitroaniline (0.32 g. 1/7 mmol) and 1-methylpiperazine (1.5 mL, 13.5 mmol) were heated in a sealed tube at 80° C. for 30 min followed by at 105° C. for 1 d and 120° C. for 2 d. The reaction was later cooled, diluted with $H_2O$ and filtered. The collected solid was rinsed with $H_2O$ and dried in vacuo to afford the title compound a as a yellow solid (0.36 g, 84%). $^1H$ NMR (400 MHz, DMSO-$d_6$) δ 7.72 (s, 1H), 7.27 (s, 2H), 6.44 (s, 1H), 2.97-2.86 (m 4H), 2.49-2.39 (m, 4H), 2.22 (s, 3H), 2.11 (s, 3H). LCMS (ESI) m/z calcd for $[C_{12}H18N_4O_2+H]^+$ 251.1; found 235.3.

B. ethyl 2-(5-methyl-6-(4-methylpiperazin-1-yl)-1H-benzo[d]imidazol-2-yl)acetate

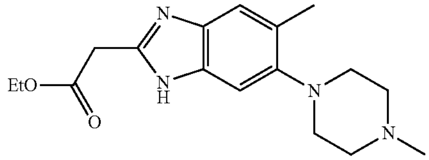 [SMILES: CCOC(=O)Cc1nc2cc(C)c(N3CCN(C)CC3)cc2[nH]1]

4-methyl-5-(4-methylpiperazin-1-yl)-2-nitroaniline (0.36 g, 1.4 mmol) and Pd/C (10%, 81 mg, 0.08 mmol) in EtOH (50 mL), THF (25 mL) were degassed with $N_2$ and then stirred under $H_2$ (1 atm) for 5 d. The reaction mix was filtered through Celite, the pad was rinsed with EtOH. The filtrate was concentrated under reduced pressure to afford 4-methyl-5-(4-methylpiperazin-1-yl)benzene-1,2-diamine as a yellow tan solid (0.35 g, quant). The material (0.35 g) and ethyl 3-ethoxy-3-iminopropanoate hydrochloride (0.81 g, 4.1 mmol) in anh EtOH (70 mL) under Ar were heated with stirring overnight at 65° C. The reaction mixture was then concentrated under reduced pressure, taken into $H_2O$ (20 mL) and basified with 2 M aq $Na_2CO_3$ to pH 9. The mixture was extracted with DCM (2×); the organic extracts were dried ($Na_2SO_4$) and concentrated under reduced pressure. Purification by flash chromatography (0-30% MeOH in $CH_2Cl_2$) afforded the title compound as a yellow foam (0.36 g, 82%). $^1H$ NMR (500 MHz, $CD_3OD$) δ 7.35 (s, 1H), 7.25 (s, 1H), 4.22 (q, J=7.09 Hz, 2H), 2.95-3.03 (m, 4H), 2.88-2.58 (m, 4H), 2.43 (s, 3H), 2.41 (s, 3H), 1.28 (t, J=7.09 Hz, 3H); Signals due to $CH_2$-ester are absent in $CD_3OD$; LCMS (ESI) m/z calcd for $[C_{17}H_{24}N_4O_2+H]^+$ 317.2; found 317.3.

Ethyl 2-(5-fluoro-6-morpholino-1H-benzo[d]imidazol-2-yl)acetate

A. 4-fluoro-5-morpholino-2-nitroaniline

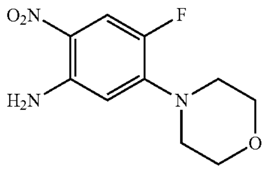 [SMILES: Nc1cc(N2CCOCC2)c(F)cc1[N+](=O)[O-]]

A mixture of 5-chloro-4-fluoro-2-nitroaniline (1.0 g, 5.24 mmol), morpholine (1.37 mL, 15.7 mmol) and DMSO (5 mL) was heated in oil bath 140° C. for 3 h. Then $H_2O$ (50 mL) was added with stirring at 80° C. to precipitate the product and allowed the suspension to rt, suction filtered, washed with $H_2O$ and dried to give the title compound as a yellow solid (1.25 g, 94%). $^1H$ NMR (400 MHz, $CD_3OD$) δ 7.17 (d, J=14.0 Hz, 1H), 6.37 (d, J=8.0 Hz, 1H), 3.83 (t, J=4.4 Hz, 4H), 3.22 (t, J=4.8 Hz, 4H); MS ESI $[M+H]^+$ 242.1, calcd for $[C_{10}H_{12}FN_3O_3+H]^-$ 242.1.

B. 4-fluoro-5-morpholinobenzene-1,2-diamine

To a 100 mL round-bottom flask was charged with 4-fluoro-5-morpholino-2-nitroaniline (1.23 g) and MeOH (37 mL) at rt under Ar blanket. Raney Nickel (0.123 g) was added under stirring with caution at rt. The reaction mass was slowly heated to 60-65° and hydrazine hydrate (0.86 mL) was added to the reaction mass dropwise in about 5 min. The reaction was

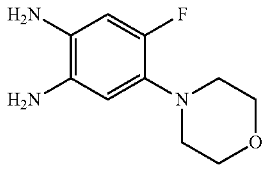 [SMILES: Nc1cc(F)c(N2CCOCC2)cc1N]

stirred at 65-70° C. for 2 hrs. After reaction completion, cooled it to rt and filtered the catalyst through a Celite pad under Ar and washed the Celite pad with MeOH (5 mL*2). The combined filtrate was concentrated and purified by flash chromatography (gradient: MeOH/DCM 0-25%) to give the title compound as a light brown solid (0.615 g, 57%). $^1$H NMR (400 MHz, $CD_3OD$) δ 6.51-6.47 (m, 2H), 3.81 (t, J=4.8 Hz, 4H), 2.93 (t, J=4.8 Hz, 4H); MS ESI $[M+h]^+$ 212.0, calcd for $[C_{10}H_{14}FN_3O+H]^+$ 212.1.

C. ethyl 2-(5-fluoro-6-morpholino-1H-benzo[d]imidazol-2-yl)acetate

To a solution of 4-fluoro-5-morpholinobenzene-1,2-diamine (0.615 g, 2.91 mmol) in EtOH (30 mL) at 65° C. was added ethyl 3-ethoxy-3-iminopropionate hydrochloride (1.14 g, 5.82

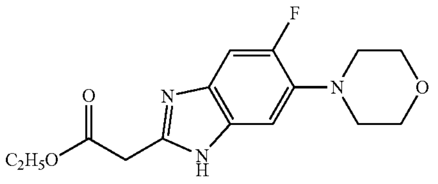

mmol) in two equal lots at an interval of 5 min each. Then stirred the reaction mass at 65° C. for 2 hrs. After reaction completion concentrate the reaction mass under reduced pressure to leaving behind thick brown oil. To the resulting oil $H_2O$ (25 mL) added and adjusted the pH ~10 using 2 M aq $Na_2CO_3$. The resultant mixture was extracted with DCM (30 mL*2) and the combined extracts were concentrated and purified by flash chromatography (gradient: Hex/EtOAc 0-40%, then MeOH/DCM 0-20%) to give the title compound as a brown solid (0.786 g, 88%). $^1$H NMR (400 MHz, $CD_3OD$) δ 7.26 (d, J=12.4 Hz, 1H), 7.19 (d, J=7.6 Hz, 1H), 4.25-4.20 (m, 2H), 3.88 (t, J=4.4 Hz, 4H), 3.08 (t, J=4.8 Hz, 4H), 1.28 (t, J=7.2 Hz, 3H); MS ESI $[M+H]^+$ 308.1.0, calcd for $[C_{15}H_{18}FN_3O_3+H]^+$ 308.1.

Ethyl 2-(6-(4-methyl-1,4-diazepan-1-yl)-1H-benzo[d]imidazol-2-yl)acetate

A. 5-(4-methyl-1,4-diazepan-1-yl)-2-nitroaniline

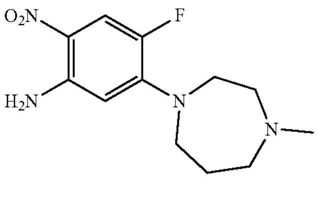

A mixture of 5-chloro-2-nitroaniline (8.63 g, 50 mmol), 1-methyl-1,4-diazepane (6.85 g, 60 mmol) and $K_2CO_3$ (8.28 g, 60 mmol) was heat at 90° C. for 20 h. After diluting with $H_2O$ (500 mL), it was extracted with EtOAc (60 mL×3), concentrated and dried to give crude 5-(4-methyl-1,4-diazepan-1-yl)-2-nitroaniline as a dark red oil (12.50 g). NMR indicated a mixture of product and 5-chloro-2-nitroaniline (2:1). $^1$H NMR (400 MHz, $CD_3OD$) δ 7.72 (d, J=10.0 Hz, 1H), 6.26 (dd, J=9.8, 2.6 Hz, 1H), 6.02 (d, J=2.4 Hz, 1H), 3.66-3.63 (m, 2H), 3.58 (t, J=6.4 Hz, 2H), 2.77-2.74 (m, 2H), 2.62-2.59 (m, 2H), 2.39 (s, 3H), 2.07-2.00 (m, 2H); MS ESI $[M+H]^+$ 251.3, calcd for $[C_{12}H_{18}N_4O_2+H]^+$ 251.15.

B. 4-(4-methyl-1,4-diazepan-1-yl)benzene-1,2-diamine

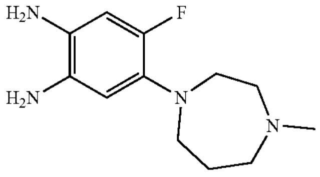 [SMILES: CN1CCCN(c2cc(N)c([N+](=O)[O-])cc2F)CC1]

To a mixture of crude 5-(4-methyl-1,4-diazepan-1-yl)-2-nitroaniline (12.50 g) and Raney-Nickel (1.25 g) in MeOH (150 mL) at 65° C. was added $N_2H_4$-$H_2O$ (12.0 mL) over 10 min. After addition, the resulting mixture was stirred at 70° C. for 30 min. Upon cooling to rt, it was filtered through Celite and rinsed with MeOH. The filtrate was concentrated and dried to give crude 4-(4-methyl-1,4-diazepan-1-yl)benzene-1,2-diamine as a dark red brown oil (10.57 g).

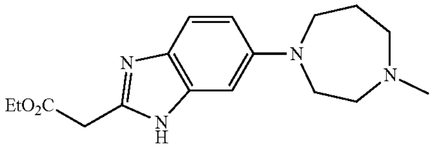 [SMILES: CCOC(=O)Cc1nc2ccc(N3CCCN(C)CC3)cc2[nH]1]

$^1$H NMR (400 MHz, $CD_3OD$) δ 6.63 (d, J=8.0 Hz, 1H), 6.53 (dd, J=8.4, 2.4 Hz, 1H), 6.26 (d, J=2.4 Hz, 1H), 3.60-3.40 (m, 4H), 2.75-2.71 (m, 2H), 2.62-2.58 (m, 2H), 2.37 (s, 3H), 2.04-1.97 (m, 2H).

C. Ethyl 2-(6-(4-methyl-1,4-diazepan-1-yl)-1H-benzo[d]imidazol-2-yl)acetate

A mixture of crude 4-(4-methyl-1,4-diazepan-1-yl)benzene-1,2-diamine (10.57 g) and ethyl 3-ethoxy-3-iminopropionate hydrochloride (19.50 g, 100 mmol) in EtOH (200 mL) was heated at 90° C. for 2 h. After removal of solvents, it was diluted with $H_2O$ (50 mL), basified with 2 M aq $Na_2CO_3$ (40 mL) and extracted with DCM (60 mL×3). The combined extracts were concentrated and purified by flash chromatography (gradient: 0-100% EtOAc/hexane, then MeOH/DCM 0-25%) to give the title compound as a dark brown oil (7.31 g, 46% over 3 steps). $^1$H NMR (400 MHz, $CD_3OD$) δ 8.38 (d, J=8.8 Hz, 1H), 6.82-6.77 (m, 2H), 4.22 (q, J=6.8 Hz, 2H), 3.66-3.61 (m, 2H), 3.54 (t, J=6.4 Hz, 2H), 2.85-2.80 (m, 2H), 2.68-2.64 (m, 2H), 2.41 (s, 3H), 2.12-2.05 (m, 2H), 1.29 (t, J=7.0 Hz, 3H); MS ESI $[M+H]^+$ 317.3, calcd for $[C_{17}H_{24}N_4O_2+H]^+$ 317.20.

Representative Examples

A1: 4-amino-5-(6-(4-methylpiperazin-1-yl)-1H-benzo[d]imidazol-2-yl)thieno[2,3-b]pyridin-6(7H)-one

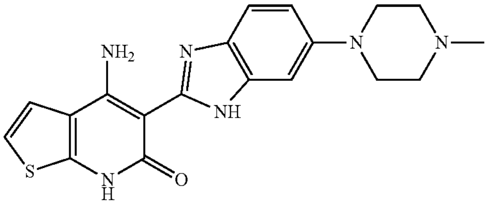 [SMILES: CN1CCN(c2ccc3nc(-c4c(N)c5ccsc5[nH]c4=O)[nH]c3c2)CC1]

To a solution of ethyl 2-(6-(4-methylpiperazin-1-yl)-1H-benzo[d]imidazol-2-yl)acetate (2.42 g, 8.05 mmol) and 2-aminothiophene-3-carbonitrile (1.0 g, 8.05 mmol) in anh THF (40 mL) at 40° C. added LDA (40 mL, 1 M in THF/hexane, 40 mmol) dropwise over 15 min under Ar. The resulting brown solution was stirred at 40° C. for 2 h and then quenched with aq $NH_4Cl$ (50 mL) at rt. The mixture was diluted with $H_2O$ (125 mL) and extracted with ethyl acetate (2×200 mL). The combined organic layers were washed once with $H_2O$, dried over $Na_2SO_4$, and concentrated to give crude product. The crude product was triturated with DCM (20 mL) followed by MeOH (25 mL) to give the title compound as a light brown solid (1.95 g, 64%).

The free base (1.95 g) was suspended in MeOH (50 mL) and added 1 M HCl-$Et_2O$ (13 mL) at rt. The suspension was stirred for 15 min at rt and concentrated under vacuum and azeotroped with MeOH (2×25 mL) to give the HCl salt as a dark brown solid (2.28 g, 62%); $^1H$ NMR (400 MHz, $CD_3OD$) δ 7.69 (d, J=9.2 Hz, 1H), 7.52 (d, J=5.6 Hz, 1H), 7.36 (dd, J=8.8, 2.4 Hz, 1H), 7.30 (d, J=2.4 Hz, 1H), 7.19 (d, J=5.6 Hz, 1H), 3.97-3.93 (m, 2H), 3.70-3.67 (m, 2H), 3.39-3.35 (m, 2H), 3.34-3.18 (m, 2H), 3.01 (s, 3H); MS ESI $[M+H]^+$ 381.2, calcd for $[C_{19}H_{20}N_6OS+H]^+$ 381.1.

| Example/IUPAC name | Structure | Yield; description; salt |
|---|---|---|
| A2: 4-amino-3-methyl-5-(6-(4-methylpiperazin-1-yl)-1H-benzo[d]imidazol-2-yl) thieno[2,3-b]pyridin-6(7H)-one | 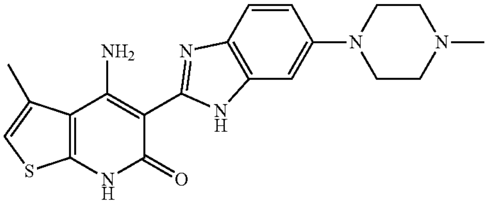 [SMILES: Cc1csc2[nH]c(=O)c(-c3nc4ccc(N5CCN(C)CC5)cc4[nH]3)c(N)c12] | 64 mg (38%); Grey solid 2HCl |
| | Reagents (general method A1): ethyl 2-(6-(4-methylpiperazin-1-yl)-1H-benzo[d]imidazol-2-yl)acetate (110 mg, 0.36 mmol), 2-amino-4-methylthiophene-3-carbonitrile (50 mg, 0.36 mmol), LDA (1.62 mL, 1M in THF/hexane, 1.62 mmol), anh THF (5.0 mL) $^1H$ NMR (400 MHz, $CD_3OD$) δ 7.72 (d, J = 9.2 Hz, 1H), 7.41 (dd, J = 8.8 Hz, 2.4 Hz, 1H), 7.33 (d, J = 2.0 Hz, 1H), 6.76 (d, J = 0.8 Hz, 1H), 3.98-3.94 (m, 2H), 3.70-3.67 (m, 2H), 3.38-3.35 (m, 2H), 3.27-3.21 (m, 2H), 3.00 (s, 3H), 2.30 (s, 3H); MS calcd; MS ESI $[M + H]^+$ 395.3, calcd for $[C_{20}H_{22}N_6OS + H]^+$ 395.1 | |
| A3: 4-amino-2-methyl-5-(6-(4-methylpiperazin-1-yl)-1H-benzo[d]imidazol-2-yl)thieno[2,3-b]pyridin-6(7H)-one | 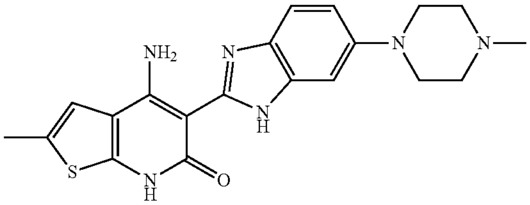 | 18 mg (10%); Light brown solid 2HCl |
| | Reagents (general method A1): ethyl 2-(6-(4-methylpiperazin-1-yl)-1H-benzo[d]imidazol-2-yl)acetate (110 mg, 0.36 mmol), 2-amino-5-methylthiophene-3-carbonitrile (50 mg, 0.36 mmol), LDA (1.80 mL, 1M in THF/hexane, 1.80 mmol), anh THF (5.0 mL) $^1H$ NMR (400 MHz, $CD_3OD$) δ 7.68 (d, J = 8.8 Hz, 1H), 7.38-7.31 (m, 2H), 7.18 (s, 1H), 3.96-3.93 (m, 2H), 3.70-3.67 (m, 2H), 3.40-3.34 (m, 2H), 3.25-3.19 (m, 2H), 3.01 (s, 3H), 2.52 (s, 3H); MS calcd; MS ESI $[M + H]^+$ 395.3, calcd for $[C_{20}H_{22}N_6OS + H]$+ 395.1 | |
| A4: 4-amino-5-(6-morpholino-1H-benzo[d]imidazol-2-yl)thieno[2,3-b]pyridin-6(7H)-one | 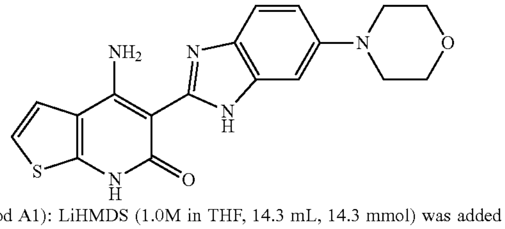 | 0.51 g (51%); Light tan solid; Free base |
| | Reagents (general method A1): LiHMDS (1.0M in THF, 14.3 mL, 14.3 mmol) was added dropwise over 20 min to a stirred solution of 2-aminothiophene-3-carbonitrile (0.340 g, 2.73 mmol), ethyl 2-(6-morpholino-1H-benzo[d]imidazol-2-yl)acetate (0.829 g, 2.86 mmol) in anh THF (20 mL) at rt under Ar. The reaction was heated at 40° C. for 1 h, then cooled to rt, quenched with satd aq $NH_4Cl$, concentrated under reduced pressure and purified by flash chromatography (MeOH—$CH_2Cl_2$ 0-7%). A small sample was repurified by prep HPLC to afford the TFA salt (a light yellow solid). $^1H$ NMR (400 MHz, DMSO-$d_6$) δ 12.18 (s, 1H), 7.59 (d, J = 5.7 Hz, 1H), 7.56 (br s, 1H), 7.36-7.24 (br. s, 1H), 7.20 (d, J = 5.7 Hz, 1H), 7.17-7.08 (m, 1H), 3.86-3.79 (m, 4H), 3.30-3.18 (m, 4H); three exchangeable protons may be attributed | |

-continued

| Example/IUPAC name | Structure | Yield; description; salt |
|---|---|---|
| | to two very broad peaks 13.47-12.46 (brs, 1H) and 9.30-7.67 (brs, 2H), MS ESI [M + H]$^+$ 368.2, calcd for [$C_{18}H_{17}N_5O_2S$ + H]$^+$ 368.1. | |
| A5: 4-amino-3-methoxy-5-(6-(4-methylpiperazin-1-yl)-1H-benzo[d]imidazol-2-yl)thieno[2,3-b]pyridin-6(7H)-one | 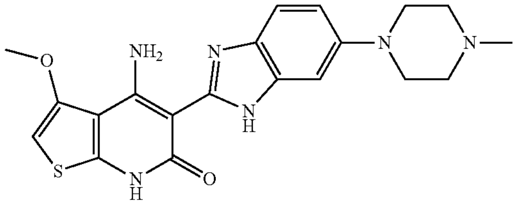 | 55 mg (11%); brown solid; TFA |
| | Reagents (General method A1): ethyl 2-(6-(4-methylpiperazin-1-yl)-1H-benzo[d]imidazol-2-yl)acetate (302 mg, 1 mmol), 2-amino-4-methoxythiophene-3-carbonitrile (154 mg, 1 mmol), LDA (1.0M in THF/hex, 5 mL, 5 mmol), THF (10 mL). $^1$H NMR (400 MHz, $CD_3OD$) δ 7.70 (d, J = 8.8 Hz, 1H), 7.39 (dd, J = 9.2, 2.4 Hz, 1H), 7.31 (d, J = 1.6 Hz, 1H), 6.09 (s, 1H), 3.98-3.88 (m, 2H), 3.85 (s, 3H), 3.72-3.64 (m, 2H), 3.38-3.28 (m, 2H), 3.25-3.14 (m, 2H), 2.87 (s, 3H); MS ESI [M + H]$^+$ 411.3, calcd for [$C_{20}H_{22}N_6O_2S$ + H]$^+$ 411.2. | |
| A6: 4-amino-3-ethoxy-5-(6-(4-methylpiperazin-1-yl)-1H-benzo[d]imidazol-2-yl)thieno[2,3-b]pyridin-6(7H)-one | 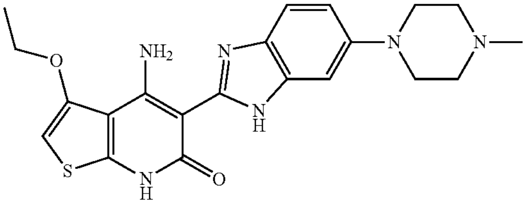 [SMILES: CCOc1csc2[nH]c(=O)c(-c3nc4ccc(N5CCN(C)CC5)cc4[nH]3)c(N)c12] | 200 mg (61%); dark brown solid; 2HCl salt |
| | Reagents (general method A1): 2-amino-4-ethoxythiophene-3-carbonitrile (111 mg, 0.66 mmol), ethyl 2-(6-(4-methylpiperazin-1-yl)-1H-benzo[d]imidazol-2-yl)acetate (200 mg, 0.66 mmol), LiHMDS (1M in THF, 2.65 mL, 2.65 mmol). $^1$H NMR (400 MHz, $CD_3OD$) δ 7.72 (d, J = 8.7 Hz, 1H), 7.42 (d, J = 8.4 Hz, 1H), 7.32 (s, 1 H), 6.08 (s, 1H), 4.08 (q, J = 6.8 Hz, 2H), 3.96 (d, J = 11.5 Hz, 2H), 3.68 (d, J = 11.8 Hz, 2H), 3.41-3.26 (m, 2H), 3.27-3.16 (m, 2H), 3.01 (s, 3H), 1.42 (t, J = 6.8 Hz, 3H); MS ESI [M + H]$^+$ 425.3, calcd for [$C_{21}H_{24}N_6O_2S$ + H]$^+$ 425.2. | |
| A7: 5-(6-(4-methylpiperazin-1-yl)-1H-benzo[d]imidazol-2-yl)-4-((tetrahydro-2H-pyran-4-yl)amino)thieno[2,3-b]pyridin-6(7H)-one | 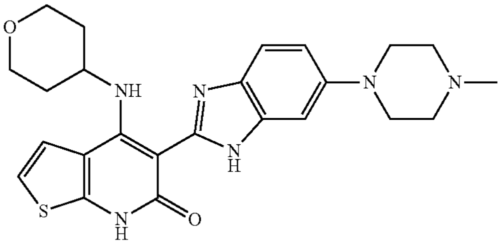 [SMILES: CN1CCN(c2ccc3nc(-c4c(NC5CCOCC5)c5ccsc5[nH]c4=O)[nH]c3c2)CC1] | 35 mg (43%); brown solid; TFA |
| | Step 1: Reagents (General method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.11 g, 0.14 mmol), tetrahydro-2H-pyran-4-amine (0.035 g, 0.35 mmol), DCM (15 mL). MS ESI [M + H]$^+$ 717.2, calcd for [$C_{33}H_{35}F_3N_6O_5S_2$ + H]$^+$ 717.21.<br>Step 2: Reagents (general method D): a mixture of 7-(4-methoxybenzyl)-5-(5 and/or 6-(4-methylpiperazin-1-yl)-1-((trifluoromethyl)sulfonyl)-1H-benzo[d]imidazol-2-yl)-4-((tetrahydro-2H-pyran-4-yl)amino)thieno[2,3-b]pyridin-6(7H)-one (0.10 g, 0.14 mmol), TFA (7 mL), and conc. HCl (1 mL). $^1$H NMR (400 MHz, $CD_3OD$) δ 7.65 (d, J = 9.0 Hz, 1H), 7.58 (d, J = 5.8 Hz, 1H), 7.29 (s, 2H), 7.19 (d, J = 6.0 Hz, 1H), 4.02-3.83 (m, 4H), 3.74-3.60 (m, 2H), 3.58-3.46 (m, 1H), 3.43-3.33 (m, 2H), 3.29-3.09 (m, 4H), 3.01 (s, 3H), 2.03-1.90 (m, 2H), 1.85-1.69 (m, 2H); MS ESI [M + H]$^+$ 465.3, calcd for [$C_{24}H_{28}N_6O_2S$ + H]$^+$ 465.2. | |
| A8: 4-(((1r,3r)-3-hydroxycyclobutyl)amino)-5-(6-(4-methylpiperazin-1-yl)-1H-benzo[d]imidazol-2-yl)thieno[2,3-b]pyridin-6(7H)-one | 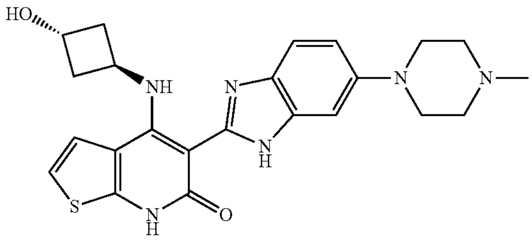 [SMILES: CN1CCN(c2ccc3nc(-c4c(N[C@H]5C[C@H](O)C5)c5ccsc5[nH]c4=O)[nH]c3c2)CC1] | 18 mg (16%); yellow solid; 2HCl |
| | Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.17 g, 0.22 mmol), (1r,3r)-3-aminocyclobutanol HCl salt (0.068 g, 0.55 mmol), DCM (10 mL). MS ESI [M + H]$^+$ 703.2, | |

-continued

| Example/IUPAC name | Structure | Yield; description; salt |
|---|---|---|
| calcd for $[C_{32}H_{33}F_3N_6O_5S_2 + H]^+$ 703.19. Step 2: Reagents (General method D): a mixture of 4-(((1r,3r)-3-hydroxycyclobutyl)amino)-7-(4-methoxybenzyl)-5-(5 and/or 6-(4-methylpiperazin-1-yl)-1-((trifluoromethyl)sulfonyl)-1H-benzo[d]-imidazol-2-yl)thieno[2,3-b]pyridin-6(7H)-one (0.16 g, 0.22 mmol), TFA (7 mL), and conc. HCl (1 mL). $^1H$ NMR (400 MHz, $CD_3OD$) δ 7.69 (d, J = 9.3 Hz, 1H), 7.61 (d, J = 6.0 Hz, 1H), 7.37 (dd, J = 9.0, 2.5 Hz, 1H), 7.34-7.29 (m, 1H), 7.20 (d, J = 6.0 Hz, 1H), 4.45-4.33 (m, 1H), 4.03-3.90 (m, 3H), 3.76-3.61 (m, 2H), 3.42-3.36 (m, 2H), 3.30-3.18 (m, 2H), 3.01 (s, 3H), 2.54-2.42 (m, 2H), 2.14-2.03 (m, 2 H); MS ESI [M + H]$^+$ 451.3, calcd for $[C_{23}H_{26}N_6O_2S + H]^+$ 451.2. | | |
| A9: 4-(((1R*,3R*)-3-hydroxycyclopentyl)amino)-5-(6-(4-methylpiperazin-1-yl)-1H-benzo[d]imidazol-2-yl)thieno[2,3-b]pyridin-6(7H)-one | 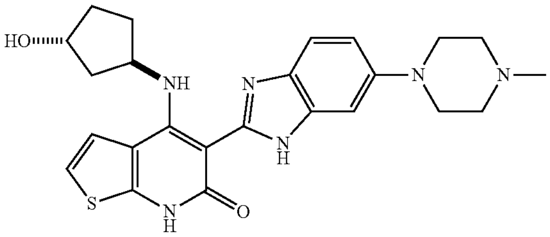 | 15 mg (11%); yellow solid; 2HCl |
| Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.17 g, 0.22 mmol), (1R*,3R*)-3-aminocyclopentanol HCl salt (0.076 g, 0.55 mmol), DCM (10 mL). MS ESI [M + H]$^+$ 717.2, calcd for $[C_{33}H_{35}F_3N_6O_5S_2 + H]^+$ 717.21. Step 2: Reagents (general method D): a mixture of 4-(((1R*,3R*)-3-hydroxycyclopentyl)amino)-7-(4-methoxybenzyl)-5-(5 and/or 6-(4-methylpiperazin-1-yl)-1-((trifluoromethyl)sulfonyl)-1H-benzo[d]-imidazol-2-yl)thieno[2,3-b]pyridin-6(7H)-one (0.16 g, 0.22 mmol), TFA (7 mL), and conc. HCl (1 mL). $^1H$ NMR (400 MHz, $CD_3OD$) δ 7.68 (d, J = 8.8 Hz, 1H), 7.67 (d, J = 6.0 Hz, 1H), 7.39 (dd, J = 8.8, 2.3 Hz, 1H), 7.32 (d, J = 2.0 Hz, 1H), 7.20 (d, J = 5.8 Hz, 1H), 4.32-4.24 (m, 1H), 4.01-3.91 (m, 2H), 3.86-3.75 (m, 1H), 3.73-3.64 (m, 2H), 3.41-3.36 (m, 2H), 3.30-3.19 (m, 2H), 3.01 (s, 3H), 2.06-1.94 (m, 2H), 1.91-1.84 (m, 2H), 1.74-1.62 (m, 1H), 1.47-1.40 (m, 1H); MS ESI [M + H]$^+$ 465.2, calcd for $[C_{24}H_{28}N_6O_2S + H]^+$ 465.2. | | |
| A10: (R)-5-(6-(4-methylpiperazin-1-yl)-1H-benzo[d]imidazol-2-yl)-4-((tetrahydrofuran-3-yl)amino)thieno[2,3-b]pyridin-6(7H)-one | 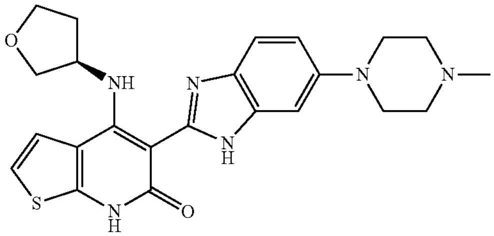 [SMILES: CN1CCN(c2ccc3nc(-c4c(N[C@@H]5CCOC5)c5ccsc5[nH]c4=O)[nH]c3c2)CC1] | 87 mg (53%); yellow solid; TFA |
| Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.23 g, 0.30 mmol), (R)-tetrahydrofuran-3-amine (0.11 g, 0.90 mmol), DCM (12 mL). MS ESI [M + H]$^+$ 703.2, calcd for $[C_{32}H_{33}F_3N_6O_5S_2 + H]^+$ 703.19. Step 2: Reagents (general method D): a mixture of (R)-7-(4-methoxybenzyl)-5-(5 and/or 6-(4-methylpiperazin-1-yl)-1-((trifluoromethyl)sulfonyl)-1H-benzo[d]imidazol-2-yl)-4-((tetrahydrofuran-3-yl)amino)thieno[2,3-b]pyridin-6(7H)-one (0.21 g, 0.30 mmol), TFA (7 mL), and conc. HCl (1 mL). $^1H$ NMR (400 MHz, $CD_3OD$) δ 7.61 (d, J = 8.8 Hz, 1H), 7.59 (d, J = 6.0 Hz, 1H), 7.28-7.22 (m, 2H), 7.17 (d, J = 5.8 Hz, 1H), 4.30-4.22 (m, 1H), 4.05-3.97 (m, 1H), 3.92-3.75 (m, 5H), 3.65 (br. s., 2H), 3.38-3.26 (m, 2H), 3.24-3.08 (m, 2H), 3.00 (s, 3H), 2.28-2.16 (m, 1H), 2.14-2.05 (m, 1H); MS ESI [M + H]$^+$ 451.2, calcd for $[C_{23}H_{26}N_6O_2S + H]^+$ 451.2. | | |
| A11: (S)-5-(6-(4-methylpiperazin-1-yl)-1H-benzo[d]imidazol-2-yl)-4-((tetrahydrofuran-3-yl)amino)thieno[2,3-b]pyridin-6(7H)-one | 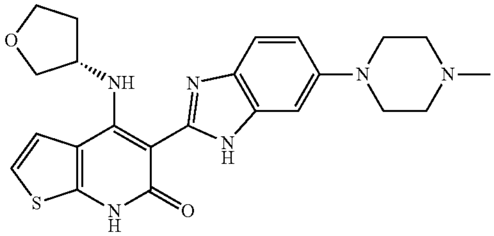 [SMILES: CN1CCN(c2ccc3nc(-c4c(N[C@H]5CCOC5)c5ccsc5[nH]c4=O)[nH]c3c2)CC1] | 61 mg (36%); brown solid; TFA |
| Step 1: Reagents (general method C): a mixture of 7-(4-methoxybenzyl)-5-(5 and/or 6-(4-methylpiperazin-1-yl)-1-((trifluoromethyl)sulfonyl)-1H-benzo[d]imidazol-2-yl)-6-oxo-6,7-dihydro-thieno[2,3-b]pyridin-4-yl trifluoromethanesulfonate (0.23 g, 0.30 mmol), (S)- | | |

-continued

| Example/IUPAC name | Structure | Yield; description; salt |
|---|---|---|
| | tetrahydrofuran-3-amine (0.11 g, 0.90 mmol), DCM (12 mL). MS ESI [M + H]$^+$ 703.2, calcd for [$C_{32}H_{33}F_3N_6O_5S_2$ + H]$^+$ 703.19. Step 2: Reagents (general method D): a mixture of (S)-7-(4-methoxybenzyl)-5-(5 and/or 6-(4-methylpiperazin-1-yl)-1-((trifluoromethyl)sulfonyl)-1H-benzo[d]imidazol-2-yl)-4-((tetrahydrofuran-3-yl)amino)thieno[2,3-b]pyridin-6(7H)-one (0.21 g, 0.30 mmol), TFA (7 mL), and conc. HCl (1 mL). $^1$H NMR (400 MHz, $CD_3OD$) δ 7.63 (d, J = 8.8 Hz, 1H), 7.61 (d, J = 5.8 Hz, 1H), 7.29-7.23 (m, 2H), 7.19 (d, J = 5.8 Hz, 1H), 4.33-4.22 (m, 1H), 4.06-3.97 (m, 1H), 3.95-3.76 (m, 5H), 3.66 (br. s., 2H), 3.41-3.32 (m, 2H), 3.24-3.08 (m, 2H), 3.01 (s, 3H), 2.29-2.16 (m, 1H), 2.14-2.02 (m, 1H); MS ESI [M + H]$^+$ 451.2, calcd for [$C_{23}H_{26}N_6O_2S$ + H]$^+$ 451.18. | |
| A12: 4-(((1s,3s)-3-hydroxycyclobutyl)amino)-5-(6-(4-methylpiperazin-1-yl)-1H-benzo[d]imidazol-2-yl)thieno[2,3-b]pyridin-6(7H)-one | 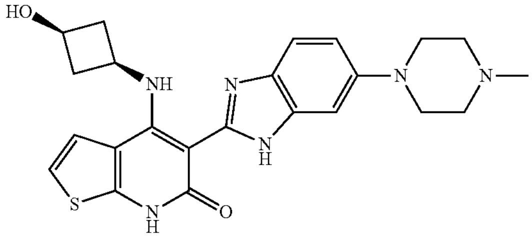 [SMILES: CN1CCN(c2ccc3nc(-c4c(N[C@H]5C[C@@H](O)C5)c5ccsc5[nH]c4=O)[nH]c3c2)CC1] | 101 mg (60%); yellow solid; TFA |
| | Step 1: Reagents (general method C): a mixture of 7-(4-methoxybenzyl)-5-(5 and/or 6-(4-methylpiperazin-1-yl)-1-((trifluoromethyl)sulfonyl)-1H-benzo[d]imidazol-2-yl)-6-oxo-6,7-dihydro-thieno[2,3-b]pyridin-4-yl trifluoromethanesulfonate (0.23 g, 0.30 mmol), (1s,3s)-3-aminocyclobutanol HCl salt (0.11 g, 0.90 mmol), DMF (8 mL). MS ESI [M + H]$^+$ 703.1, calcd for [$C_{32}H_{33}F_3N_6O_5S_2$ + H]$^+$ 703.19. Step 2: Reagents (general method D): a mixture of 4-(((1s,3s)-3-hydroxycyclobutyl)amino)-7-(4-methoxybenzyl)-5-(5 and/or 6-(4-methylpiperazin-1-yl)-1-((trifluoromethyl)sulfonyl)-1H-benzo[d]-imidazol-2-yl)thieno[2,3-b]pyridin-6(7H)-one (0.21 g, 0.30 mmol), TFA (7 mL), and conc. HCl (1 mL). $^1$H NMR (400 MHz, $CD_3OD$) δ 7.62 (d, J = 9.5 Hz, 1H), 7.57 (d, J = 6.0 Hz, 1H), 7.30-7.21 (m, 2H), 7.16 (d, J = 6.0 Hz, 1H), 3.97-3.79 (m, 3H), 3.73-3.50 (m, 3H), 3.40-3.26 (m, 2H), 3.17 (m, 2H), 3.00 (s, 3H), 2.69-2.56 (m, 2H), 2.16-2.00 (m, 2H); MS ESI [M + H]$^+$ 451.2, calcd for [$C_{23}H_{26}N_6O_2S$ + H]$^+$ 451.2. | |
| A13: 4-(((1R*,3S*)-3-hydroxycyclopentyl)amino)-5-(6-(4-methylpiperazin-1-yl)-1H-benzo[d]imidazol-2-yl)thieno[2,3-b]pyridin-6(7H)-one | 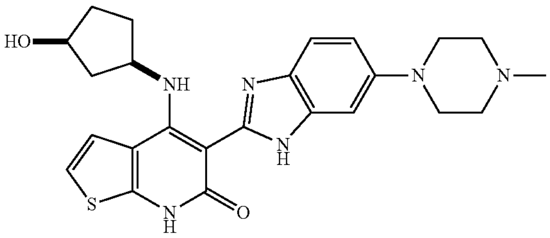 | 96 mg (57%); yellow solid; TFA |
| | Step 1: Reagents (general method C): a mixture of 7-(4-methoxybenzyl)-5-(5 and/or 6-(4-methylpiperazin-1-yl)-1-((trifluoromethyl)sulfonyl)-1H-benzo[d]imidazol-2-yl)-6-oxo-6,7-dihydro-thieno[2,3-b]pyridin-4-yl (0.23 g, 0.30 mmol), (1S*,3R*)-3-aminocyclopentanol HCl salt (0.12 g, 0.90 mmol), DMF (8 mL). MS ESI [M + H]$^+$ 717.2, calcd for [$C_{33}H_{35}F_3N_6O_5S_2$ + H]$^+$ 717.21. Step 2: Reagents (general method D): a mixture of 4-(((1R*,3S*)-3-hydroxycyclopentyl)amino)-7-(4-methoxybenzyl)-5-(5 and/or 6-(4-methylpiperazin-1-yl)-1-((trifluoromethyl)sulfonyl)-1H-benzo[d]-imidazol-2-yl)thieno[2,3-b]pyridin-6(7H)-one (0.21 g, 0.30 mmol), TFA (7 mL), and conc. HCl (1 mL). $^1$H NMR (400 MHz, $CD_3OD$) δ 7.62 (d, J = 9.0 Hz, 1H), 7.53 (d, J = 5.8 Hz, 1H), 7.28 (dd, J = 2.1, 8.9 Hz, 1H), 7.24 (d, J = 1.8 Hz, 1H), 7.19 (d, J = 5.8 Hz, 1H), 4.47-4.39 (m, 1H), 4.23-4.12 (m, 1H), 3.96-3.81 (m, 2H), 3.73-3.60 (m, 2H), 3.39-3.26 (m, 2H), 3.25-3.11 (m, 2H), 3.00 (s, 3H), 2.09-1.82 (m, 6H); MS ESI [M + H]$^+$ 465.2, calcd for [$C_{24}H_{28}N_6O_2S$ + H]$^+$ 465.2. | |
| A14: 4-(((3R,4R)-3-fluoropiperidin-4-yl)amino)-5-(6-(4-methylpiperazin-1-yl)-1H-benzo[d]imidazol-2-yl)thieno[2,3-b]pyridin-6(7H)-one | 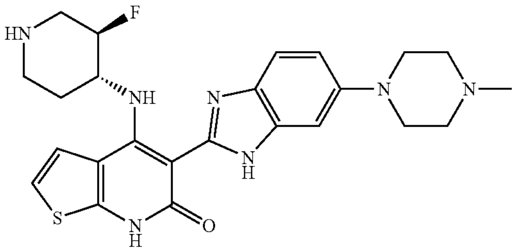 [SMILES: CN1CCN(c2ccc3nc(-c4c(N[C@@H]5CCNC[C@H]5F)c5ccsc5[nH]c4=O)[nH]c3c2)CC1] | 126 mg (58%); orange solid; 2 TFA |
| | Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.24 g, 0.31 mmol), (3R,4R)-tert-butyl 4-amino-3-fluoropiperidine-1-carboxylate (0.20 g, 0.93 mmol), DMF (5 mL). MS ESI | |

-continued

| Example/IUPAC name | Structure | Yield; description; salt |
|---|---|---|
| | [M − $CF_3O_2S$ + 2H]$^+$ 702.2, calcd for [$C_{37}H_{44}FN_7O_4S$ + H]$^+$ 702.3. Step 2: Reagents (general method D): a mixture of (3R,4R)-tert-butyl 3-fluoro-4-((7-(4-methoxybenzyl)-5-(5 and/or 6-(4-methylpiperazin-1-yl)-1-((trifluoromethyl)sulfonyl)-1H-benzo[d]-imidazol-2-yl)-6-oxo-6,7-dihydrothieno[2,3-b]pyridin-4-yl)amino)piperidine-1-carboxylate (0.26 g, 0.31 mmol), TFA (7 mL), and conc. HCl (1 mL). $^1$H NMR (400 MHz, $CD_3OD$) δ 7.57 (d, J = 8.8 Hz, 1H), 7.51 (d, J = 6.0 Hz, 1H), 7.23 (d, J = 1.8 Hz, 1H), 7.19 (d, J = 6.0 Hz, 1H), 7.15 (dd, J = 1.8, 8.8 Hz, 1H), 5.13-4.87 (m, 2H), 4.33-4.21 (m, 1H), 3.94-3.50 (m, 6H), 3.44-3.34 (m, 2H), 3.28-3.07 (m, 3H), 3.00 (s, 3H), 2.49-2.37 (m, 1H), 2.19-2.05 (m, 1H); MS ESI [M + H]$^+$ 482.2, calcd for [$C_{24}H_{28}FN_7OS$ + H]$^+$ 482.2. | |
| A15: 4-((3,3-difluoropiperidin-4-yl)amino)-5-(6-(4-methylpiperazin-1-yl)-1H-benzo[d]imidazol-2-yl)thieno[2,3-b]pyridin-6(7H)-one | 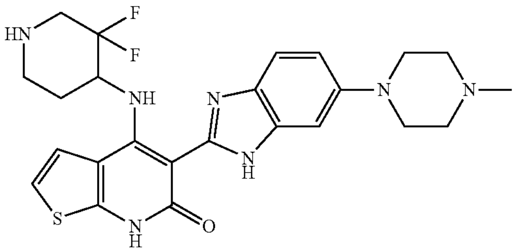 [SMILES: CN1CCN(c2ccc3nc(-c4c(NC5CCNCC5(F)F)c5ccsc5[nH]c4=O)[nH]c3c2)CC1] | 134 mg (59%); yellow solid; 2 TFA |
| | Step 1: Reagents (general method C): A mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.24 g, 0.31 mmol), tert-butyl 4-amino-3,3-difluoropiperidine-1-carboxylate (0.22 g, 0.93 mmol), DMF (5 mL). MS ESI [M − $CF_3O_2S$ + H]$^+$ 719.2, calcd for [$C_{37}H_{43}F_2N_7O_4S$]$^+$ 719.31. Step 2: Reagents (general method D): a mixture of tert-butyl 3,3-difluoro-4-((7-(4-methoxybenzyl)-5-(5 and/or 6-(4-methylpiperazin-1-yl)-1-((trifluoromethyl)sulfonyl)-1H-benzo[d]imidazol-2-yl)-6-oxo-6,7-dihydrothieno[2,3-b]pyridin-4-yl)amino)piperidine-1-carboxylate (0.26 g, 0.31 mmol), TFA (7 mL), and conc. HCl (1 mL). $^1$H NMR (400 MHz, $CD_3OD$) δ 7.60-7.50 (m, 2H), 7.26-7.17 (m, 2H), 7.13 (dd, J = 1.8, 9.0 Hz, 1H), 4.65-4.48 (m, 1H), 3.96-3.45 (m, 8H), 3.29-3.04 (m, 4H), 2.98 (s, 3H), 2.59-2.41 (m, 1H), 2.40-2.22 (m, 1H); MS ESI [M + H]$^+$ 500.2, calcd for [$C_{24}H_{27}F_2N_7OS$ + H]$^+$ 500.2. | |
| A16: (R)-4-((1-hydroxy-3-methylbutan-2-yl)amino)-5-(6-(4-methylpiperazin-1-yl)-1H-benzo[d]imidazol-2-yl)thieno[2,3-b]pyridin-6(7H)-one | 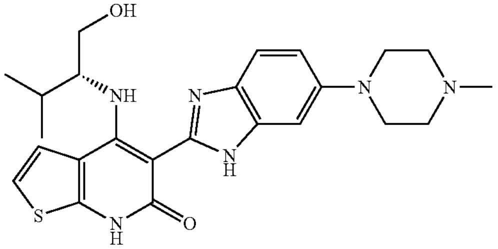 [SMILES: CC(C)[C@H](CO)Nc1c(-c2nc3ccc(N4CCN(C)CC4)cc3[nH]2)c(=O)[nH]c2sccc12] | 40 mg (29%), yellow solid; free base |
| | Step 1: Reagents (general method C): 7-(4-methoxybenzyl)-5-(5 and/or 6-(4-methylpiperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (crude, 0.30 mmol), (R)-2-amino-3-methylbutan-1-ol (0.12 g, 1.2 mmol), DMF (7 mL). ESI [M + H]$^+$ 719.2, calcd for [$C_{33}H_{37}F_3N_6O_5S_2$ + H]$^+$ 719.2 Step 2: Reagents (general method D): (R)-4-((1-hydroxy-3-methylbutan-2-yl)amino)-7-(4-methoxybenzyl)-5-(5 and/or 6-(4-methylpiperazin-1-yl)-1-((trifluoromethyl)sulfonyl)-1H-benzo[d]-imidazol-2-yl)thieno[2,3-b]pyridin-6(7H)-one (crude, 0.30 mmol), TFA (5 mL), HCl (1 mL). $^1$H NMR (400 MHz, $CD_3OD$) δ 7.65 (d, J = 6.0 Hz, 1H), 7.47-7.42 (m, 1H), 7.19-7.13 (m, 1H), 7.10 (d, J = 5.7 Hz, 1H), 7.02-6.94 (m, 1H), 4.27-4.19 (m, 1H), 3.92-3.82 (m, 2H), 3.21 (br s, 4H), 2.69 (br s, 4H), 2.38 (s, 3H), 2.32-2.22 (m, 1H), 1.23 (d, J = 7.0 Hz, 3H), 1.02 (d, J = 7.0 Hz, 3H); ESI [M + H]$^+$ 467.3, calcd for [$C_{24}H_{30}N_6O_2S$ + H]$^+$ 467.2 | |
| A17: 4-((5-(6-(4-methylpiperazin-1-yl)-1H-benzo[d]imidazol-2-yl)-6-oxo-6,7-dihydrothieno[2,3-b]pyridin-4-yl)amino)piperidine-1-carbaldehyde | 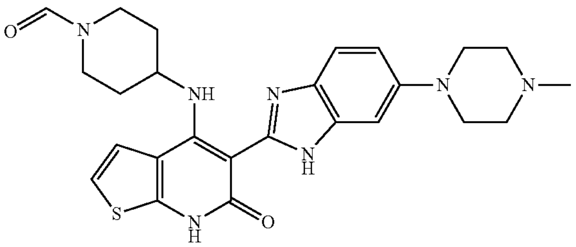 [SMILES: CN1CCN(c2ccc3nc(-c4c(NC5CCN(C=O)CC5)c5ccsc5[nH]c4=O)[nH]c3c2)CC1] | 40 mg (27%), Yellow solid; Free base |
| | Step 1: Reagents (general method C): 7-(4-methoxybenzyl)-5-(5 and/or 6-(4-methylpiperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (crude, 0.30 mmol), 4-aminopiperidine-1-carbaldehyde (0.15 g, 1.2 mmol), DMF (7 mL). ESI [M + H]$^+$ 744.1, calcd for [$C_{34}H_{36}F_3N_7O_5S_2$ + H]$^+$ 744.2 Step 2: Reagents (general method D): 4-((7-(4-methoxybenzyl)-5-(5 and/or 6-(4- | |

-continued

| Example/IUPAC name | Structure | Yield; description; salt |
|---|---|---|
| | methylpiperazin-1-yl)-1-((trifluoromethyl)sulfonyl)-1H-benzo[d]imidazol-2-yl)-6-oxo-6,7-dihydrothieno[2,3-b]pyridin-4-yl)amino)piperidine-1-carbaldehyde (crude, 0.30 mmol), TFA (5 mL), HCl (1 mL). $^1$H NMR (400 MHz, $CD_3OD$) δ 8.06 (s, 1H), 7.45 (s, 2H), 7.18-7.06 (m, 2H), 7.00-6.91 (m, 1H), 4.52-4.40 (m, 1H), 4.09-3.95 (m, 1H), 3.84-3.73 (m, 1H), 3.52-3.38 (m, 2H), 3.20 (br s, 4H), 2.66 (br s, 4H), 2.36 (s, 3H), 2.14 (br s, 2H), 1.91-1.69 (m, 2H); ESI $[M + H]^+$ 492.2, calcd for $[C_{25}H_{29}N_7O_2S + H]^+$ 492.2 | |
| A18: 4-((1-methylpiperidin-4-yl)amino)-5-(6-morpholino-1H-benzo[d]imidazol-2-yl)thieno[2,3-b]pyridin-6(7H)-one | 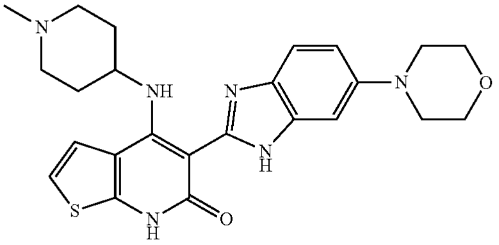 [SMILES: CN1CCC(Nc2c(-c3nc4ccc(N5CCOCC5)cc4[nH]3)c(=O)[nH]c3sccc23)CC1] | 15 mg (8%), yellow solid; Free base |
| | Step 1: Reagents: (general method C): 7-(4-methoxybenzyl)-5-(5 and/or 6-morpholino-1-((trifluoro-methyl)sulfonyl)-1H-benzo[d]imidazol-2-yl)-6-oxo-6,7-dihydrothieno[2,3-b]pyridin-4-yl trifluoro-methanesulfonate (crude, 0.41 mmol), tert-butyl 4-aminopiperidine-1-carboxylate (0.19 g, 1.6 mmol), DMF (7 mL). ESI $[M + H]^+$ 717.1, calcd for $[C_{33}H_{35}F_3N_6O_5S_2 + H]^+$ 717.2<br>Step 2: Reagents (general method D): 7-(4-methoxybenzyl)-4-((1-methylpiperidin-4-yl)amino)-5-(5 and/or 6-morpholino-1-((trifluoromethyl)sulfonyl)-1H-benzo[d]imidazol-2-yl)thieno[2,3-b]pyridin-6(7H)-one (crude, 0.30 mmol), TFA (5 mL), HCl (1 mL). $^1$H NMR (400 MHz, $CD_3OD$) δ 7.52-7.43 (m, 2H), 7.19-7.10 (m, 2H), 7.03-6.95 (m, 1H), 4.38-4.23 (m, 1H), 3.92-3.82 (m, 4H), 3.19-3.10 (m, 4H), 2.98-2.87 (m, 2H), 2.59-2.44 (m, 2H), 2.38 (s, 3H), 2.26-2.14 (m, 2H), 2.00-1.87 (m, 2H); ESI $[M + H]^+$ 465.2, calcd for $[C_{24}H_{28}N_6O_2S + H]^+$ 465.2 | |
| A19: 4-(cyclopentylamino)-3-methyl-5-(6-(4-methylpiperazin-1-yl)-1H-benzo[d]imidazol-2-yl)thieno[2,3-b]pyridin-6(7H)-one | 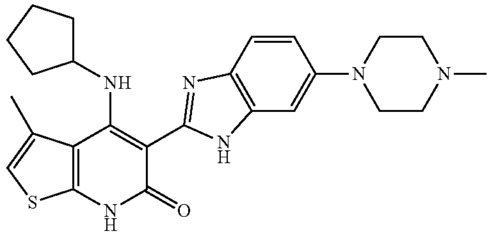 [SMILES: Cc1csc2[nH]c(=O)c(-c3nc4ccc(N5CCN(C)CC5)cc4[nH]3)c(NC3CCCC3)c12] | 59 mg (36%); Yellow solid 2HCl |
| | Step-01: Reagents (general method C): 7-(4-methoxybenzyl)-3-methyl-5-(5 and/or 6-(4-methylpipera-zin-1-yl)-1-((trifluoromethyl)sulfonyl)-1H-benzo[d]imidazol-2-yl)-6-oxo-6,7-dihydrothieno[2,3-b]py-ridin-4-yl trifluoromethanesulfonate (242 mg, 0.31 mmol), cyclopentylamine (80 mg, 0.93 mmol), DMF (4 mL); MS calcd; MS ESI $[M + H]^+$ 715.2, calcd for $[C_{34}H_{37}F_3N_6O_4S_2 + H]^+$ 715.2<br>Step-02: Reagents (general method D): 4-(cyclopentylamino)-7-(4-methoxybenzyl)-3-methyl-5-(5 and/or 6-(4-methylpiperazin-1-yl)-1-((trifluoromethyl)sulfonyl)-1H-benzo[d]imidazol-2-yl)thieno[2,3-b]pyridin-6(7H)-one (245 mg), TFA (6 mL), conc, HCl (1 mL). $^1$H NMR (400 MHz, $CD_3OD$) δ 7.72 (d, J = 9.2 Hz, 1H), 7.44-7.41 (m, 1H), 7.32 (d, J = 1.6 Hz, 1H), 6.86 (s, 1H), 3.99-3.96 (m, 2H), 3.71-3.68 (m, 2H), 3.40-3.34 (m, 2H), 3.28-3.23 (m, 2H), 3.18-3.15 (m, 1H), 3.01 (s, 3H), 2.65 (s, 3H), 1.68-1.61 (m, 6H), 1.46-1.44 (m, 2H); MS ESI $[M + H]^+$ 463.2, calcd for $[C_{25}H_{30}N_6OS + H]^+$ 463.2 | |
| A20: 3-methyl-5-(6-(4-methylpiperazin-1-yl)-1H-benzo[d]imidazol-2-yl)-4-((tetrahydro-2H-pyran-4-yl)amino)thieno[2,3-b]pyridin-6(7H)-one | 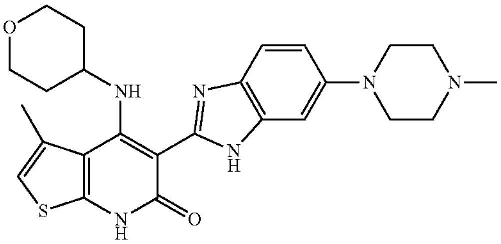 [SMILES: Cc1csc2[nH]c(=O)c(-c3nc4ccc(N5CCN(C)CC5)cc4[nH]3)c(NC3CCOCC3)c12] | 60 mg (35%); Yellow solid 2HCl |
| | Step-01: Reagents (general method C): 7-(4-methoxybenzyl)-3-methyl-5-(5 and/or 6-(4-methy-lpiperazin-1-yl)-1-((trifluoromethyl)sulfonyl)-1H-benzo[d]imidazol-2-yl)-6-oxo-6,7-dihydrothieno-[2,3-b]pyridin-4-yl trifluoromethanesulfonate (242 mg, 0.31 mmol), tetrahydro-2H-pyran-4-amine (95 mg, 0.93 mmol), DMF (4 mL). MS calcd; MS ESI $[M + H]^+$ 731.2, calcd for $[C_{34}H_{37}F_3N_6O_5S_2 + H]^+$ 731.2<br>Step-02: Reagents (general method D): 7-(4-methoxybenzyl)-3-methyl-5-(5 and/or 6-(4-methyl-piperazin-1-yl)-1-((trifluoromethyl)sulfonyl)-1H-benzo[d]imidazol-2-yl)-4-((tetrahydro-2H-pyran-4-yl)amino)thieno[2,3-b]pyridin-6(7H)-one (250 mg), TFA (4 mL), conc HCl (1 mL). $^1$H NMR (400 MHz, $CD_3OD$) δ 7.75 (d, J = 9.2 Hz, 1H), 7.44 (dd, J = 9.2, | |

-continued

| Example/IUPAC name | Structure | Yield; description; salt |
|---|---|---|
| 2.0 Hz, 1H), 7.35 (d, J = 2.0 Hz, 1H), 6.88 (s, 1H), 4.01-3.98 (m, 2H), 3.81-3.78 (m, 2H), 3.71-3.68 (m, 2H), 3.40-3.35 (m, 2H), 3.31-3.23 (m, 2H), 3.01 (s, 3H), 2.86-2.80 (m, 2H), 2.68 (s, 3H), 2.62-2.56 (m, 1H), 1.83-1.80 (m, 2H), 1.65-1.55 (m, 2H); MS ESI [M + H]$^+$ 479.1, calcd for [$C_{25}H_{30}N_6O_2S$ + H]$^+$ 479.2 | | |
| A21: 4-amino-5-(6-(4-methylpiperazin-1-yl)-1H-benzo[d]imidazol-2-yl)-3-(piperazin-1-yl)thieno[2,3-b]pyridin-6(7H)-one | 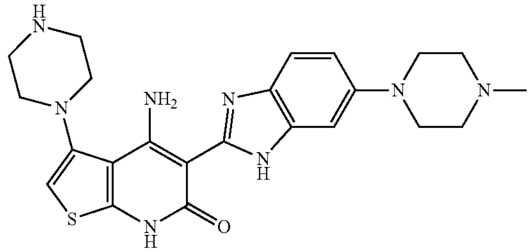 [SMILES: CN1CCN(c2ccc3nc(-c4c(N)c5c(N6CCNCC6)csc5[nH]c4=O)[nH]c3c2)CC1] | 74 mg (82%); tan solid; 2TFA |
| tert-Butyl 4-(4-amino-5-(6-(4-methylpiperazin-1-yl)-1H-benzo[d]imidazol-2-yl)-6-oxo-6,7-dihydro-thieno[2,3-b]pyridin-3-yl)piperazine-1-carboxylate (77.8 mg, 0.13 mmol) in DCM (20 mL) was treated with TFA (2 mL) at rt. The reaction was stirred 2.5 h before being concentrated under reduced pressure and purified by prep HPLC. $^1$H NMR (400 MHz, $CD_3OD$) δ 7.71 (d, J = 9.0 Hz, 1H), 7.40 (dd, J = 9.0, 2.3 Hz, 1H), 7.32 (d, J = 2.0 Hz, 1H), 6.40 (s, 1H), 4.02-3.85 (m, 2H), 3.74-3.61 (br m, 2H), 3.46-3.38 (m, 4H), 3.37-3.28 (m, 6H), 3.26-3.11 (m, 2H), 3.00 (s, 3H); MS ESI [M + H]$^+$ 465.4, calcd for [$C_{23}H_{28}N_8OS$ + H]$^+$ 465.2. | | |
| A22: 6-(6-(4-methylpiperazin-1-yl)-1H-benzo[d]imidazol-2-yl)-7-((pyridin-4-ylmethyl)amino)thieno[3,2-b]pyridin-5(4H)-one | 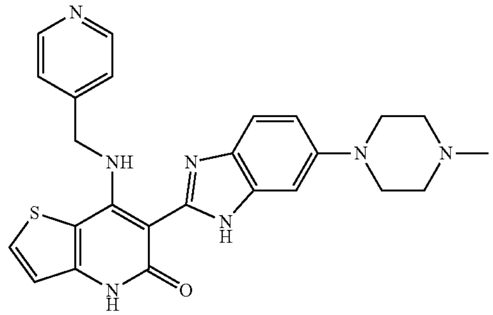 [SMILES: CN1CCN(c2ccc3nc(-c4c(NCc5ccncc5)c5sccc5[nH]c4=O)[nH]c3c2)CC1] | 16 mg (9%); yellow solid; TFA salt |
| Step 1: Reagents (general method C): a mixture of 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydro-thieno[3,2-b]pyridin-7-yl trifluoromethanesulfonate (crude, 0.3 mmol), pyridin-4-ylmethanamine (0.09 mL, 0.89 mmol). MS ESI [M + H]$^+$ 724.2, calcd for [$C_{34}H_{32}F_3N_7O_4S_2$ + H]$^+$ 724.2. Step 2: Reagents (general method D): 4-(4-methoxybenzyl)-6-(5 and/or 6-(4-methylpiperazin-1-yl)-1-((trifluoromethyl)sulfonyl)-1H-benzo[d]imidazol-2-yl)-7-((pyridin-4-ylmethyl)amino)thieno[3,2-b]pyridin-5(4H)-one, TFA (4 mL), conc. HCl (1 mL). $^1$H NMR (400 MHz, $CD_3OD$) δ 8.77 (d, J = 6.8 Hz, 2H), 8.05 (d, J = 6.8 Hz, 2H), 7.84 (d, J = 5.6 Hz, 1H), 7.58 (d, J = 8.8 Hz, 1H), 7.25 (d, J = 2.0 Hz, 1H), 7.14 (dd, J = 8.8, 2.0 Hz, 1H), 7.06 (d, J = 5.6 Hz, 1H), 5.41 (s, 2H), 3.91-3.78 (m, 2H), 3.75-3.59 (m, 2H), 3.41-3.33 (m, 2H), 3.21-3.05 (m, 2H), 3.00 (m, 3H). MS ESI [M + H]$^+$ 472.3, calcd for [$C_{25}H_{25}N_7OS$ + H]$^+$ 472.2. | | |

| Example/IUPAC name | Structure | Yield; description; salt |
|---|---|---|
| A23: 4-amino-3-(6-(4-methylpiperazin-1-yl)-1H-benzo[d]imidazol-2-yl)thieno[3,4-b]pyridin-2(1H)-one | 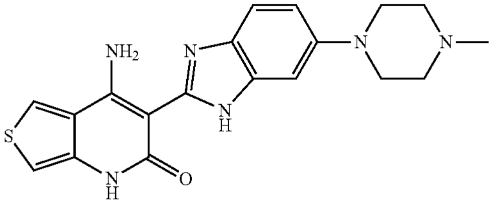 [SMILES: CN1CCN(c2ccc3nc(-c4c(N)c5cscc5[nH]c4=O)[nH]c3c2)CC1] | 43 mg (18%); Pale yellow solid 2HCl |
| Reagents (general method A1): ethyl 2-(6-(4-methylpiperazin-1-yl)-1H-benzo[d]imidazol-2-yl)acetate (160 mg, 0.52 mmol), 4-aminothiophene-3-carbonitrile (65 mg, 0.52 mmol), LDA (2.6 mL, 1 M in THF/hexane, 2.35 mmol), anh THF (6.0 mL) $^1$H NMR (400 MHz, $CD_3OD$) δ 8.39 (d, J = 3.2 Hz, 1H), 7.69 (d, J = 8.8 Hz, 1H), 7.39-7.37 (m, | | |

-continued

| Example/IUPAC name | Structure | Yield; description; salt |
|---|---|---|

1H), 7.30 (d, J = 2.0 Hz, 1H), 6.96 (d, J = 3.6 Hz, 1H), 3.97-3.94 (m, 2H), 3.71-3.67 (m, 2H), 3.39-3.35 (m, 2H), 3.24-3.18 (m, 2H), 3.01 (s, 3H); MS ESI [M + H]$^+$ 381.1, calcd for [$C_{19}H_{20}N_6OS$ + H]$^+$ 381.1

| Example/IUPAC name | Structure | Yield; description; salt |
|---|---|---|
| A24: 4-(cyclopentylamino)-3-(6-(4-methylpipepazin-1-yl)-1H-benzo[d]imidazol-2-yl)thieno[3,4-b]pyridin-2(1H)-one | 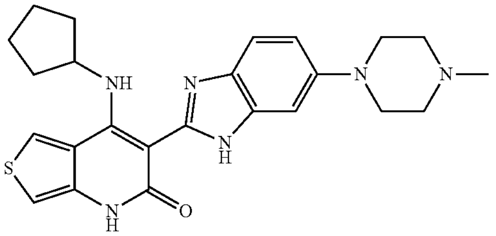 [SMILES: CN1CCN(c2ccc3nc(-c4c(NC5CCCC5)c5cscc5[nH]c4=O)[nH]c3c2)CC1] | 11 mg (5%); Yellow solid 2HCl |

Step-01: Reagents (general method C): 1-(4-methoxybenzyl)-3-(5 and/or 6-(4-methylpiperazin-1-yl)-1-((trifluoromethyl)sulfonyl)-1H-benzo[d]imidazol-2-yl)-2-oxo-1,2-dihydrothieno[3,4-b]pyridin-4-yl trifluoromethanesulfonate (223 mg, 0.29 mmol), cyclopentylamine (73 mL, 0.72 mmol), DCM (10 mL). MS ESI [M + H]$^+$ 701.2, calcd for [$C_{33}H_{35}F_3N_6O_4S_2$ + H]$^+$ 701.2

Step-02: Reagents (general method D): 4-(cyclopentylamino)-1-(4-methoxybenzyl)-3-(5 and/or 6-(4-methylpiperazin-1-yl)-1-((trifluoromethyl)sulfonyl)-1H-benzo[d]imidazol-2-yl)thieno[3,4-b]pyridin-2(1H)-one (180 mg, 0.25 mmol), TFA (7 mL), conc HCl (1 mL). $^1$H NMR (400 MHz, $CD_3OD$) δ 8.53 (d, J = 3.2 Hz, 1H), 7.71 (d, J = 9.2 Hz, 1H), 7.42 (dd, J = 9.2 Hz, 2.4 Hz, 1H), 7.32 (d, J = 2.0 Hz, 1H), 6.97 (d, J = 3.2 Hz, 1H), 3.99-3.96 (m, 2H), 3.70-3.67 (m, 2H), 3.39-3.35 (m, 2H), 3.28-3.22 (m, 2H), 3.01 (s, 3H), 1.71-1.69 (m, 6H), 1.38-1.37 (m, 2H), 1H merged with $H_2O$; MS ESI [M + H]$^+$ 449.2, calcd for [$C_{24}H_{28}N_6OS$ + H]$^+$ 449.2.

| Example/IUPAC name | Structure | Yield; description; salt |
|---|---|---|
| A25: 3-(6-(4-methylpiperazin-1-yl)-1H-benzo[d]imidazol-2-yl)-4-((tetrahydro-2H-pyran-4-yl)amino)thieno[3,4-b]pyridin-2(1H)-one | 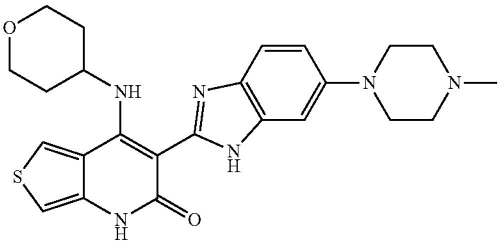 [SMILES: CN1CCN(c2ccc3nc(-c4c(NC5CCOCC5)c5cscc5[nH]c4=O)[nH]c3c2)CC1] | 12 mg (4%); Dark brown solid 2HCl |

Step-01: Reagents (general method C): 1-(4-methoxybenzyl)-3-(5 and/or 6-(4-methylpiperazin-1-yl)-1-((trifluoromethyl)sulfonyl)-1H-benzo[d]imidazol-2-yl)-2-oxo-1,2-dihydrothieno[3,4-b]pyridin-4-yl trifluoromethanesulfonate (380 mg, 0.49 mmol), tetrahydro-2H-pyran-4-amine (125 mg, 1.23 mmol), DCM (10 mL). MS ESI [M + H]$^+$ 717.2, calcd for [$C_{33}H_{35}F_3N_6O_5S_2$ + H]$^+$ 717.2

Step-02: Reagents (general method D): 1-(4-methoxybenzyl)-3-(5 and/or 6-(4-methylpiperazin-1-yl)-1-((trifluoromethyl)sulfonyl)-1H-benzo[d]imidazol-2-yl)-4-((tetrahydro-2H-pyran-4-yl)amino)thieno[3,4-b]pyridin-2(1H)-one (110 mg, 0.15 mmol), TFA (4 mL), conc HCl (0.5 mL). $^1$H NMR (400 MHz, $CD_3OD$) δ 8.50 (d, J = 3.2 Hz, 1H), 7.75 (d, J = 8.2 Hz, 1H), 7.45 (dd, J = 9.2 Hz, 2.4 Hz, 1H), 7.34 (d, J = 2.0 Hz, 1H), 6.98 (d, J = 3.2 Hz, 1H), 4.02-3.99 (m, 2H), 3.84-3.81 (m, 2 H), 3.71-3.68 (m, 2H), 3.50-3.37 (m, 2H), 3.27-3.21 (m, 2H), 3.02 (s, 3H), 2.80-2.77 (m, 2H), 2.75-2.64 (m, 1H), 1.80-1.66 (m, 4H); MS ESI [M + H]$^+$ 465.2, calcd for [$C_{24}H_{28}N_6O_2S$ + H]$^+$ 465.2

| Example/IUPAC name | Structure | Yield; description; salt |
|---|---|---|
| A26: 3-(6-(4-methylpiperazin-1-yl)-1H-benzo[d]imidazol-2-yl)-4-((2-morpholinoethyl)amino)thieno[3,4-b]pyridin-2(1H)-one | 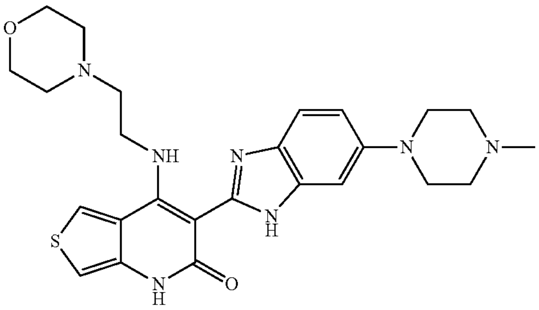 [SMILES: CN1CCN(c2ccc3nc(-c4c(NCCN5CCOCC5)c5cscc5[nH]c4=O)[nH]c3c2)CC1] | 38 mg (26%); Yellow solid Free base |

Step-01: Reagents (general method C): 1-(4-methoxybenzyl)-3-(5 and/or 6-(4-methylpiperazin-1-yl)-1-((trifluoromethyl)sulfonyl)-1H-benzo[d]imidazol-2-yl)-2-oxo-1,2-dihydrothieno[3,4-b]pyridin-4-yl trifluoromethanesulfonate (229 mg, 0.30 mmol), 2-morpholinoethanamine (97 mg, 0.75 mmol), DCM (6 mL). MS ESI [M + H]$^+$ 746.2, calcd for [$C_{34}H_{38}F_3N_7O_5S_2$ + H]$^+$ 746.2

Step-02: Reagents (general method D): 1-(4-methoxybenzyl)-3-(5 and/or 6-(4-

-continued

| Example/IUPAC name | Structure | Yield; description; salt |
|---|---|---|
| methylpiperazin-1-yl)-1-((trifluoromethyl)sulfonyl)-1H-benzo[d]imidazol-2-yl)-4-((2-morpholinoethyl)amino)thieno[3,4-b]pyridin-2(1H)-one (210 mg, 0.28 mmol), TFA (4 mL), conc HCl (0.5 mL). $^1$H NMR (Free base, 400 MHz, $CD_3OD$) δ 8.37 (d, J = 2.8 Hz, 1H), 7.42 (d, J = 8.8 Hz, 1H), 7.14 (s, 1H), 6.98 (d, J = 7.2 Hz, 1H), 6.87 (d, J = 3.2 Hz, 1H), 4.05 (t, J = 6.0 Hz, 2H), 3.75 (br.s, 4H), 3.21 (br.s, 4H), 2.85 (t, J = 6.0 Hz, 2H), 2.68-2.64 (m, 8 H), 2.38 (s, 3H); MS ESI $[M + H]^+$ 494.2, calcd for $[C_{25}H_{31}N_7O_2S + H]^+$ 494.2 | | |
| A27: 4-(cyclobutylamino)-3-(6-(4-methylpiperazin-1-yl)-1H-benzo[d]imidazol-2-yl)thieno[3,4-b]pyridin-2(1H)-one | 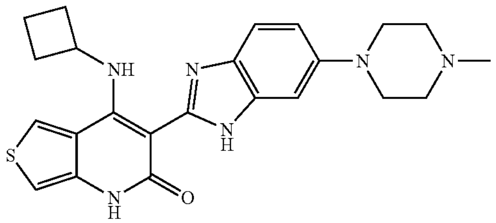 [SMILES: CN1CCN(c2ccc3nc(-c4c(NC5CCC5)c5cscc5[nH]c4=O)[nH]c3c2)CC1] | 30 mg (20%); Yellow solid 2HCl |
| Step-01: Reagents (General Method C): 1-(4-methoxybenzyl)-3-(5 and/or 6-(4-methylpipeazin-1-yl)-1-((trifluoromethyl)sulfonyl)-1H-benzo[d]imidazol-2-yl)-2-oxo-1,2-dihydrothieno[3,4-b]pyridin-4-yl trifluoromethanesulfonate (229 mg, 0.30 mmol), cyclobutylamine (53 mg, 0.75 mmol), DCM (6 mL) MS ESI $[M + H]^+$ 687.1, calcd for $[C_{32}H_{33}F_3N_6O_4S_2 + H]^+$ 687.2 Step-02: Reagents (general method D): 4-(cyclobutylamino)-1-(4-methoxybenzyl)-3-(5 and/or 6-(4-methylpiperazin-1-yl)-1-((trifluoromethyl)suflonyl)-1H-benzo[d]imidazol-2-yl)thieno[3,4-b]pyridin-2(1H)-one (210 mg, 0.28 mmol), TFA (4 mL), conc, HCl (0.5 mL). $^1$H NMR (400 MHz, $CD_3OD$) δ 8.51 (d, J = 3.6 Hz, 1H), 7.70 (d, J = 9.2 Hz, 1H), 7.41 (dd, J = 9.2 Hz, 2.0 Hz, 1H), 7.31 (d, J = 2.0 Hz, 1H), 6.96 (d, J = 3.2 Hz, 1H), 3.99-3.96 (m, 2H), 3.71-3.68 (m, 2H), 3.63-3.59 (m, 1H), 3.39-3.35 (m, 2H), 3.28-3.22 (m, 2H), 3.01 (s, 3H), 2.23-2.21 (m, 2H), 2.06-2.00 (m, 2H), 1.74-1.66 (m, 1H), 1.49-1.38 (m, 1H); MS ESI $[M + H]^+$ 435.2, calcd for $[C_{23}H_{26}N_6OS + H]^+$ 435.1 | | |
| A28: 3-(6-(4-methylpiperazin-1-yl)-1H-benzo[d]imidazol-2-yl)-4-((pyridin-2-ylmethyl)amino)thieno[3,4-b]pyridin-2(1H)-one | 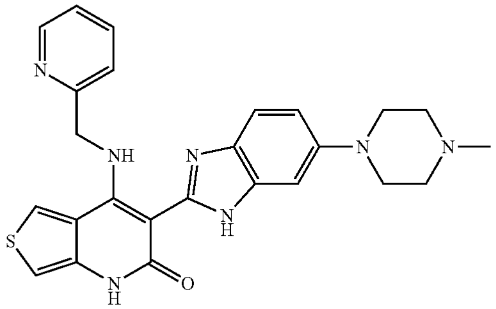 [SMILES: CN1CCN(c2ccc3nc(-c4c(NCc5ccccn5)c5cscc5[nH]c4=O)[nH]c3c2)CC1] | 15 mg (13%); Pale yellow solid 2HCl |
| Step-01: Reagents (general method C): 1-(4-methoxybenzyl)-3-(5 and/or 6-(4-methylpiperazin-1-yl)-1-((trifluoromethyl)sulfonyl)-1H-benzo[d]imidazol-2-yl)-2-oxo-1,2-dihydrothieno[3,4-b]pyridin-4-yl trifluoromethanesulfonate (168 mg, 0.22 mmol), 2-Picolylamine (60 mg, 0.55 mmol), DCM (4 mL) MS ESI $[M + H]^+$ 724.1, calcd for $[C_{34}H_{32}F_3N_7O_4S_2 + H]^+$ 724.2 Step-02: Reagents (general method D): 1-(4-methoxybenzyl)-3-(5 and/or 6-(4-methylpiperazin-1-yl)-1-((trifluoromethyl)sulfonyl)-1H-benzo[d]imidazol-2-yl)-4-((pyridin-2-ylmethyl)amino)thieno[3,4-b]pyridin-2(1H)-one (65 mg, 0.09 mmol), TFA (3 mL), conc HCl (0.5 mL). $^1$H NMR (400 MHz, $CD_3OD$) δ 8.62 (d, J = 5.6 Hz, 1H), 8.49-8.43 (m, 2H), 7.97-7.93 (m, 1H), 7.85 (d, J = 8.0 Hz, 1H), 7.62 (d, J = 9.2 Hz, 1H), 7.40 (dd, J = 9.2 Hz, 2.4 Hz, 1H), 7.23 (d, J = 2.0 Hz, 1H), 7.04 (d, J = 3.2 Hz, 1H), 4.84 (s, 2H), 4.00-3.96 (m, 2H), 3.70-3.67 (m, 2H), 3.40-3.37 (m, 2H), 3.28-3.22 (m, 2H), 3.02 (s, 3H); MS ESI $[M + H]^+$ 472.2, calcd for $[C_{25}H_{25}N_7OS + H]^+$ 472.2 | | |

| Example/IUPAC name | Structure | Yield; description; salt |
|---|---|---|
| A29: 7-hydroxy-6-(6-(4-methylpiperazin-1-yl)-1H-benzo[d]imidazol-2-yl)thieno[3,2-b]pyridin-5(4H)-one | 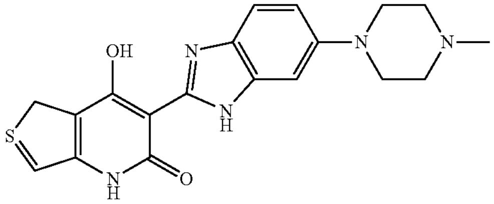 | 6.6 mg (10%); Pale yellow solid; TFA |

Step 1: Reagents (general method A1): 1-(4-methoxybenzyl)-1H-thieno[3,2-d][1,3]oxazine-2,4-dione (0.75 g, 2.6 mmol), ethyl 2-(6-(4-methylpiperazin-1-yl)-1H-benzo[d]imidazol-2-yl)acetate (0.79 g, 2.6 mmol), KHMDS (13 mL, 13 mmol), THF (30 mL). $^1$H NMR (400 MHz, $CDCl_3$) δ 13.64 (br. s, 1H), 12.64 (br.s., 1H), 7.52 (br. s., 1H), 7.40-7.29 (m, 1H), 7.21 (d, J = 7.5 Hz, 2H), 7.04-6.88 (m, 3H), 6.84 (d, J = 8.0 Hz, 2H), 5.35 (br. s., 2H), 3.76 (s, 3H), 3.20 (br.s., 4H), 2.62 (br. s., 4H), 2.39 (br.s., 3 H); MS ESI [M + H]$^+$ 502.4, calcd for [$C_{27}H_{27}N_5O_3S$ + H]$^+$ 502.18.

Step 2: Reagents (general method D): 7-hydroxy-4-(4-methoxybenzyl)-9-(6-(4-methylpiperazin-1-yl)-1H-benzo[d]imidazol-2-yl)thieno[3,2-b]pyridin-5(4H)-one (0.090 g, 0.18 mmol), TFA (7 mL), and conc. HCl (1 mL). $^1$H NMR (400 MHz, DMSO-$d_6$) δ 13.52-13.14 (m, 2 H), 11.25 (s, 1H), 9.79 (br. s, 1H), 7.81 (d, J = 5.3 Hz, 1H), 7.64 (d, J = 8.8 Hz, 1H), 7.37 (d, J = 2.3 Hz, 1H), 7.10 (dd, J = 9.0, 2.5 Hz, 1H), 6.92 (d, J = 5.0 Hz, 1H), 3.85-3.66 (m, 2H), 3.64-3.46 (m, 2H), 3.29-3.13 (m, 2H), 3.09-2.92 (m, 2H), 2.87 (s, 3H); MS ESI [M + H]$^+$ 382.3, calcd for [$C_{19}H_{19}N_5O_2S$ + H]$^+$ 382.45.

| Example/IUPAC name | Structure | Yield; description; salt |
|---|---|---|
| A30: 7-amino-6-(6-(4-methylpiperazin-1-yl)-1H-benzo[d]imidazol-2-yl)thieno[3,2-b]pyridin-5(4H)-one | 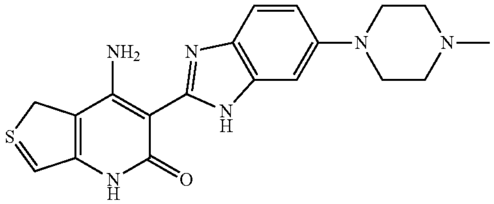 | 1.5 g (79%) yellow solid free base |

A solution of 3-aminothiophene-2-carbonitrile (951 mg, 7.67 mmol) and ethyl 2-(6-(4-mehtylpiperazin-1-yl)-1H-benzo[d]imidazol-2-yl)acetate (2.316 g, 7.67 mmol) in anhydrous THF (55 mL) was heated up to 40° C. in oil bath and LiHMDS (30.7 mL, 1.0 M in THF, 30.7 mmol) was added dropwise over 30 minutes. The resulting reaction mixture was stirred at 40° C. for 2 h then cooled down to rt and quenched with satd aq $NH_4Cl$ in ice bath. The aqueous layer was extracted with EtOAc. The combined organic layers were dried over $Na_2SO_4$ and concentrated under reduced pressure. The residue was triturated with DCM and filtered. The filter cake was triturated again with MeOH then filtered to give the title compound as a bright yellow solid (1.495 g, 79%). $^1$H NMR (400 MHz, DMSO-$d_6$) δ 12.34 (s, 1H), 11.81 (s, 1H), 10.73-10.47 (m, 1H), 7.96-7.91 (m, 1H), 7.90-7.78 (m, 1H), 7.52-7.43 (m, 1H), 7.09-7.25 (m, 1H), 7.00 (d, J = 5.3 Hz, 1H), 6.93-6.86 (m, 1H), 3.18-3.14 (m, 4H), 2.65-2.54 (m, 4H), 2.30 (s, 3H); MS ESI [M + H]$^+$ 381.5, calcd for [$C_{19}H_{20}N_6OS$ + H]$^+$ 381.1.

| Example/IUPAC name | Structure | Yield; description; salt |
|---|---|---|
| A31: 7-amino-6-(6-morpholino-1H-benzo[d]imidazol-2-yl)thieno[3,2-b]pyridin-5(4H)-one | 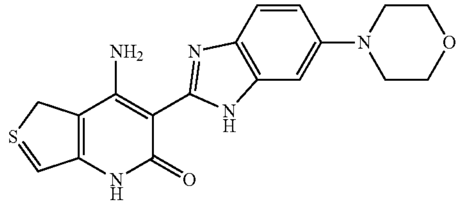 | 16 mg (13%); white solid; HCl |

LiHMDS (1.0 M in THF, 1.7 mL, 1.7 mmol) was added dropwise over 10 min to a stirred solution of 3-aminothiophene-2-carbonitrile (0.425 g, 0.34 mmol), ethyl 2-(6-morpholin-1H-benzo[d]imidazol-2-yl)acetate (0.103 g, 0.36 mmol) in anh THF (10 mL) at rt under Ar. The reaction was heated at 40° C. for 1 h and directly purified by flash chromatography (MeOH in $CH_2Cl_2$ 0-10%) followed by prep HPLC. The material was further recrystallized form EtOAc/hexanes and triturated with MeOH. The resulting grey solid (25 mg) was suspended in MeOH and treated with HCl (1.0 M in $Et_2O$, 0.14 mL) at rt. The reaction was concentrated under reduced pressure Free base: $^1$H NMR (400 MHz, DMF-$d_7$) δ 11.94 (s, 1H), 8.18 (m, 1H), 7.78 (d, J = 8.3 Hz, 1H), 7.52 (s, 1H), 7.35 (d, J = 5.2 Hz, 1H), 7.25 (d, J = 7.8 Hz, 1H), 4.06-4.00 (m, 4H), 3.40 (br s, 4H). *three exchangeable protons are likely obscured by a peak due to $H_2O$ and DMF-$d_7$; MS ESI [M + H]$^+$ 368.2, calcd for [$C_{18}H_{17}N_5O_2S$ + H]$^+$ 368.1.

-continued

| Example/IUPAC name | Structure | Yield; description; salt |
|---|---|---|
| A32: 7-amino-2-methyl-6-(6-(4-methylpiperazin-1-yl)-1H-benzo[d]imidazol-2-yl)thieno[3,2-b]pyridin-5(4H)-one | 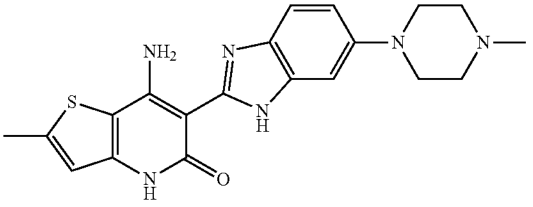 | 124 mg (44%); brown solid; TFA |

Reagents (general method A1): 3-amino-5-methylthiophene-2-carbonitrile (0.080 g, 0.58 mmol), ethyl 2-(6-(4-methylpiperazin-1-yl)-1H-benzo[d]imidazol-2-yl)acetate (0.18 g, 0.58 mmol), LDA (2.6 mL, 2.6 mmol), THF (5 mL). $^1$H NMR (400 MHz, DMSO-$d_6$) δ 11.75 br. s., 1H), 9.84 (br. s., 1H), 7.53 (br.s., 1H), 7.24 (br.s., 1H), 6.98 ( br.s., 1H), 6.77 (br. s., 1H), 3.82-3.39 (m, 7H), 3.22 (br. s., 2H), 3.08-2.76 (m, 5H), 2.56 (br.s., 3H); MS ESI [M + H]$^+$ 395.3, calcd for [$C_{20}H_{22}N_6OS$ + H]$^+$ 395.5.

| | | |
|---|---|---|
| A33: 7-amino-6-(6-(3r,5s)-rel-3,4,5-trimethylpiperazin-1-yl)-1H-benzo[d]imidazol-2-yl)thieno[3,2-b]pyridin-5(4H)-one | 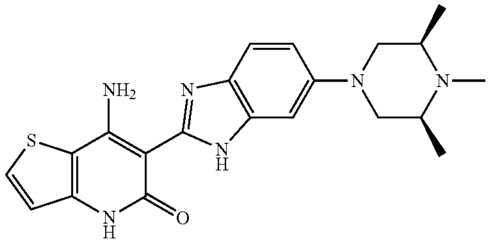 [SMILES: C[C@@H]1CN(c2ccc3nc(-c4c(N)c5sccc5[nH]c4=O)[nH]c3c2)C[C@H](C)N1C] | 43 mg (18%); yellow solid; 2HCl |

Reagents (general method A1): ethyl 2-(6-((3r,5s)-retl-3,4,5-trimethylpiperazin-1-yl)-1H-benzo[d]imidazol-2-yl)acetate (165 mg, 0.5 mmol), 3-aminothiophene-2-carbonitrile (124 mg, 1 mmol), LDA (1.0 M in THF/hex, 2.5 mL, 2.5 mmol), THF (8 mL). $^1$H NMR (400 MHz, $CD_3OD$) δ 7.99 (d, J = 1.6 Hz, 1H), 7.68 (d, J = 9.2 Hz, 1H), 7.38 (dd, J = 9.0, 2.2 Hz, 1H), 7.31 (d, J = 2.0 Hz, 1H), 7.11 (d, J = 5.6 Hz, 1H), 4.03-3.95 (m, 2H), 3.65-3.55 (m, 2H), 3.10-3.04 (m, 2H), 3.03 (s, 3H), 1.56 (d, J = 6.4 Hz, 6H); MS ESI [M + H]$^+$ 409.3, calcd for [$C_{21}H_{24}N_6OS$ + H]$^+$ 409.17.

| | | |
|---|---|---|
| A34: 7-(cyclopentylamino)-6-(6-(4-methylpiperazin-1-yl)-1H-benzo[d]imidazol-2-yl)thieno[3,2-b]pyridin-5(4H)-one | 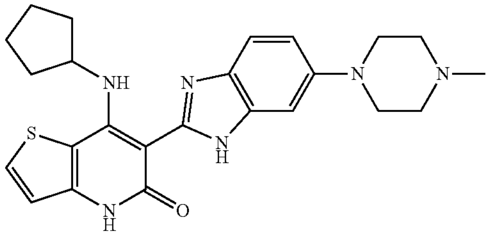 [SMILES: CN1CCN(c2ccc3nc(-c4c(NC5CCCC5)c5sccc5[nH]c4=O)[nH]c3c2)CC1] | 77 mg (26%); brown solid; TFA |

Step 1: Reagents (general method C); a mixture of 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydro-thieno[3,2-b]pyridin-7-yl trifluoromethanesulfonate (0.41 g, 0.54 mmol), cyclopentylamine (0.13 mL, 1.3 mmol), MeCN (10 mL). MS ESI [M + H]$^+$ 701.3, calcd for [$C_{33}H_{35}F_3N_6O_4S_2$ + H]$^+$ 701.2.

Step 2: Reagents (general method D): a mixture of 7-(cyclopentylamino)-4-(4-methoxybenzyl)-6-(5 and/or 6-(4-methylpiperazin-1-yl)-1-((trifluoromethyl)sulfonyl)-1H-benzo[d]imidazol-2-yl)thieno[3,2-b]pyridin-5(4H)-one (0.38 g, 0.54 mmol), TFA (7 mL), and conc. HCl (1 mL). $^1$H NMR (400 MHz, DMSO-$d_6$) δ 12.99 (br.s, 1H), 12.11 (br.s, 1H), 11.87 (s, 1H), 9.65 (br. s, 1H), 8.04 (d, J = 5.5 Hz, 1H), 7.61-7.40 (m, 1H), 7.32-7.13 (m, 1H), 7.04 (d, J = 5.5 Hz, 1H), 6.93 (dd, J = 8.5, 2.5 Hz, 1H), 4.72-4.60 (m, 1H), 3.80-3.69 (m, 2H), 3.59-3.52 (m, 2H), 3.29-3.15 (m, 2H), 3.02-2.90 (m, 2H), 2.88 (d, J = 3.5 Hz, 3H), 2.21-2.06 (m, 2H), 1.93-1.67 (m, 6H); MS ESI [M + H]$^+$ 449.3, calcd for [$C_{24}H_{28}N_6OS$ + H]$^+$ 449.2.

-continued

| Example/IUPAC name | Structure | Yield; description; salt |
|---|---|---|
| A35: 6-(6-(4-methylpiperazin-1-yl)-1H-benzo[d]imidazol-2-yl)-7-((tetrahydro-2H-pyran-4-yl)amino)thieno[3,2-b]pyridin-5(4H)-one | 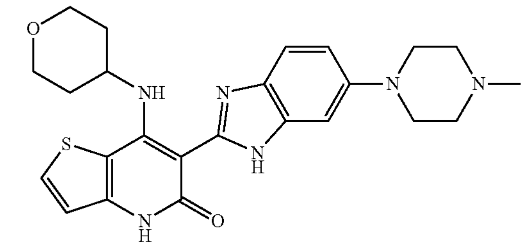 [SMILES: CN1CCN(c2ccc3nc(-c4c(NC5CCOCC5)c5sccc5[nH]c4=O)[nH]c3c2)CC1] | 69 mg (52%); yellow solid; TFA |

Step 1: Reagents (general method C): a mixture of 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydro-thieno[3,2-b]pyridin-7-yl trifluoromethansulfonate (0.18 g, 0.23 mmol), tetrahydro-2H-pyran-4-amine (0.058 mL, 0.58 mmol), MeCN (5 mL). MS ESI $[M + H]^+$ 717.3, calcd for $[C_{33}H_{35}F_3N_6O_5S_2 + H]^+$ 717.2.

Step 2: Reagents (general method D): a mixture of 4-(4-methoxybenzyl)-6-(5 and/or 6-(4-methylpiperazin-1-yl)-1-((trifluoromethyl)sulfonyl)-1H-benzo[d]imidazol-2-yl)-7-((tetrahydro-2H-pyran-4-yl)amino)thieno[3,2-b]pyridin-5(4H)-one (0.17 g, 0.23 mmol), TFA (7 mL), and conc. HCl (1 mL). $^1$H NMR (400 MHz, DMSO-$d_6$) δ 13.02 (br.s, 1H), 12.18 (br. s, 1H), 11.92 (s, 1H), 9.63 (br.s, 1H), 8.04 (d, J = 5.5 Hz, 1H), 7.54 (d, J = 8.0 Hz, 1H), 7.30-7.14 (m, 1 H), 7.04 (d, J = 5.5 Hz, 1H), 6.96 (dd, J = 8.3, 2.3 Hz, 1H), 4.49-4.34 (m, 1H), 4.02-3.93 (m, 2H), 3.81-3.74 (m, 2H), 3.57 (d, J = 9.0 Hz, 4H), 3.31-3.15 (m, 2H), 3.02-2.91 (m, 2H), 2.88 (d, J = 3.8 Hz, 3H), 2.13 (d, J = 3.3 Hz, 2H), 1.81-1.64 (m, 2H); MS ESI $[M + H]^+$ 465.3, calcd for $[C_{24}H_{28}N_6O_2S + H]^+$ 465.2.

| Example/IUPAC name | Structure | Yield; description; salt |
|---|---|---|
| A36: 7-(((1R*,3S*)-3-hydroxycyclopentyl)amino)-6-(6-(4-methylpiperazin-1-yl)-1H-benzo[d]imidazol-2-yl)thieno[3,2-b]pyridin-5(4H)-one | 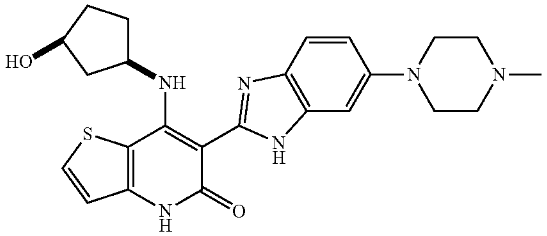 | 33 mg (28%); yellow solid; TFA |

Step 1: Reagents (general method C): a mixture of 4-(4-methoxybenzyl)-6-(5 and/or 6-(4-methyl-piperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (0.15 g, 0.20 mmol), (1S*,3R*)-3-aminocyclopentanol (0.070 g, 0.50 mmol), DCM (10 mL). MS ESI $[M + H]^+$ 717.3, calcd for $[C_{33}H_{35}F_3N_6O_5S_2 + H]^+$ 717.2

Step 2: Reagents (general method D): a mixture of 7-(((1R*,3S*)-3-hydroxycyclopentyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno[3,2-b]pyridin-5(4H)-one (0.14 g, 0.20 mmol), TFA (7 mL), and conc. HCl (1 mL). $^1$H NMR (400 MHz, $CD_3OD$) δ 8.04 (d, J = 5.5 Hz, 1H), 7.61 (d, J = 9.0 Hz, 1H), 7.29-7.20 (m, 2H), 7.11 (d, J = 5.5 Hz, 1H), 4.82-4.73 (m, 1H), 4.57-4.47 (m, 1H), 3.96-3.79 (m, 2H), 3.74-3.58 (m, 2H), 3.42-3.33 (m, 2H), 3.22-3.08 (m, 2H), 3.01 (s, 3H), 2.33-2.19 (m, 2H), 2.16-2.02 (m, 3H), 2.02-1.88 (m, 1H); MS ESI $[M + H]^+$ 465.2, calcd for $[C_{24}H_{28}N_6O_2S + H]^+$ 465.2.

| Example/IUPAC name | Structure | Yield; description; salt |
|---|---|---|
| A37: 7-(((1r,4r)-4-hydroxycyclohexyl)amino)-6-(6-(4-methylpiperazin-1-yl)-1H-benzo[d]imidazol-2-yl)thieno[3,2-b]pyridin-5(4H)-one | 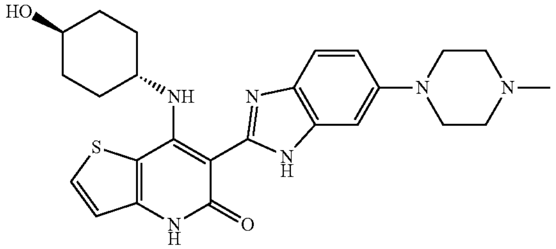 [SMILES: CN1CCN(c2ccc3nc(-c4c(N[C@H]5CC[C@H](O)CC5)c5sccc5[nH]c4=O)[nH]c3c2)CC1] | 10 mg (9%), yellow solid; free base |

Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.24 mmol), trans-4-aminocyclohexanol (0.11 g, 0.96 mmol), MeCN (10 mL). MS ESI $[M + H]^+$ 731.2 calcd for $[C_{34}H_{37}F_3N_6O_5S_2 + H]^+$ 731.2.

-continued

| Example/IUPAC name | Structure | Yield; description; salt |
|---|---|---|
| Step 2: (general method D): 7-(((1r,4r)-4-hydroxycyclohexyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno[3,2-b]py-ridin-5(4H)-one (crude, 0.24 mmol), TFA (7 mL), HCl (1 mL); $^1$H NMR (400 MHz, $CD_3OD$) δ 7.88 (d, J = 5.5 Hz, 1H), 7.51-7.41 (m, 1H), 7.24-7.14 (m, 1H), 7.08 (d, J = 5.5 Hz, 1H), 7.03-6.95 (m, 1H), 4.32-4.21 (m, 1H), 3.82-3.71 (m, 1H), 3.28-3.20 (m, 4H), 2.86-2.74 (m, 4H), 2.47 (s, 3H), 2.24-2.36 (m, 2H), 2.17-2.06 (m, 2H), 1.78-1.63 (m, 2H), 1.62-1.49 (m, 2H); MS ESI [M + H]$^+$ 479.2, calcd for [$C_{25}H_{30}N_6O_2$ S + H]$^+$ 479.3. | | |
| A38: 6-(6-(4-methylpiperazin-1-yl)-1H-benzo[d]imidazol-2-yl)-7-(((tetrahydro-2H-pyran-4-yl)methyl)amino)thieno[3,2-b]pyridin-5(4H)-one | 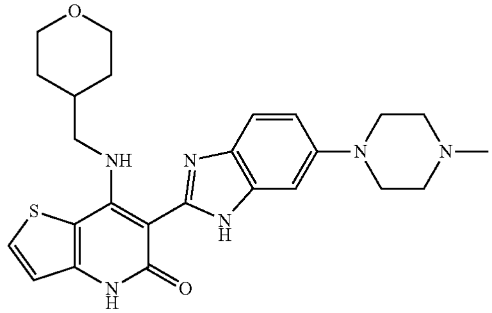 [SMILES: CN1CCN(c2ccc3nc(-c4c(NCC5CCOCC5)c5sccc5[nH]c4=O)[nH]c3c2)CC1] | 24 mg (32%) yellow solid Free base |
| Step 1: Reagents (general method C): 4-(4-methoxybenzyl)-6-(5-and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.16 mmol), 4-aminomethyltetrahydropyran (0.074 g, 0.64 mmol), MeCN (10 mL). MS ESI [M + H]$^+$ 731.3, calcd for [$C_{34}H_{37}F_3N_6O_5S_2$ + H]$^+$ 731.2. Step 2: Reagents (general method D): 4-(4-methoxybenzyl)-6-(5 and/or 6-(4-methylpiperazin-1-yl)-1-((trifluoromethyl)sulfonyl)-1H-benzo[d]imidazol-2-yl)-7-(((tetrahydro-2H-pyran-4-yl)methyl)amino)-thieno[3,2-b]pyridin-5(4H)-one (crude, 0.16 mmol), TFA (7 mL), HCl (1 mL). $^1$H NMR (400 MHz, $CD_3OD$) δ 7.93-7.83 (m, 1H), 7.49-7.40 (m, 1H), 7.21-7.13 (m, 1H), 7.12-7.06 (m, 1H), 7.05-6.96 (m, 1H), 4.10-3.97 (m, 2H), 3.89-3.79 (m, 2H), 3.56-3.44 (m, 2H), 3.26-3.16 (m, 4H), 2.77-2.65 (m, 4H), 2.40 (s, 3H), 2.19-2.07 (m, 1H), 1.99-1.88 (m, 2H), 1.65-1.50 (m, 2H); MS ESI [M + H]$^+$ 479.3, calcd for [$C_{25}H_{30}N_6O_2S$ + H]$^+$ 479.2. | | |
| A39: 6-(6-(4-methylpiperazin-1-yl)-1H-benzo[d]imidazol-2-yl)-7-(piperidin-4-ylamino)thieno[3,2-b]pyridin-5(4H)-one | 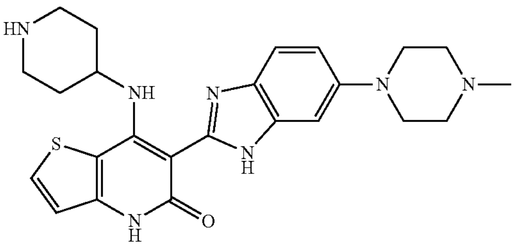 [SMILES: CN1CCN(c2ccc3nc(-c4c(NC5CCNCC5)c5sccc5[nH]c4=O)[nH]c3c2)CC1] | 17 mg (19%) Brown solid Free base |
| Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.20 mmol), tert-butyl 4-aminopiperidine-1-carboxylate (0.16 g, 0.80 mmol), MeCN (10 mL). MS ESI [M + H]$^+$ 816.2, calcd for [$C_{38}H_{44}F_3N_7O_6S_2$ + H]$^+$ 816.2 Step 2: Reagents (general method D): tert-butyl 4-((4-(4-methoxybenzyl)-6-(5 and/or 6-(4-methyl-piperazin-1-yl)-1-((trifluoromethyl)sulfonyl)-1H-benzo[d]imidazol-2-yl)-5-oxo-4,5-dihydrothieno[3,2-b]pyridin-7-yl)amino)piperidine-1-carboxylate (crude, 0.20 mmol), TFA (6 mL), HCl (1 mL). $^1$H NMR (400 MHz, $CD_3OD$) δ 7.90-7.83 (m, 1H), 7.52-7.42 (m, 1H), 7.25-7.11 (m, 1H), 7.10-7.05 (m, 1H), 7.04-6.96 (m, 1H), 4.50-4.42 (m, 1 H), 3.27-3.16 (m, 6H), 2.91-2.79 (m, 2H), 2.73-2.61 (m, 4H), 2.37 (s, 3H), 2.26-2.17 (m, 2H), 1.89-1.73 (m, 2H); MS ESI [M + H]$^+$ 464.2, calcd for [$C_{24}H_{29}N_7OS$ + H]$^+$ 464.2. | | |
| A40: 7-(((1S,4S)-4-hydroxycyclohexyl)amino)-6-(6-(4-methylpiperazin-1-yl)-1H-benzo[d]imidazol-2-yl)thieno-[3,2-b]pyridin-5(4H)-one | 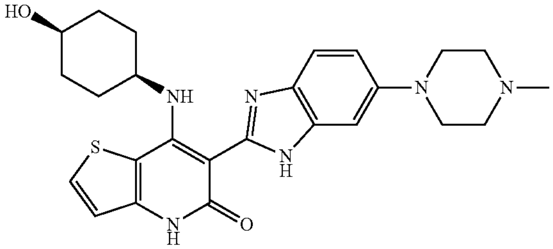 [SMILES: CN1CCN(c2ccc3nc(-c4c(N[C@H]5CC[C@@H](O)CC5)c5sccc5[nH]c4=O)[nH]c3c2)CC1] | 35 mg (30%), yellow solid; free base |
| Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2- | | |

-continued

| Example/IUPAC name | Structure | Yield; description; salt |
|---|---|---|
| b]pyridin-7-yl trifluoromethanesulfonate (crude, 0.24 mmol), cis-4-aminocyclohexanol (0.11 g, 0.96 mmol), MeCN (10 mL). MS ESI [M + H]$^+$ 731.2, calcd for [$C_{34}H_{37}F_3N_6O_5S_2$ + H]$^+$ 731.2<br>Step 2: (general method D): 7-(((1S,4S)-4-hydroxycyclohexyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno[3,2-b]pyridin-5(4H)-one (crude, 0.24 mmol), TFA (5 mL), HCl (1 mL). $^1$H NMR (400 MHz, $CD_3OD$) δ 7.88-7.82 (m, 1H), 7.56-7.41 (m, 1H), 7.29-7.14 (m, 1H), 7.08 (d, J = 5.2 Hz, 1H), 7.04-6.96 (m, 1H), 4.50-4.40 (m, 1H), 3.90-3.80 (m, 1H), 3.26-3.17 (m, 4H), 2.73-2.63 (m, 4H), 2.38 (s, 3H), 2.13-1.81 (m, 8H); MS ESI [M + H]$^+$ 479.2, calcd for [$C_{25}H_{30}N_6O_2S$ + H]$^+$ 479.2 | | |
| A41: 7-(((1S,2S)-2-hydroxycyclohexyl)amino)-6-(6-(4-methylpiperazin-1-yl)-1H-benzo[d]imidazol-2-yl)thieno[3,2-b]pyridin-5(4H)-one | 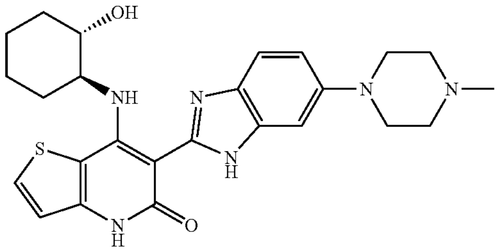 [SMILES: CN1CCN(c2ccc3nc(-c4c(N[C@H]5CCCC[C@@H]5O)c5sccc5[nH]c4=O)[nH]c3c2)CC1] | 16 mg (23%), yellow solid; free base |
| Step 1: (general method C): 4-(4-methoxybenzyl)-6-(5 and/or 6-(4-methylpiperazin-1-yl)-1-((trifluoro-methyl)sulfonyl)-1H-benzo[d]imidazol-2-yl)-5-oxo-4,5-dihydrothieno[3,2-b]pyridin-7-yl trifluoro-methanesulfonate (crude, 0.20 mmol), (1S,2S)-2-aminocyclohexanol (0.091 g, 0.80 mmol), DMF (7 mL). MS ESI [M + H]$^+$ 731.2, calcd for [$C_{34}H_{37}F_3N_6O_5S_2$ + H] 731.2<br>Step 2: Reagents (general method D): 7-(((1S,2S)-2-hydroxycyclohexyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno-[3,2-b]pyridin-5(4H)-one (crude, 0.14 mmol), TFA (5 mL), HCl (1 mL). $^1$H NMR (400 MHz, $CD_3OD$) δ 7.84 (d, J = 5.5 Hz, 1H), 7.55-7.40 (m, 1H), 7.18-7.12 (m, 1H), 7.06 (d, J = 5.5 Hz, 1H), 7.03-6.94 (m, 1H), 4.24-4.14 (m, 1H), 3.88-3.77 (m, 1H), 3.27-3.18 (m, 4H), 2.81-2.70 (m, 4H), 2.44 (s, 3H), 2.33-2.23 (m, 1H), 2.20-2.10 (m, 1H), 1.91-1.78 (m, 2H), 1.65-1.42 (m, 4H); MS ESI [M + H]$^+$ 479.3, calcd for [$C_{25}H_{30}N_6O_2S$ + H]$^+$ 479.3 | | |
| A42: 7-(((1S,2S)-2-hydroxycyclopentyl)amino)-6-(6-(4-methylpiperazin-1-yl)-1H-benzo[d]imidazol-2-yl)thieno[3,2-b]pyridin-5(4H)-one | 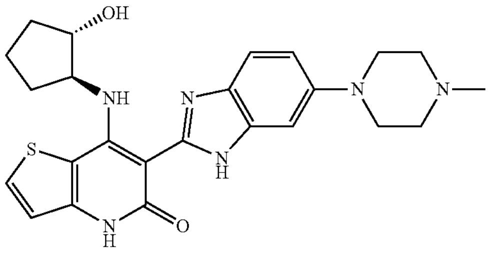 [SMILES: CN1CCN(c2ccc3nc(-c4c(N[C@H]5CCC[C@@H]5O)c5sccc5[nH]c4=O)[nH]c3c2)CC1] | 20 mg (13%), yellow solid; free base |
| Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.32 mmol), (1S,2S)-2-aminocyclopentanol (0.13 g, 1.3 mmol), DMF (7 mL). MS ESI [M + H]$^+$ 717.2 calcd for [$C_{33}H_{35}F_3N_6O_5S_2$ + H]$^+$ 717.2<br>Step 2: Reagents (general method D): 7-(((1S,2S)-2-hydroxycyclopentyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno-[3,2-b]pyridin-5(4H)-one (crude, 0.32 mmol), TFA (5 mL), HCl (5 mL). $^1$H NMR (400 MHz, $CD_3OD$) δ 7.90-7.84 (m, 1H), 7.48-7.40 (m, 1H), 7.20-7.11 (m, 1H), 7.07 (d, J = 5.2 Hz, 1H), 7.03-6.93 (m, 1H), 4.61-4.53 (m, 1H), 4.42-4.34 (m, 1H), 3.27-3.15 (m, 4H), 2.76-2.64 (m, 4H), 2.45-2.32 (m, 4H), 2.30-2.17 (m, 1H), 2.06-1.94 (m, 2H), 1.93-1.82 (m, 1H), 1.82-1.70 (m, 1H); MS ESI [M + H]$^+$ 465.2 calcd for [$C_{24}H_{28}N_6O_2S$ + H]$^+$ 465.2 | | |

-continued

| Example/IUPAC name | Structure | Yield; description; salt |
|---|---|---|
| A43: 6-(6-morpholino-1H-benzo[d]imidazol-2-yl)-7-(piperidin-4-ylamino)thieno[3,2-b]pyridin-5(4H)-one | 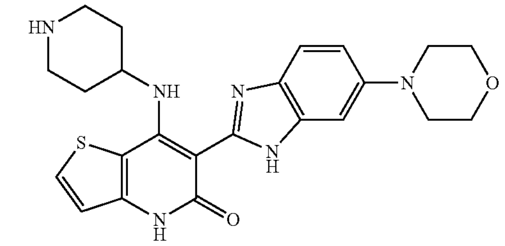 [SMILES: O=c1[nH]c2ccsc2c(NC2CCNCC2)c1-c1nc2ccc(N3CCOCC3)cc2[nH]1] | 11 mg (12%), brown solid; free base |

Step 1: Reagents (general method C): 4-(4-methoxybenzyl)-6-(5 and/or 6-morpholino-1-((trifluoro-methyl)sulfonyl)-1H-benzo[d]imidazol-2-yl)-5-oxo-4,5-dihydrothieno[3,2-b]pyridin-7-yl trifluoro-methanesulfonate (crude, 0.20 mmol), tert-butyl 4-aminopiperidine-1-carboxylate (0.16 g, 0.8 mmol), DMF (7 mL). MS ESI $[M + H]^+$ 803.2, calcd for $[C_{37}H_{41}F_3N_6O_7S_2 + H]^+$ 803.2.

Step 2: Reagents (general method D): tert-butyl 4-((4-(4-methoxybenzyl)-6-(5 and/or 6-morpholino-1-((trifluoromethyl)sulfonyl)-1H-benzo[d]imidazol-2-yl)-5-oxo-4,5-dihydrothieno[3,2-b]pyridin-7-yl)-amino)piperidine-1-carboxylate (crude, 0.20 mmol), TFA (5 mL), HCl (1 mL). $^1$H NMR (400 MHz, $CD_3OD$) δ 7.90-7.84 (m, 1H), 7.52-7.42 (m, 1H), 7.23-7.13 (m, 1H), 7.08 (d, J = 5.2 Hz, 1H), 7.04-6.95 (m, 1H), 4.54-4.43 (m, 1H), 3.93-3.83 (m, 4H), 3.29-3.24 (m, 2H), 3.20-3.10 (m, 4H), 2.98-2.86 (m, 2H), 2.29-2.18 (m, 2H), 1.90-1.78 (m, 2H); MS ESI $[M + H]^+$ 451.3, calcd for $[C_{23}H_{26}N_6O_2S + H]^+$ 451.2.

| Example/IUPAC name | Structure | Yield; description; salt |
|---|---|---|
| A44: 7-(((1S,2R)-2-hydroxycyclohexyl)amino)-6-(6-(4-methylpiperazin-1-yl)-1H-benzo[d]imidazol-2-yl)thieno[3,2-b]pyridin-5(4H)-one | 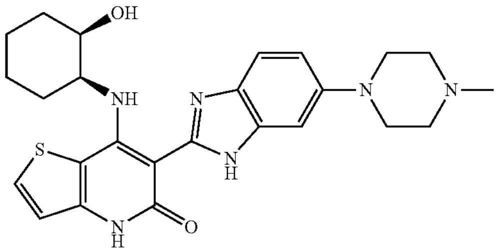 [SMILES: CN1CCN(c2ccc3nc(-c4c(N[C@H]5CCCC[C@H]5O)c5sccc5[nH]c4=O)[nH]c3c2)CC1] | 20 mg (21%), yellow solid; free base |

Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.20 mmol), (1R,2S)-2-aminocyclohexanol (0.091 g, 0.80 mmol), DMF (7 mL). MS ESI $[M + H]^+$ 731.2, calcd for $[C_{34}H_{37}F_3N_6O_5S_2 + H]^+$ 731.2.

Step 2: Reagents (general method D): 7-(((1S,2R)-2-hydroxycyclohexyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno-[3,2-b]pyridin-5(4H)-one (crude, 0.20 mmol), TFA (5 mL), HCl (1 mL). $^1$H NMR (400 MHz, $CD_3OD$) δ 7.84 (d, J = 5.8 Hz, 1H), 7.56-7.40 (m, 1H), 7.29-7.13 (m, 1H), 7.07 (d, J = 5.5 Hz, 1H), 7.03-6.94 (m, 1H), 4.56-4.46 (m, 1H), 4.15-4.04 (m, 1H), 3.27-3.13 (m, 4H), 2.79-2.64 (m, 4H), 2.41 (s, 3H), 2.14-1.95 (m, 2H), 1.91-1.74 (m, 4H), 1.60-1.44 (m, 2H); MS ESI $[M + H]^+$ 479.2, calcd for $[C_{25}H_{30}N_6O_2S + H]^+$ 479.2.

| Example/IUPAC name | Structure | Yield; description; salt |
|---|---|---|
| A45: 7-((1-methylpiperidin-4-yl)amino)-6-(6-morpholino-1H-benzo[d]imidazol-2-yl)thieno[3,2-b]pyridin-5(4H)-one | 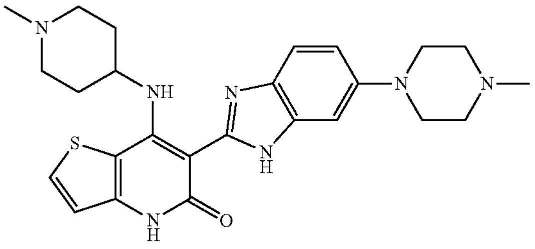 | 33 mg (30%), brown solid; free base |

Step 1: Reagents (general method C): 4-(4-methoxybenzyl)-6-(5 and/or 6-morpholino-1-((trifluoro-methyl)sulfonyl)-1H-benzo[d]imidazol-2-yl)-5-oxo-4,5-dihydrothieno[3,2-b]pyridin-7-yl trifluoro-methanesulfonate (crude, 0.20 mmol), tert-butyl 4-aminopiperidine-1-carboxylate (0.16 g, 0.8 mmol), DMF (7 mL). MS ESI $[M + H]^+$ 717.2, calcd for $[C_{33}H_{35}F_3N_6O_5S_2 + H]^+$ 717.2.

Step 2: Reagents (general method D): 4-(4-methoxybenzyl)-7-((1-methylpiperidin-4-yl)amino)-6-(5 and/or 6-morpholino-1-((trifluoromethyl)sulfonyl)-1H-benzo[d]imidazol-2-yl)thieno[3,2-b]pyridin-5(4H)-one (crude, 0.24 mmol), TFA (5 mL), HCl (1 mL). $^1$H NMR (400 MHz, $CD_3OD$) δ 7.91-7.84 (m, 1H), 7.53-7.43 (m, 1H), 7.22-7.13 (m, 1H), 7.08 (d, J = 5.5 Hz, 1H), 7.05-6.94 (m, 1H), 4.48-4.33 (m, 1H), 3.93-3.83 (m, 4H), 3.20-3.10 (m, 4H), 3.02-2.87 (m, 2H), 2.61-2.43 (m, 2H), 2.40 (s, 3H), 2.31-2.16 (m, 2H), 2.01-1.87 (m, 2H); MS ESI $[M + H]^+$ 465.2, calcd for $[C_{24}H_{28}N_6O_2S + H]^+$ 465.2.

-continued

| Example/IUPAC name | Structure | Yield; description; salt |
|---|---|---|
| A46: 7-(((1R,2S)-2-hydroxycyclohexyl)amino)-6-(6-(4-methylpiperazin-1-yl)-1H-benzo[d]imidazol-2-yl)thieno[3,2-b]pyridin-5(4H)-one | 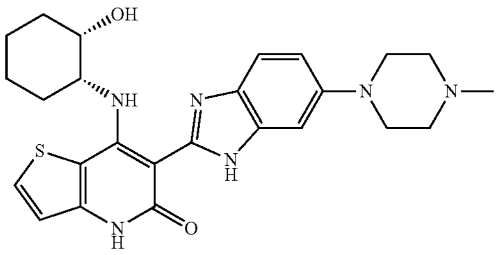 [SMILES: CN1CCN(c2ccc3nc(-c4c(N[C@@H]5CCCC[C@@H]5O)c5sccc5[nH]c4=O)[nH]c3c2)CC1] | 12 mg (4%), yellow solid; free base |

Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.20 mmol), (1S,2R)-2-aminocyclohexanol (0.091 g, 0.80 mmol), DMF (7 mL). MS ESI $[M + H]^+$ 731.2, calcd for $[C_{34}H_{37}F_3N_6O_5S_2 + H]^+$ 731.2.

Step 2: Reagents (general method D): 7-(((1R,2S)-2-hydroxycyclohexyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno-[3,2-b]pyridin-5(4H)-one (crude, 0.20 mmol), TFA (5 mL), HCl (1 mL). $^1H$ NMR (400 MHz, $CD_3OD$) δ 7.82 (d, J = 5.2 Hz, 1H), 7.55-7.38 (m, 1H), 7.29-7.10 (m, 1H), 7.05 (d, J = 5.5 Hz, 1H), 7.01-6.93 (m, 1H), 4.55-4.43 (m, 1H), 4.15-4.05 (m, 1H), 3.22 (br s, 4H), 2.70 (br s, 4H), 2.39 (s, 3H), 2.14-1.96 (m, 3H), 1.92-1.73 (m, 5H); MS ESI $[M + H]^+$ 479.2, calcd for $[C_{25}H_{30}N_6O_2S + H]^+$ 479.2

| Example/IUPAC name | Structure | Yield; description; salt |
|---|---|---|
| A47: 7-(cyclopentylamino)-6-(6-(3r,5s)-rel-3,4,5-trimethylpiper-azin-1-yl)-1H-benzo[d]imidazol-2-yl)thieno[3,2-b]pyridin-5(4H)-one | 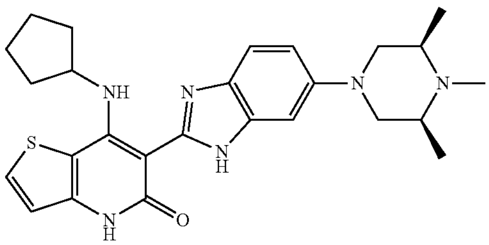 [SMILES: C[C@@H]1CN(c2ccc3nc(-c4c(NC5CCCC5)c5sccc5[nH]c4=O)[nH]c3c2)C[C@H](C)N1C] | 21 mg (18%); brown solid; TFA |

Step 1: Reagents (general method C): 4-(4-methoxybenzyl)-5-oxo-6-(1-((trifluoromethyl)sulfonyl)-5 and/or 6-((3r,5s)-rel-3,4,5-trimethylpiperazin-1-yl)-1H-benzo[d]imidazol-2-yl)-4,5-dihydrothieno[3,2-b]pyridin-7-yl trifluoromethanesulfonate (crude, 0.2 mmol), cyclopentylamine (0.1 mL), DMF (6 mL). MS ESI $[M + H]^+$ 729.2, calcd for $[C_{35}H_{39}F_3N_6O_4S_2 + H]^+$ 729.2.

Step 2: Reagents (general method D): 7-(cyclopentylamino)-4-(4-methoxybenzyl)-6-(1-((trifluoro-methyl)sulfonyl)-(5 and/or 6-((3s,5r)-rel-3,4,5-trimethylpiperazin-1-yl)-1H-benzo[d]imidazol-2-yl)-thieno[3,2-b]pyridin-5(4H)-one (crude, 0.2 mmol), TFA (6 mL), and conc. HCl (0.5 mL). $^1H$ NMR (400 MHz, $CD_3OD$) δ 7.94 (d, J = 5.6 Hz, 1H), 7.56 (d, J = 8.8 Hz, 1H), 7.26-7.23 (m, 1H), 7.18-7.14 (m, 1H), 7.09 (d, J = 5.6 Hz, 1H), 4.67-4.60 (m, 1H), 3.92-3.85 (m, 2H), 3.60-3.50 (m, 2H), 3.05-2.88 (m, 5H), 2.22-2.13 (m, 2H), 1.94-1.70 (m, 6H), 5.10 (d, J = 6.0 Hz, 6H); MS ESI $[M + H]^+$ 477.3, calcd for $[C_{26}H_{32}N_6OS + H]^+$ 477.2.

| Example/IUPAC name | Structure | Yield; description; salt |
|---|---|---|
| A48: 7-((tetrahydro-2H-pyran-4-yl)amino)-6-(6-(3r,5s)-rel-3,4,5-trimethylpiperazin-1-yl)-1H-benzo[d]imidazol-2-yl)thieno[3,2-b]pyridin-5(4H)-one | 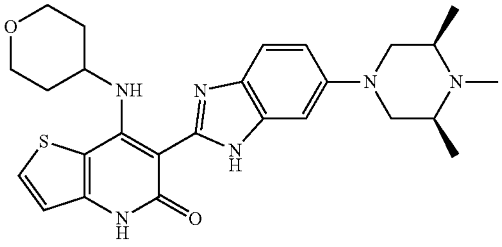 [SMILES: C[C@@H]1CN(c2ccc3nc(-c4c(NC5CCOCC5)c5sccc5[nH]c4=O)[nH]c3c2)C[C@H](C)N1C] | 19 mg (16%); yellow solid; TFA |

Step 1: Reagents (general method C): 4-(4-methoxybenzyl)-5-oxo-5 and/or 6-(1-((trifluoromethyl)-sulfonyl)-6-((3r,5s)-rel-3,4,5-trimethylpiperazin-1-yl)-1H-benzo[d]imidazol-2-yl)-4,5-dihydrothieno-[3,2-b]pyridin-7-yl trifluoromethanesulfonate (crude, 0.2 mmol), tetrahydro-2H-pyran-4-amine (0.1 mL), DMF (6 mL). MS ESI $[M + H]^+$ 745.1, calcd for $[C_{35}H_{39}F_3N_6O_5S_2 + H]^+$ 745.2.

Step 2: Reagents (general method D): 4-(4-methoxybenzyl)-7-((tetrahydro-2H-pyran-4-yl)amino)-(5 and/or 6-(1-((trifluoromethyl)sulfonyl)-6-((3s,5r)-rel-3,4,5-trimethylpiperazin-1-yl)-1H-benzo[d]imi-dazol-2-yl)thieno[3,2-b]pyridin-5(4H)-one (crude, 0.2 mmol) TFA (6 mL), and conc. HCl (0.5 mL). $^1H$ NMR (400 MHz, $CD_3OD$) δ 7.95 (d, J = 5.6 Hz, 1H), 7.60 (d, J = 8.8 Hz, 1H), 7.28 (d, J = 2.0 Hz, 1H), 7.21 (dd, J = 8.8, 1.6 Hz, 1H), 7.10 (d, J = 5.6 Hz, 1H), 4.40-4.30 (m, 1H), 4.08-4.02 (m, 2H), 3.95-3.87 (m, 2H), 3.63-3.53 (m, 4H), 3.03 (s, 3H), 3.02-2.93 (m, 2H), 2.18-2.11 (m, 2H), 1.86-1.76 (m, 2H), 1.52 (d, J= 6.4 Hz, 6H); MS ESI $[M + H]^+$ 493.3, calcd for $[C_{26}H_{32}N_6O_2S + H]^+$ 493.2.

-continued

| Example/IUPAC name | Structure | Yield; description; salt |
|---|---|---|
| A49: 6-(6-(4-methylpiperazin-1-yl)-1H-benzo[d]imidazol-2-yl)-7-morpholinothieno[3,2-b]pyridin-5(4H)-one | 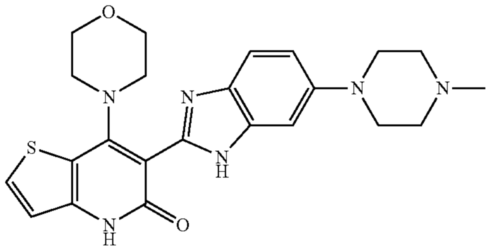 [SMILES: CN1CCN(c2ccc3nc(-c4c(N5CCOCC5)c5sccc5[nH]c4=O)[nH]c3c2)CC1] | 134 mg (79%); yellow solid; TFA salt |

Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.3 mmol), morpholine (0.08 mL, 0.897 mmol). MS ESI $[M + H]^+$ 703.2, calcd for $[C_{32}H_{33}F_3N_6O_5S_2 + H]^+$ 703.2.
Step 2: Reagents (general method D): 4-(4-methoxybenzyl)-6-(5 and/or 6-(4-methylpiperazin-1-yl)-1-((trifluoromethyl)sulfonyl)-1H-benzo[d]imidazol-2-yl)-7-morpholinothieno[3,2-b]pyridin-5(4H)-one (crude, 0.3 mmol), TFA (5 mL), conc. HCl (1 mL). $^1H$ NMR (400 MHz, DMSO-$d_6$) δ 12.46 (s, 1H), 9.98 (br. s, 1H), 8.17 (d, J = 5.6 Hz, 1H), 7.71 (d, J = 9.2 Hz, 1H), 7.33 (dd, J = 9.2, 1.2 Hz, 1H), 7.24 (d, J = 2.0 Hz, 1H), 7.08 (d, J = 5.6 Hz, 1H), 3.92-3.84 (m, 2H), 3.70-3.62 (m, 4H), 3.62-3.57 (m, 2H), 3.35-3.28 (m, 4H), 3.28-3.13 (m, 2H), 3.11-2.99 (m, 2H), 2.89 (s, 3H); MS ESI $[M + H]^+$ 451.3, calcd for $[C_{23}H_{26}N_6O_2S + H]^+$ 451.2.

| Example/IUPAC name | Structure | Yield; description; salt |
|---|---|---|
| A50: 7-(4-hydroxypiperidin-1-yl)-6-(6-(4-methylpiperazin-1-yl)-1H-benzo[d]imidazol-2-yl)thieno[3,2-b]pyridin-5(4H)-one | 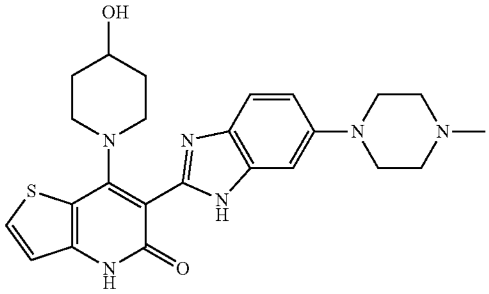 [SMILES: CN1CCN(c2ccc3nc(-c4c(N5CCC(O)CC5)c5sccc5[nH]c4=O)[nH]c3c2)CC1] | 126 mg (73%); yellow solid; TFA salt |

Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.30 mmol), piperidin-4-ol (91 mg, 0.897 mmol), TFA (4 mL), conc. HCl (1 mL). MS ESI $[M + H]^+$ 717.2, calcd for $[C_{33}H_{35}F_3N_6O_5S_2 + H]^+$ 717.2.
Step 2: Reagents (general method D): 7-(4-hydroxypiperidin-1-yl)-4-(4-methoxybenzyl)-6-(5 and/or 6-(4-methylpiperazin-1-yl)-1-((trifluoromethyl)sulfonyl)-1H-benzo[d]imidazol-2-yl)thieno[3,2-b]pyridin-5(4H)-one (crude, 0.3 mmol), TFA (5 mL), conc. HCl (1 mL). $^1H$ NMR (400 MHz, DMSO-$d_6$) δ 14.26 (br.s, 1H), 12.33 (s, 1H), 10.04 (br.s, 1H), 8.14 (s, 1H), 7.70 (d, J = 7.28 Hz, 1H), 7.36-7.28 (m, 1H), 7.23 (br.s., 1H), 7.06 (s, 1H), 3.98-3.83 (m, 2H), 3.75-3.66 (m, 2H), 3.66-3.39 (m, 3H), 3.25-3.10 (m, 4H), 3.10-2.97 (m, 2H), 2.73 (s, 3H), 1.86-1.72 (m, 2H), 1.54-1.39 (m, 2H); MS ESI $[M + H]^+$ 465.3, calcd for $[C_{24}H_{28}N_6O_2S + H]^+$ 465.2.

| Example/IUPAC name | Structure | Yield; description; salt |
|---|---|---|
| A51: 7-(((1R,2S)-2-hydroxycyclohexyl)amino)-6-(6-(4-methylpiperazin-1-yl)-1H-benzo[d]imidazol-2-yl)thieno[3,2-b]pyridin-5(4H)-one | 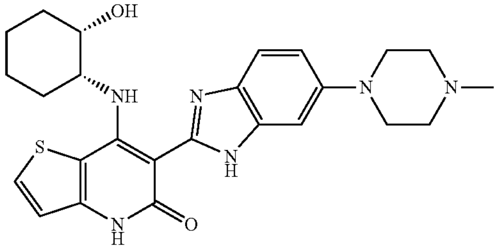 [SMILES: CN1CCN(c2ccc3nc(-c4c(N[C@@H]5CCCC[C@@H]5O)c5sccc5[nH]c4=O)[nH]c3c2)CC1] | 15 mg (15%), yellow solid; free base |

Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.20 mmol), (1S,2R)-2-aminocyclohexanol (0.091 g, 0.80 mmol), DMF (7 mL). MS ESI $[M + H]^+$ 731.2; calcd for $[C_{34}H_{37}F_3N_6O_5S_2 + H]^+$ 731.2.
Step 2: Reagents (Genral Method D): 7-(((1R,2S)-2-hydroxycyclohexyl)amino)-4-(4-methoxybenzyl)-6-(5 and/or 6-(4-methylpiperazin-1-yl)-1-((trifluoromethyl)sulfonyl)-1H-benzo[d]imidazol-2-yl)thieno-[3,2-b]pyridin-5(4H)-one (crude, 0.20 mmol), TFA (5 mL), HCl (1 mL) $^1H$ NMR (400 MHz, MeOD-$d_4$) δ 7.82 (d, J = 5.2 Hz, 1H), 7.55-7.38 (m, 1H), 7.29-7.10 (m, 1H), 7.05 (d, J = 5.5 Hz, 1H), 7.01-6.93 (m, 1H), 4.55-4.43 (m, 1H), 4.15-4.05 (m, -continued

| Example/IUPAC name | Structure | Yield; description; salt |
|---|---|---|
| 1H), 3.22 (br s, 4H), 2.70 (br s, 4H), 2.39 (s, 3H), 2.14-1.96 (m, 3H), 1.92-1.73 (m, 5H); MS ESI $[M + H]^+$ 479.2; calcd for $[C_{25}H_{30}N_6O_2S + H]^+$ 479.2. | | |
| A52: 6-(6-(4-methylpiperazin-1-yl)-1H-benzo[d]imidazol-2-yl)-7-((pyridin-3-ylmethyl)amino)thieno[3,2-b]pyridin-5(4H)-one | 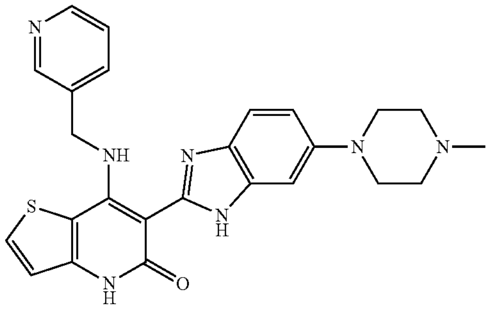 [SMILES: CN1CCN(c2ccc3nc(-c4c(NCc5cccnc5)c5sccc5[nH]c4=O)[nH]c3c2)CC1] | 57 mg (27%); yellow solid; TFA salt |
| Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7- yl trifluoromethanesulfonate (crude, 0.3 mmol), pyridin-3-ylmethanamine (0.09 mL, 0.90 mmol). MS ESI $[M + H]^+$ 724.2, calcd for $[C_{34}H_{32}F_3N_7O_4S_2 + H]^+$ 724.2. Step 2: Reagents (general method D): 4-(4-methoxybenzyl)-6-(5 and/or 6-(4-methylpiperazin-1-yl)-1-((trifluoromethyl)sulfonyl)-1H-benzo[d]imidazol-2-yl)-7-((pyridin-3-ylmethyl)amino)thieno[3,2-b]pyridin-5(4H)-one (crude, 0.3 mmol), TFA (4 mL), conc. HCl (1 mL). $^1H$ NMR (400 MHz, $CD_3OD$) δ 8.92-8.81 (m, 1H), 8.78-8.67 (m, 1H), 8.56-8.45 (m, 1H), 8.00-7.85 (m, 2H), 7.62-7.50 (m, 1H), 7.30-7.21 (m, 1H), 7.20-7.13 (m, 1H), 7.12-7.03 (m, 1H), 5.31 (s, 2H), 3.91-3.77 (m, 2H), 3.73-3.57 (m, 2H), 3.41-3.22 (m, 2H), 3.20-3.07 (m, 2H), 3.01 (s, 3H); MS ESI $[M + H]^+$ 472.3, calcd for $[C_{25}H_{25}N_7OS + H]^+$ 472.2. | | |
| A53; 6-(6-(4-methylpiperazin-1-yl)-1H-benzo[d]imidazol-2-yl)-7-((pyridin-2-ylmethyl)amino)-thieno[3,2-b]pyridin-5(4H)-one | 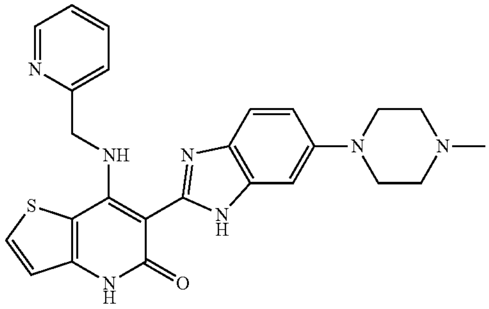 [SMILES: CN1CCN(c2ccc3nc(-c4c(NCc5ccccn5)c5sccc5[nH]c4=O)[nH]c3c2)CC1] | 100 mg (48%); yellow solid; TFA salt |
| Step 1: Reagents (general method C): 4-(4-methoxybenzyl)-6-(5 and/or 6-(4-methylpiperazin-1-yl)-1-((trifluoromethyl)sulfonyl)-1H-benzo[d]imidazol-2-yl)-5-oxo-4,5-dihydrothieno[3,2-b]pyridin-7-yl trifluoromethanesulfonate (crude, 0.3 mmol), pyridin-2-ylmethanamine (0.09 mL, 0.897 mmol). MS ESI $[M + H]^+$ 724.2, calcd for $[C_{34}H_{32}F_3N_7O_4S_2 + H]^+$ 724.2. Step 2: Reagents (general method D): 4-(4-methoxybenzyl)-6-(5 and/or 6-(4-methylpiperazin-1-yl)-1-((trifluoromethyl)sulfonyl)-1H-benzo[d]imidazol-2-yl)-7-((pyridin-2-ylmethyl)amino)thieno[3,2-b]pyridin-5(4H)-one (crude, 0.3 mmol), TFA (4 mL), conc. HCl (1 mL). $^1H$ NMR (400 MHz, $CD_3OD$) δ 8.67 (d, J = 5.5 Hz, 1H), 8.05 (t, J = 7.4 Hz, 1H), 7.94 (d, J = 5.5 Hz, 1H), 7.68 (d, J = 7.5 Hz, 1H), 7.63 (d, J = 8.8 Hz, 1H), 7.58-7.51 (m, 1H), 7.25-7.21 (m, 2H), 7.08 (d, J = 5.5 Hz, 1H), 5.25 (s, 2H), 3.95-3.84 (m, 2H), 3.72-3.62 (m, 2H), 3.41-3.33 (m, 2H), 3.21-3.10 (m, 2H), 3.01 (m, 3H). MS ESI $[M + H]^+$ 472.3, calcd for $[C_{25}H_{25}N_7OS + H]^+$ 472.2. | | |

| Example/IUPAC name | Structure | Yield; description; salt |
|---|---|---|
| A54: 4-(((3S,4S)-3-fluoropiperidin-4-yl)amino)-5-(6-(4-methylpiperazin-1-yl)-1H-benzo[d]imidazol-2-yl)thieno[2,3-b]pyridin-6(7H)-one | 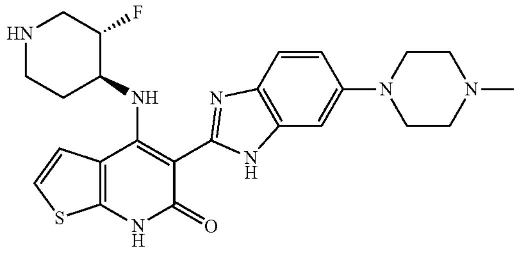 [SMILES: CN1CCN(c2ccc3nc(-c4c(N[C@H]5CCNC[C@@H]5F)c5ccsc5[nH]c4=O)[nH]c3c2)CC1] | 113 mg (53%); yellow solid; 2 TFA |
| Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.23 g, 0.30 mmol), (3S,4S)-tert-butyl 4-amino-3-fluoropiperidine-1-carboxylate (0.20 g, 0.90 mmol), DMF (5 mL). MS ESI $[M - CF_3O_2S + 2H]^+$ 702.2, calcd for $[C_{37}H_{44}FN_7O_4S + H]^+$ 702.32.<br>Step 2: Reagents (general method D): a mixture of (3S,4S)-tert-butyl 3-fluoro-4-((7-(4-methoxybenzyl)-5-(5 and/or 6-(4-methylpiperazin-1-yl)-1-((trifluoromethyl)sulfonyl)-1H-benzo[d]imi-dazol-2-yl)-6-oxo-6,7-dihydrothieno[2,3-b]pyridin-4-yl)amino)piperidine-1-carboxylate (0.23 g, 0.30 mmol), TFA (7 mL), and conc. HCl (1 mL). $^1$H NMR (400 MHz, $CD_3OD$) δ 7.55 (d, J = 8.8 Hz, 1H), 7.48 (d, J = 6.0 Hz, 1H), 72.4-7.16 (m, 2H), 7.10 (d, J = 8.4 Hz, 1H), 5.12-5.07 (m, 1H), 5.03-4.99 (m, 2H), 4.41 (br.s, 1H), 3.90-3.56 (m, 6H), 3.52-3.43 (m, 1H), 3.32-3.27 (m, 1H), 3.23-3.09 (m, 2H), 3.01 (s, 3H), 2.52-2.41 (m, 1H), 2.21-2.09 (m, 1H); MS ESI $[M + H]^+$ 482.2, calcd for $[C_{24}H_{28}FN_7OS + H]^+$ 482.2. | | |
| A55: 4-(((3R*,4S*)-3-fluoropiperidin-4-yl)amino)-5-(6-(4-methylpiperazin-1-yl)-1H-benzo[d]imidazol-2-yl)thieno[2,3-b]pyridin-6(7H)-one | 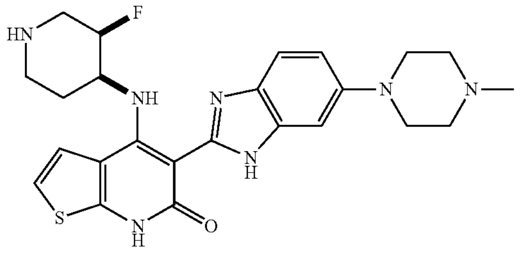 | 114 mg (54%); brown solid; 2 TFA |
| Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.23 g, 0.30 mmol), (3R*,4S*)-tert-butyl 4-amino-3-fluoropiperidine-1-carboxylate (0.20 g, 0.90 mmol), DMF (5 mL). MS ESI $[M - CF_3O_2S + 2H]^+$ 702.2, calcd for $[C_{37}H_{44}FN_7O_4S + H]^+$ 702.32.<br>Step 2: Reagents (general method D): a mixture of (3R*,4S*)-tert-butyl 3-fluoro-4-((7-(4-methoxybenzyl)-5-(5 and/or 6-(4-methylpiperazin-1-yl)-1-((trifluoromethyl)sulfonyl)-1H-benzo[d]imi-dazol-2-yl)-6-oxo-6,7-dihydrothieno[2,3-b]pyridin-4-yl)amino)piperidine-1-carboxylate (0.23 g, 0.30 mmol), TFA (7 mL), and conc. HCl (1 mL). $^1$H NMR (400 MHz, $CD_3OD$) δ 7.57 (d, J = 8.8 Hz, 1H), 7.52 (d, J = 6.0 Hz, 1H), 7.24 (d, J = 2.1 Hz, 1H), 7.21 (d, J = 5.9 Hz, 1H), 7.15 (dd, J = 2.1, 8.9 Hz, 1H), 5.19 (d, J = 46.7 Hz, 1H), 4.43-4.27 (m, 1H), 3.78 (d, J = 12.6 Hz, 3H), 3.72-3.57 (m, 2H), 3.49 (d, J = 13.9 Hz, 2 H), 3.41 (d, J = 14.2 Hz, 1H), 3.23 (d, J = 3.5 Hz, 4H), 3.00 (s, 3H), 2.42-2.23 (m, 2H); MS ESI $[M + H]^+$ 482.2, calcd for $[C_{24}H_{28}FN_7OS + H]^+$ 482.2. | | |
| A56: 4-amino-5-(5-fluoro-6-morpholino-1H-benzo[d]-imidazol-2-yl)-thieno-[2,3b]-pyridin-6(7H)-one | 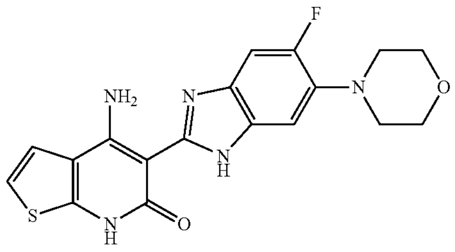 [SMILES: Nc1c(-c2nc3cc(F)c(N4CCOCC4)cc3[nH]2)c(=O)[nH]c2sccc12] | 4- mg (16%); Light brown solid HCl |
| Reagents (general method-A1): ethyl 2-(5-fluoro-6-morpholino-1H-benzo[d]imidazol-2-yl)acetate (186 mg, 0.60 mmol), 2-amino-2-cyanothiophene (75 mg, 0.60 mmol), LDA (3.0 mL, 1 M in THF/hex, 3.0 mmol) anh THF (6.0 mL); $^1$H NMR (400 MHz, $CD_3OD$) δ 7.58 (d, J = 11.6 Hz, 1H), 7.55-7.51 (m, 2H), 7.21 (d, J = 6.0 Hz, 1H), 3.97-3.94 (m, 4H), 3.30-3.27 (m, 4H); MS ESI $[M + H]^+$ 386.2, calcd for $[C_{18}H_{16}FN_5O_2S + H]^+$ 386.1. | | |

-continued

| Example/IUPAC name | Structure | Yield; description; salt |
|---|---|---|
| A57: 4-(((1S,2R)-2-hydroxy-cyclohexyl)amino)-5-(6-(4-methylpiperazin-1-yl)-1H-benzo[d]imidazol-2-yl)thieno-[2,3-b]pyridin-6(7H)-one | 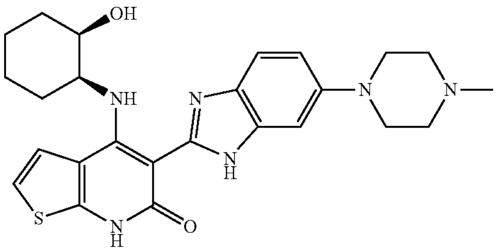 [SMILES: CN1CCN(c2ccc3nc(-c4c(N[C@H]5CCCC[C@H]5O)c5ccsc5[nH]c4=O)[nH]c3c2)CC1] | 36 mg (25%), Yellow solid; Free base |
| Step 1: (General Method C) 7-(4-methoxybenzyl)-5-(5 and/or 6-(4-methylpiperazin-1-yl)-1-((trifluoro-methyl)-sulfonyl)-1H-benzo[d]imidazol-2-yl)-6-oxo-6,7-dihydrothieno[2,3-b]pyridin-4-yl trifluoro-methanesulfonate (crude, 0.30 mmol), (1R,2S)-2-aminocyclohexanol (0.14 g, 1.2 mmol), DMF (7 mL). MS ESI $[M + H]^+$ 731.2, calcd for $[C_{34}H_{37}F_3N_6O_5S_2 + H]^+$ calcd 731.2<br>Step 2: (General Method D) 4-(((1S,2R)-2-hydroxycyclohexyl)amino)-7-(4-methoxybenzyl)-5-(5 and/or 6-(4-methylpiperazin-1-yl)-1-((trifluoromethyl)sulfonyl)-1H-benzo[d]imidazol-2-yl)thieno[2,3-b]pyridin-6(7H)-one (crude, 0.30 mmol), TFA (5 mL), HCl (1 mL); $^1$H NMR (400 MHz, MeOD-$d_4$) δ ppm 7.53 (d, J = 5.99 Hz, 1 H), 7.48 (br. s, 1 H), 7.20 (br. s., 1 H), 7.12 (d, J = 5.99 Hz, 1 H), 6.97-7.04 (m, 1 H), 4.38-4.47 (m, 1 H), 4.04-4.11 (m, 1 H), 3.19-3.28 (m, 4 H), 2.65-2.75 (m, 4 H), 2.40 (s, 3 H), 2.08-2.17 (m, 1 H), 2.00-2.08 (m, 1 H), 1.75-1.90 (m, 4 H), 1.46-1.61 (m, 2 H); MS ESI $[M + H]^+$ 479.2, calcd for $[C_{25}H_{30}N_6O_2S + H]^+$ 479.2. | | |
| A58: 4-(((1S,2R)-2-hydroxy-cyclopentyl)amino)-5-(6-(4-methylpiperazin-1-yl)-1H-benzo[d]imidazol-2-yl)-thieno[2,3-b]pyridin-6(7H)-one | 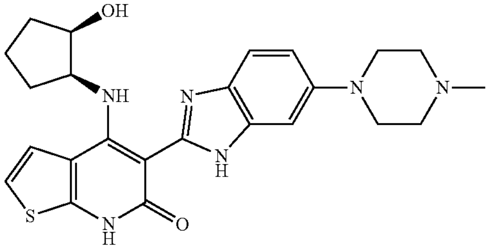 [SMILES: CN1CCN(c2ccc3nc(-c4c(N[C@H]5CCC[C@H]5O)c5ccsc5[nH]c4=O)[nH]c3c2)CC1] | 23 mg (17%), yellow solid; Free base |
| Step 1: (general method C) 7-(4-methoxybenzyl)-5-(5 and/or 6-(4-methylpiperazin-1-yl)-1-((trifluoromethyl)-sulfonyl)-1H-benzo[d]imidazol-2-yl)-6-oxo-6,7-dihydrothieno[2,3-b]pyridin-4-yl trifluoromethane-sulfonate (crude, 0.30 mmol), (1R,2S)-2-aminocyclopentanol (0.10 g, 1.2 mmol), DMF (7 mL). MS ESI $[C_{33}H_{35}F_3N_6O_5S_2 + H]^+$ calcd 717.2, observed 717.2<br>Step 2: (General Method D) 4-(((1S,2R)-2-hydroxycyclopentyl)amino)-7-(4-methoxybenzyl)-5-(5 and/or 6-(4-methylpiperazin-1-yl)-1-((trifluoromethyl)sulfonyl)-1H-benzo[d]imidazol-2-yl)thieno[2,3-b]pyridin-6(7H)-one (crude, 0.30 mmol), TFA (5 mL), HCl (1 mL); $^1$H NMR (400 MHz, MeOD-$d_4$) δ ppm 7.55 (d, J = 5.99 Hz, 1H), 7.42-7.51 (m, 1 H), 7.12-7.25 (m, 1 H), 7.09 (d, J = 5.87 Hz, 1 H), 6.94-7.01 (m, 1 H), 4.43-4.51 (m, 1 H), 4.32-4.39 (m, 1 H), 3.16-3.26 (m, 4 H), 2.62-2.74 (m, 4 H), 2.38 (s, 3 H), 2.17-2.26 (m, 1 H), 1.89-2.15 (m, 4 H), 1.69-1.81 (m, 1 H); MS ESI $[M + H]^+$ 465.2, calcd for $[C_{24}H_{28}N_6O_2S + H]^+$ 465.2 | | |
| A59: 4-amino-5-(6-(4-methyl-1,4-diazepan-1-yl)-1H-benzo-[d]imidazol-2-yl)thieno[2,3-b]pyridin-6(7H)-one | 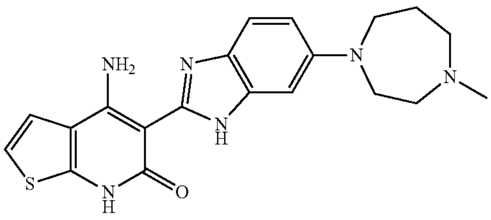 [SMILES: CN1CCCN(c2ccc3nc(-c4c(N)c5ccsc5[nH]c4=O)[nH]c3c2)CC1] | 28 mg (7%); brown solid; TFA |
| Reagents (General method A2): ethyl 2-(6-(4-methyl-1,4-diazepan-1-yl)-1H-benzo[d]imidazol-2-yl)acetate (255 mg, 0.8 mmol), 2-aminothiophene-3-carbonitrile (100 mg, 0.8 mmol), LDA (1.0 M in THF/hex, 4 mL, 4 mmol), THF 10 mL), 45° C., 2 h. 82 mg of mixture of uncyclized and cyclized was obtained which was recyclized with KOBu$^t$ (1.0 M in THF, 1.0 mL, 1 mmol) in THF (10 mL), rt, 30 min then 35° C., 1 h; $^1$H NMR (400 MHz, $CD_3OD$) δ 6.23 (d, J = 9.2 Hz, 1H), 7.52 (d, J = 5.6 Hz, 1H), 7.19 (d, J = 5.6 Hz, 1H), 7.14 (dd, J = 9.0, 2.2 Hz, 1H), 7.03 (d, J = 2.0 Hz, 1H), 4.00-3.30 (m, 8H), 3.00 (s, 3H), 2.40-2.30 (m, 2H); MS ESI $[M + H]^+$ 395.5, calcd for $[C_{20}H_{22}N_6OS + H]^+$ 395.2 | | |

The following compounds were prepared according to the general method A3.

A60: 4-amino-5-(5-(4-methylpiperazine-1-carbonyl)-1H-benzo[d]imidazol-2-yl)thieno[2,3-b]-pyridin-6(7H)-one

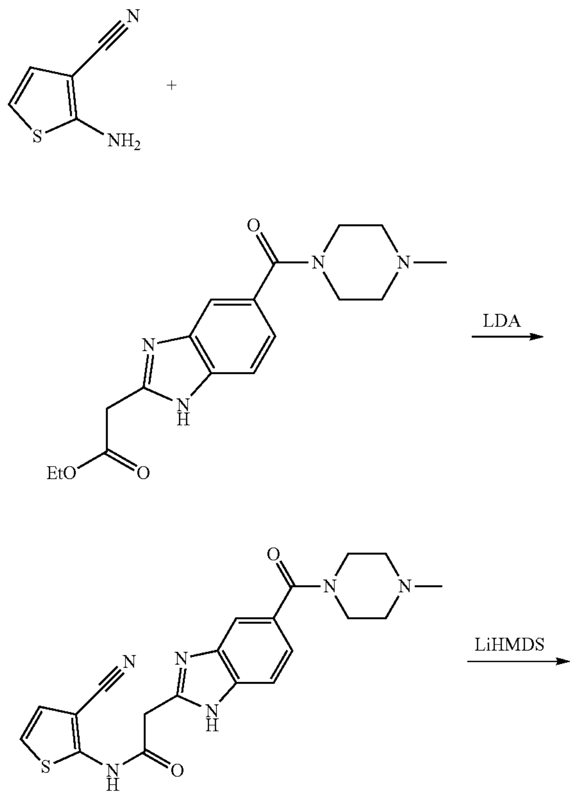

-continued

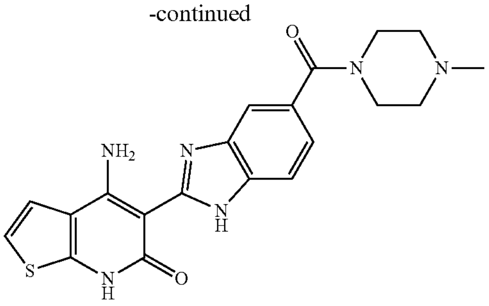

LDA (1.0 M in THF/hexanes, 2.3 mL, 2.3 mmol) was added dropwise over 15 min at rt to a stirred suspension of ethyl 2-(6-(4-methylpiperazine-1-carbonyl)-1H-benzo[d]imidazol-2-yl)acetate (0.150 g, 0.45 mmol) and 2-aminothiophene-3-carbonitrile (0.056 g, 0.45 mmol) in anh. THF (20 mL) under Ar. The addition was done initially at rt and after 5 minutes at 35° C. The heating was continued at 35° C. for 1 h before the reaction mixture was cooled to rt, quenched with aq $NH_4Cl$ and concentrated under reduced pressure. Purification by RP HPLC afforded N-(3-cyanothiophen-2-yl)-2-(5-(4-methylpiperazine-1-carbonyl)-1H-benzo[d]imidazol-2-yl)acetamide*TFA as a light brown solid (82 mg, 35%). $^1$H NMR (400 MHz, $CD_3OD$) δ 7.96 (s, 1H), 7.89 (d, J=8.5 Hz, 1H), 7.68 (dd, J=8.4, 1.4 Hz, 1H), 7.09-7.14 (m, 2H), 3.25-3.81 (m, 8H), 2.97 (s, 3H).

Step 2. The product of the previous reaction was filtered through PoraPak (2 g, using MeOH then 2 M $NH_3$ in MeOH) and dried. An anh THF (12 mL) solution of the material (0.055 g, 0.13 mmol) under Ar was treated with LiHMDS (1.0 M in THF, 0.7 mL, 0.7 mmol) over 3 min at rt stirred for 10 min and heated at 45° C. for 95 min. The reaction was then cooled to rt, quenched with aq NH4Cl, concentrated under reduced pressure and purified by prep HPLC. Filtration through PoraPak (2 g) and trituration with $CH_2Cl_2$ afforded the title compound as a light yellow solid 3.6 mg (3%). $^1$H NMR (400 MHz, $CD_3OD$) δ 7.58-7.77 (m, 2H), 7.51 (d, J=5.80 Hz, 1H), 7.30 (dd, J=8.30, 1.30 Hz, 1H), 7.14 (d, J=5.80 Hz, 1H), 3.53-3.92 (m, 4H), 2.48-2.70 (m, 4H), 2.43 (s, 3H). MS ESI $[M+H]^+$ 409.2, calcd for $[C_{20}H_{20}N_6O_2S+H]^+$ 409.2.

| Example/IUPAC name | Structure | Yield; description; salt |
|---|---|---|
| A61: 4-amino-5-(6-methyl-5-(4-methylpiperazin-1-yl)-1H-benzo[d]imidazol-2-yl)thieno[2,3-b]pyridin-6(7H)-one | 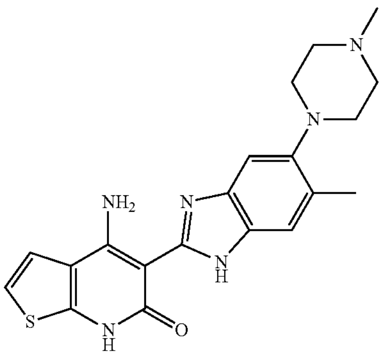 [SMILES: Cc1cc2[nH]c(-c3c(N)c4ccsc4[nH]c3=O)nc2cc1N1CCN(C)CC1] | 19 mg (7%); Orange-tan solid; TFA |

Reagents (method A3): Step 1: ethyl 2-(5-methyl-6-(4-methylpiperazin-1-yl)-1H-benzo[d]imidazol-2-yl)acetate (0.17 g, 0.53 mmol), 2-aminothiophene-3-carbonitrile (72 mg, 0.53 mmol), LDA (1.0 M in THF/hexanes, 1.7 mL, 1.7 mmol) in anh THF (12 mL). Step 2: LiHMDS (1.0 M in THF, 1.7 mL, 1.7 mmol) in anh THF (20 mL).
$^1$H NMR (400 MHz, $CD_3OD$) δ 7.48 (d, J = 5.77 Hz, 1 H), 7.44 (s, 1 H), 7.38 (s, 1 H), 7.12 (d, J = 5.77 Hz, 1 H), 3.58-3.59 (m, 2 H), 3.43-3.23 (m., 4 H), 3.07-3.22 (m, 2 H), 3.01 (s, 3 H), 2.45 (s, 3 H). MS ESI [M + H]$^+$ 395.1, calcd for $[C_{20}H_{22}N_6OS + H]$+ 395.2.

-continued

| Example/IUPAC name | Structure | Yield; description; salt |
| --- | --- | --- |
| A62: 4-amino-5-(5-(morpholine-4-carbonyl)-1H-benzo-[d]imidazol-2-yl)thieno[2,3-b]pyridin-6(7H)-one | 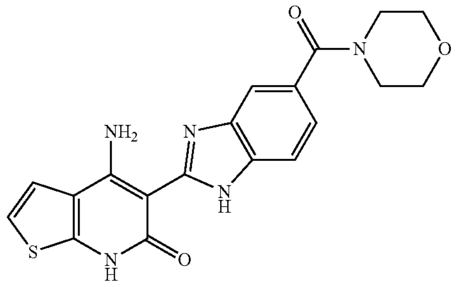 [SMILES: Nc1c(-c2nc3cc(C(=O)N4CCOCC4)ccc3[nH]2)c(=O)[nH]c2sccc12] | 6.5 mg (2%); white solid; free base |
| Reagents (method A3): Step 1: ethyl 2-(6-(morpholine-4-carbonyl)-1H-benzo[d]imidazol-2-yl)acetate (0.22 g, 0.70 mmol) and 2-aminothiophene-3-carbonitrile (84 mg, 0.70 mmol), LiHMDS (1.0 M in THF, 3.5 mL, 3.5 mmol) in anh. THF (24 mL). Step 2: LiHMDS (1.0 M in THF, 1.2 mL, 1.2 mmol) in anh THF (20 mL). $^1$H NMR (400 MHz, $CD_3OD$) δ 7.63-7.76 (m, 2 H), 7.48-7.52 (m, 1 H), 7.31 (dd, J = 8.30, 1.50 Hz, 1 H), 7.14 (d, J = 5.77 Hz, 1 H), 3.58-3.88 (m, 8 H). MS ESI $[M + H]^+$ 396.2, calcd for $[C_{19}H_{17}N_5O_3S + H]^+$ 396.1 | | |

A63: 7-(cyclopropylamino)-6-(6-(4-methylpiperazin-1-yl)-1H-benzo[d]imidazol-2-yl)thieno[3,2-b]-pyridin-5(4H)-one 2,2,2-trifluroaceatate

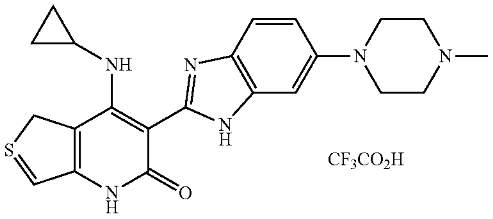

A suspension of 7-hydroxy-6-(6-(4-methylpiperazin-1-yl)-1H-benzo [d]imidazol-2-yl)thieno[3,2-b]pyridin-5(4H)-one (58 mg, 0.152 mmol) in anhydrous DCM (1 mL) was added Tf2O (0.55 mL, 0.916 mmol) dropwise at rt. The resulting reaction mixture was stirred at rt overnight before addition of cyclopropanamine (100 mg, 1.83 mmol) at 0° C. dropwise. The resulting reaction mixture was stirred at 40° C. overnight and diluted with DCM followed by washing with satd $NaHCO_3$. The organic layer was dried over $Na_2SO_4$, filtered, and concentrated to dryness. The residue was dissolved in MeOH and run through PoraPak followed by removal of solvent under reduced pressure. The crude product was purified by prep HPLC to give the title compound as a yellow solid (5 mg, 6% yield). $^1$H NMR (400 MHz, $CD_3OD$) δ 7.98 (d, J=5.5 Hz, 1H), 7.61 (d, J=9.0 Hz, 1H), 7.26 (d, J=2.0 Hz, 1H), 7.21 (dd, J=8.4, 2.0 Hz, 1H), 7.10 (d, J=5.5 Hz, 1H), 3.92-3.84 (m, 2H), 3.71-3.62 (m, 2H), 3.41-3.36 (m, 2H), 3.20-3.10 (m, 2H), 3.09-3.03 (m, 1H), 3.01 (s, 3H), 1.04-0.96 (m, 2H), 0.93-0.89 (m, 2H); MS ESI $[M+H]^+$ 421.2, calcd for $[C_{22}H_{24}N_6OS+H]^+$ 421.2.

A64: 4-amino-5-(6-(piperazin-1-yl)-1H-benzo[d]imidazol-2-yl)thieno[2,3-]pyridin-6(7H)-one tert-butyl 4-(3-amino-4-nitrophenyl)piperazine-1-carboxylate

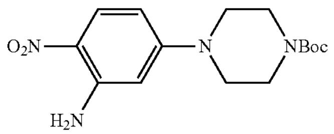

A mixture of 5-chloro-2-nitroaniline (2.5 g, 14.48 mmol), tert-butyl piperazine-1-carboxylate (3.24 g, 17.38 mmol) and $K_2CO_3$ (4.0 g, 28.96 mmol) in DMSO (100 mL) was stirred at 100° C. for 3 days. $H_2O$ (150 mL) was then added with stirring, suction filtered, rinsed with $H_2O$ and dried to give the title compound as a brown solid (2.6 g, 57%). $^1$H NMR (400 MHz, $CDCl_3$) δ 8.04 (d, J=9.79 Hz, 1H), 6.27 (dd, J=9.66, 2.64 Hz, 1H), 6.21-6.11 (m, 2H), 5.95 (d, J=2.51 Hz, 1H), 3.61-3.54 (m, 4H), 3.40-3.34 (m, 4H), 1.50 (s, 9H); MS ESI $[M+H]^-$ 323.2, calcd for $[C_{15}H_{22}N_4O_4+H]^+$ 323.2.

tert-butyl 4-(3,4-diaminophenyl)piperazine-1-carboxylate

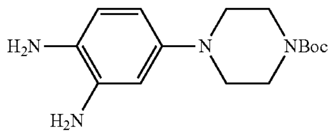

To a suspension of tert-butyl 4-(3-amino-4-nitrophenyl)piperazine-1-carboxylate (2.6 g, 8.04 mmol) in MeOH (150 mL) was added 10% Pd/C (130 mg, 5% wt.). The resulting mixture was hydrogenated under $H_2$ balloon O/N. The resulting reaction mixture was filtered, concentrated and dried to give the title compound as a dark brown solid (2.29 g, 97%). $^1$H NMR (400 MHz, $CDCl_3$) δ 6.66 (d, J=8.28 Hz, 1H), 6.39 (d, J=2.51 Hz, 1H), 6.34 (dd, J=8.28, 2.51 Hz, 1H), 3.60-3.53 (m, 4H), 3.46-3.23 (m, 4H), 3.02-2.95 (m, 4H), 1.49 (s, 9H); MS ESI $[M+H]^+$ 293.1, calcd for $[C_{15}H_{24}N_4O_2+H]^+$ 293.2.

tert-butyl 4-(2-(2-ethoxy-2-oxoethyl)-1H-benzo[d]imidazol-6-yl)piperazine-1-carboxylate To a solution of tert-butyl 4-(3,4-diaminophenyl)piperazine-1-carboxylate (100 mg, 0.34 mmol) in EtOH (3 mL) was added ethyl 3-ethoxy-3-iminopropionate hydrochloride (190 mg, 0.68 mmol). The resulting mixture was heated at 60° C. for 3 h. After removal of solvents, it was diluted with DCM (10 mL), adjust pH≈8 with satd $NaHCO_3$ and separated. The aqueous was extracted with DCM (10 mL×2) and the combined extracts were dried over $NaSO_4$, then concentrated and purified by flash chromatography (gradient: 100% EtOAc, then MeOH/DCM 0-20%) to give the title compound as a dark orange solid (116 mg, 87%). $^1H$ NMR (400 MHz, $CD_3OD$) δ 7.49-7.40 (m, 1H), 7.15-7.10 (m, 2H), 4.22 (q, J=7.11 Hz, 2H), 3.95 (s, 1H), 3.61 (br.s., 4H), 3.11 (br.s., 4H), 1.50 (s, 9H), 1.28 (t, J=7.15 Hz, 3H); MS ESI $[M+H]^+$ 389.2, calcd for $[C_{20}H_{28}N_4O_4+H]^+$ 389.2.

tert-butyl 4-(2-(4-amino-6-oxo-6,7-dihydrothieno[2,3-b]pyridin-5-yl)-1H-benzo[d]imidazol-6-yl)piperazine-1-carboxylate

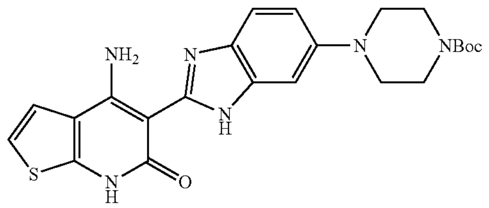 [SMILES: CC(C)(C)OC(=O)N1CCN(c2ccc3nc(-c4c(N)c5ccsc5[nH]c4=O)[nH]c3c2)CC1]

According to general method A, to a solution of 2-amino-4-ethoxythiophene-3-carbonitrile (64 mg, 0.52 mmol), tert-butyl 4-(2-(2-ethoxy-2-oxoethyl)-1H-benzo[d]imidazol-6-yl)piperazine-1-carboxylate (200 mg, 0.52 mmol), LiHMDS (1 M in THF, 2.0 mL, 2.06 mmol)) were used to generate the title compound as a light brown solid (88 mg, 35%). $^1H$ NMR (500 MHz, DMSO-$d_6$) δ 12.72-12.61 (m, 1H), 12.13-12.02 (m, 1H), 10.72-10.55 (m, 1H), 8.01-7.93 (m, 1H), 7.57 (d, J=5.62 Hz, 1H), 7.52-7.43 (m, 1H), 7.24-7.10 (m, 2H), 6.93-6.87 (m, 1H), 3.52-3.44 (m, 4H), 3.07-3.00 (m, 4H), 1.45-1.40 (m, 9H); MS ESI $[M+H]^+$ 467.2, calcd for $[C_{23}H_{26}N_6O_3S+H]^+$ 467.2.

4-amino-5-(6-(piperazin-1-yl)-1H-benzo[d]imidazol-2-yl)thieno[2,3-b]pyridin-6(7H)-one

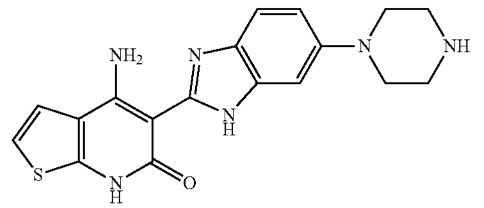 [SMILES: Nc1c(-c2nc3ccc(N4CCNCC4)cc3[nH]2)c(=O)[nH]c2sccc12]

A mixture of tert-butyl 4-(2-(4-amino-6-oxo-6,7-dihydrothieno[2,3-b]pyridin-5-yl)-1H-benzo[d]imidazol-6-yl)piperazine-1-carboxylate (83 mg, 0.178 mmol) in TFA (1 mL) was stirred at rt for 2 h before concentrated. The residue was dissolved in MeOH (20 mL) and run through PoraPak then concentrated to give the title compound as a yellow solid (45 mg, 69%). $^1H$ NMR (400 MHz, DMSO-$d_6$) δ 12.65-12.58 (m, 1H), 10.77-10.61 (m, 1H), 8.03-7.94 (m, 1H), 7.59 (d, J=5.77 Hz, 1H), 7.54-7.42 (m, 1H), 7.19-7.10 (m, 2H), 6.92-6.86 (m, 1H), 3.09-3.01 (m, 4H), 2.94-2.88 (m, 4H); the signal due to $NH_2$ cannot be readily detected. MS ESI $[M+H]^+$ 367.2, calcd for $[C_{18}H_{18}N_6OS+H]-$ 367.1.

A65: 4-amino-5-(6-(4-(oxetan-3-yl)piperazin-1-yl)-1H-benzo[d]imidazol-2-yl)thieno[2,3-b]pyridin-6(7H)-one

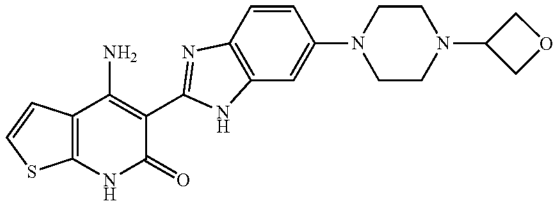 [SMILES: Nc1c(-c2nc3ccc(N4CCN(C5COC5)CC4)cc3[nH]2)c(=O)[nH]c2sccc12]

A mixture of 4-amino-5-(6-(piperazin-1-yl)-1H-benzo[d]imidazol-2-yl)thieno[2,3-b]pyridin-6(7H)-one (45 mg, 0.123 mmol), oxetan-3-one (8.8 mg, 0.123 mmol), and $NaBH(OAc)_3$ (120 mg, 0.552 mmol) in DCE (2 mL) was stirred at rt overnight then filtered. The filtrate was concentrated and purified by prep. HPLC to give the title compound as TFA salt as a yellow solid (50 mg, 76%). $^1H$ NMR (400 MHz, $CD_3OD$) δ 7.66 (d, J=9.03 Hz, 1H), 7.51 (d, J=5.77 Hz, 1H), 7.29 (t, J=8.91 Hz, 2H), 7.18 (d, J=6.02 Hz, 1H), 4.98-4.87 (m, 4H), 4.54-4.45 (m, 1H), 3.63-3.40 (m, 8H); MS ESI $[M+H]^+$ 423.2, calcd for $[C_{21}H_{22}N_6O_2S+H]^+$ 423.2.

| Example/IUPAC name | Structure | Yield; description; salt |
|---|---|---|
| A66: 4-(((1S,2S)-2-hydroxycyclopentyl)amino)-5-(6-(4-methylpiperazin-1-yl)-1H-benzo[d]imidazol-2-yl)thieno[2,3-b]pyridin-6(7H)-one | 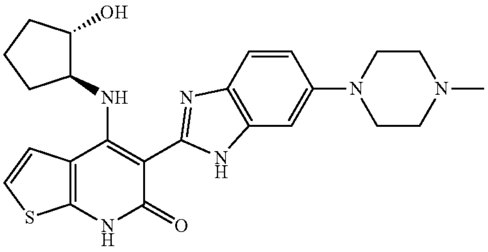 [SMILES: CN1CCN(c2ccc3nc(-c4c(N[C@H]5CCC[C@@H]5O)c5ccsc5[nH]c4=O)[nH]c3c2)CC1] | 35 mg (23%); brown solid; 2 HCl |

Step 1: Reagents (general method C): a mixture of 7-(4-methoxybenzyl)-5-(5 and 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.22 g, 0.29 mmol), (1S,2S)-2-

-continued

| Example/IUPAC name | Structure | Yield; description; salt |
|---|---|---|

aminocyclopentan-1-ol (0.12 g, 1.2 mmol), DMF (5 mL). MS ESI [M − $CF_3O_2S$ + 2H]$^+$ 585.4, calcd for [$C_{32}H_{36}N_6O_3S$ + H]$^+$ 585.3.
Step 2: Reagents (general method D): a mixture of 2-(4-(((1S,2S)-2-hydroxycyclopentyl)amino)-7-(4-methoxybenzyl)-6-oxo-6,7-dihydrothieno[2,3-b]pyridin-5-yl)-5- and 6-(4-methylpiperazin-1-yl)-1H-benzo[d]imidazol-1-yl trifluoromethanesulfonate (crude, 0.28 mmol), TFA (5 mL), and conc. HCl (1 mL). 1H NMR (400 MHz, $CD_3OD$) δ = 7.75-7.60 (m, 2 H), 7.41 (br. s, 1 H), 7.30 (s, 1 H), 7.19 (d, J = 5.0 Hz, 1 H), 4.15-4.04 (m, 1 H), 4.02-3.89 (m, 2 H), 3.73-3.61 (m, 2 H), 3.28-3.14 (m, 5 H), 3.00 (br. s., 3 H), 1.99-1.84 (m, 2 H), 1.76-1.46 (m, 3 H), 1.43-1.31 (m, 1 H); MS ESI [M + H]$^+$ 465.3, calcd for [$C_{24}H_{28}N_6O_2S$ + H]$^+$ 465.2.

| Example/IUPAC name | Structure | Yield; description; salt |
|---|---|---|
| A67: 4-(((1R,2R)-2-hydroxycyclopentyl)amino)-5-(6-(4-methylpiperazin-1-yl)-1H-benzo[d]imidazol-2-yl)thieno[2,3-b]pyridin-6(7H)-one | 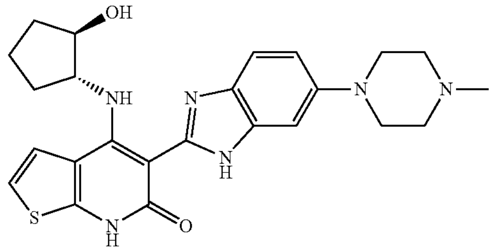 [SMILES: CN1CCN(c2ccc3nc(-c4c(N[C@@H]5CCC[C@H]5O)c5ccsc5[nH]c4=O)[nH]c3c2)CC1] | 45 mg (29%); borwn solid; 2 HCl |

Step 1: Reagents (general method C): a mixture of 7-(4-methoxybenzyl)-5-(5 and 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.22 g, 0.29 mmol), (1R,2R)-2-aminocyclopentan-1-ol (0.12 g, 1.2 mmol), DMF (5 mL). MS ESI [M − $CF_3O_2S$ + 2H]$^+$ 585.4, calcd for [$C_{32}H_{36}N_6O_3S$ + H]$^+$ 585.3.
Step 2: Reagents (general method D): a mixture of 2-(4-(((1R,2R)-2-hydroxycyclopentyl)amino)-7-(4-methoxybenzyl)-6-oxo-6,7-dihydrothieno[2,3-b]pyridin-5-yl)-5- and 6-(4-methylpiperazin-1-yl)-1H-benzo[d]imidazol-1-yl trifluoromethanesulfonate (crude, 0.28 mmol), TFA (5 mL), and conc. HCl (1 mL). 1H NMR (400 MHz, $CD_3OD$) δ = 7.76-7.62 (m, 2 H), 7.45-7.36 (m, 1 H), 7.35-7.26 (m, 1 H), 7.22-7.15 (m, 1 H), 4.14-4.05 (m, 1 H), 4.02-3.89 (m, 2 H), 3.74-3.62 (m, 2 H), 3.27-3.17 (m, 5 H), 3.00 (br. s., 3 H), 2.00-1.83 (m, 2 H), 1.74-1.47 (m, 3 H), 1.45-1.32 (m, 1 H); MS ESI [M + H]$^+$ 465.3, calcd for [$C_{24}H_{28}N_6O_2S$ + H]$^+$ 465.2.

| Example/IUPAC name | Structure | Yield; description; salt |
|---|---|---|
| A68: 7-amino-6-(5-fluoro-6-(4-methylpiperazin-1-yl)-1H-benzo[d]imidazol-2-yl)thieno[3,2-b]pyridin-5(4H)-one | 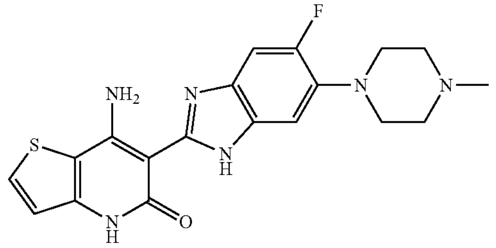 [SMILES: CN1CCN(c2cc3[nH]c(-c4c(N)c5sccc5[nH]c4=O)nc3cc2F)CC1] | 91 mg (32%); brown solid; 2 HCl |

Reagents (general method A1): 3-amino-2-cyanothiophene (75 mg, 0.6 mmol), ethyl 2-(6-(4-methylpiperazin-1-yl)-1H-benzo[d]imidazol-2-yl)acetate (193 mg, 0.6 mmol), LDA (3 ml, 3 mmol), THF (8 mL). $^1H$ NMR (400 MHz, $CD_3OD$) δ 8.01 (d, J = 5.5 Hz, 1H), 7.59 (d, J = 11.0 Hz, 1H), 7.49 (d, J = 7.3 Hz, 1H), 7.11 (d, J = 5.3 Hz, 1H), 3.71-3.68 (m, 4H), 3.46-3.41 (m, 2H), 3.23-3.31 (m, 2H), 3.03 (s, 3H); MS ESI [M + H]$^+$ 399.2, calcd for [$C_{19}H_{19}FN_6OS$ + H]$^+$ 399.4.

| Example/IUPAC name | Structure | Yield; description; salt |
|---|---|---|
| A69: 4-amino-5-(7-fluoro-6-(4-methylpiperazin-1-yl)-1H-benzo[d]imidazol-2-yl)thieno[2,3-b]pyridin-6(7H)-one | 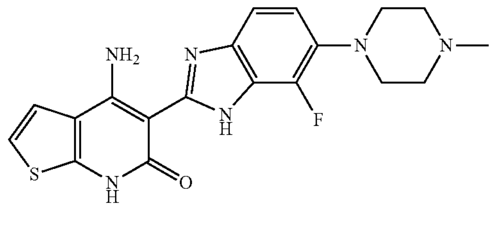 [SMILES: CN1CCN(c2ccc3nc(-c4c(N)c5ccsc5[nH]c4=O)[nH]c3c2F)CC1] | 49 mg (13%); brown solid; 2 HCl |

Reagents (general method A1): 2-amino-3-cyanothiophene (100 mg, 0.8 mmol), ethyl 2-(6-(4-methylpiperazin-1-yl)-1H-benzo[d]imidazol-2-yl)acetate (258 mg, 0.8 mmol), LDA (4 ml, 4 mmol), THF (10 mL). $^1H$ NMR (400 MHz, $CD_3OD$) δ 7.57-7.51 (m, 2H), 7.39-7.35 (m, 1H), 7.20 (d, J = 5.8 Hz, 1H), 3.69-3.36 (m, 4H), 3.47-3.37 (m, 4H), 3.35 (s, 2H), 3.03 (s, 3H); MS ESI [M + H]$^+$ 399.2, calcd for [$C_{19}H_{19}FN_6OS$ + H]$^+$ 399.4.

-continued

| Example/IUPAC name | Structure | Yield; description; salt |
|---|---|---|
| A70: 4-(((1S,2R)-2-hydroxycyclohexyl)amino)-3-(6-(4-methylpiperazin-1-yl)-1H-benzo[d]imidazol-2-yl)thieno[3,4-b]pyridin-2(1H)-one | 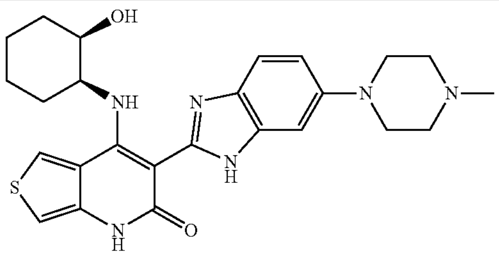 [SMILES: CN1CCN(c2ccc3nc(-c4c(N[C@H]5CCCC[C@H]5O)c5cscc5[nH]c4=O)[nH]c3c2)CC1] | 40 mg (22%); yellow solid; 2 HCl |

Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.26 g, 0.34 mmol), (1R,2S)-2-aminocyclohexan-1-ol (0.1 g, 0.85 mmol), DMF (5 mL). MS ESI $[M + H]^+$ 731.3, calcd for $[C_{34}H_{37}F_3N_6O_5S_2 + H]^+$ 731.2.

Step 2: Reagents (general method D): a mixture of 4-(((1S,2R)-2-hydroxycyclohexyl)amino)-1-(4-methoxybenzyl)-3-(5- and (6-(4-methylpiperazin-1-yl)-1-((trifluoromethyl)sulfonyl)-1H-benzo[d]imidazol-2-yl)thieno[3,4-b]pyridin-2(1H)-one (220 mg crude), TFA (5 mL), and conc. HCl (2 mL). $^1$H NMR (400 MHz, $CD_3OD$) δ 8.43 (d, J = 3.3 Hz, 1H), 7.73 (d, J = 9.0 Hz, 1H), 7.44 (dd, J = 9.0, 2.2 Hz, 1H), 7.34 (d, J = 2.3 Hz, 1H), 7.01 (d, J = 3.0 Hz, 1H), 4.03-3.94 (m, 3H), 3.74-3.65 (m, 2H), 3.42-3.35 (m, 3H), 3.31-3.19 (m, 3H), 3.03 (s, 3H), 1.87-57 (m, 5H), 1.35-1.17 (m, 2H); MS ESI $[M + H]^+$ 479.4, calcd for $[C_{25}H_{30}N_6O_2S + H]^+$ 479.2.

| Example/IUPAC name | Structure | Yield; description; salt |
|---|---|---|
| A71: (R)-3-(6-(4-methylpiperazin-1-yl)-1H-benzo[d]imidazol-2-yl)-4-((tetrahydrofuran-3-yl)amino)thieno[3,4-b]pyridin-2(1H)-one | 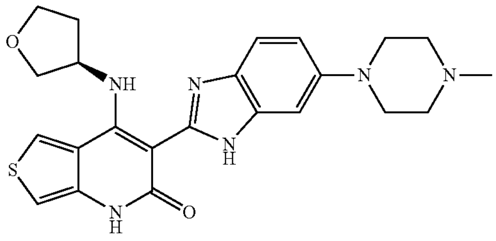 [SMILES: CN1CCN(c2ccc3nc(-c4c(N[C@@H]5CCOC5)c5cscc5[nH]c4=O)[nH]c3c2)CC1] | 6 mg (3%); yellow solid; 2 HCl |

Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.19 g, 0.26 mmol), (R)-3-aminotetrahydrofuran (0.06 g, 0.64 mmol), DMF (5 mL). MS ESI $[M + H]^+$ 703.3, calcd for $[C_{32}H_{33}F_3N_6O_5S_2 + H]^+$ 703.2.

Step 2: Reagents (general method D): a mixture of (R)-3-(5- and (6-(4-methylpiperazin-1-yl)-1-((trifluoromethyl)sulfonyl)-1H-benzo[d]imidazol-2-yl)-4-((tetrahydrofuran-3-yl)amino)thieno[3,4-b]pyridin-2(1H)-one (crude, 165 mg), TFA (4 mL), and conc. HCl (1.5 mL). $^1$H NMR (400 MHz, $CD_3OD$) δ 8.54 (d, J = 3.3 Hz, 1H), 7.74 (d, J = 9.5 Hz, 1H), 7.45 (dd, J = 9.0, 2.3 Hz, 1H), 7.34 (d, J = 2.01 Hz, 1H), 7.00 (d, J = 3.3 Hz, 1H), 4.02-3.91 (m, 3H), 3.85 (dd, J = 9.5, 3.3 Hz, 1H), 3.78-3.54 (m, 5H), 3.43-3.35 (m, 2H), 3.28-3.19 (m, 2H), 3.03 (s, 3H), 2.11-1.94 (m, 2H); MS ESI $[M + H]^+$ 451.3, calcd for $[C_{23}H_{26}N_6O_2S + H]^+$ 451.2.

| Example/IUPAC name | Structure | Yield; description; salt |
|---|---|---|
| A72: 4-(((1S,2R)-2-hydroxycyclohexyl)amino)-5-(6-morpholino-1H-benzo[d]imidazol-2-yl)thieno[2,3-b]pyridin-6(7H)-one | 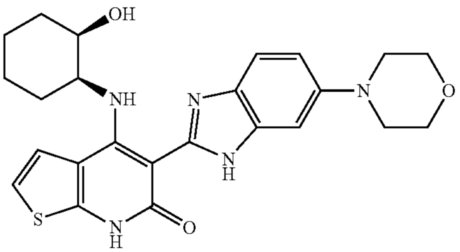 [SMILES: O=c1[nH]c2sccc2c(N[C@H]2CCCC[C@H]2O)c1-c1nc2ccc(N3CCOCC3)cc2[nH]1] | 19 mg (7%); brown solid; 2 HCl |

Step 1: reagents (general method C): 4-(4-methoxybenzyl)-6-(5- and 6-morpholino-1-((trifluoro-methyl)sulfonyl)-1H-benzo[d]imidazol-2-yl)-5-oxo-4,5-dihydrothieno[3,2-b]pyridin-7-yl trifluoro-methanesulfonate (crude, 0.51 mmol), (1R,2S)-2-aminocyclohexanol (0.23 g, 2.1 mmol), DMF (6 mL). MS ESI $[M - CF_3O_2S + 2H]^+$ 586.5, calcd for $[C_{32}H_{35}N_5O_4S + H]^+$ 586.2.

Step 2: Reagents (general method D): a mixture of 2-(4-(((1S,2R)-2-hydroxycyclohexyl)amino)-7-(4-methoxybenzyl)-6-oxo-6,7-dihydrothieno[2,3-b]pyridin-5-yl)-5- and 6-morpholino-1H-benzo[d]imidazol-1-yl trifluoromethanesulfonate (0.38, 0.51 mmol), TFA (5 mL), and conc. HCl (1 mL). 1H NMR (400 MHz, $CD_3OD$) δ = 7.77-7.69 (m, 1 H), 7.64-7.57 (m, 1 H), 7.54-7.45 (m, 2 H), 7.24-7.15 (m, 1 H), 4.09-3.96 (m, 5 H), 3.60-3.44 (m, 5 H), 1.98-1.52 (m, 6 H), 1.48-1.22 (m, 2 H); MS ESI $[M + H]^+$ 466.4, calcd for $[C_{24}H_{27}N_5O_3S + H]^+$ 466.2.

-continued

| Example/IUPAC name | Structure | Yield; description; salt |
|---|---|---|
| A73: 5-(6-((2S,6R)-2,6-dimethylmorpholino)-1H-benzo[d]imidazol-2-yl)-4-(((1S,2R)-2-hydroxycyclohexyl)amino)thieno[2,3-b]pyridin-6(7H)-one | 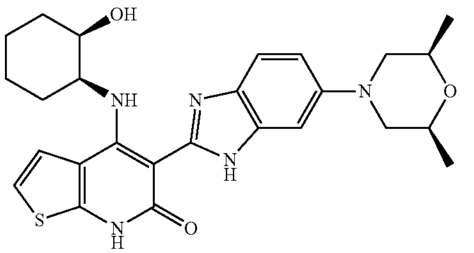 [SMILES: C[C@@H]1CN(c2ccc3nc(-c4c(N[C@H]5CCCC[C@H]5O)c5ccsc5[nH]c4=O)[nH]c3c2)C[C@H](C)O1] | 8 mg (6%); brown solid; TFA |

Step 1: Reagents (general method C): 5-(5 and (6-((2S,6R)-2,6-dimethylmorpholino)-1-(((trifluoromethyl)sulfonyl)oxy)-1H-benzo[d]imidazol-2-yl)-7-(4-methoxybenzyl)-6-oxo-6,7-dihydrothieno[2,3-b]pyridin-4-yl trifluoromethanesulfonate (crude, 0.23 mmol), (1R,2S)-2-aminocyclohexanol (0.26 g, 0.23 mmol), DMF (1 mL). MS ESI $[M + H]^+$ 746.5, calcd for $[C_{35}H_{38}F_3N_5O_6S_2 + H]^+$ 746.2.

Step 2: Reagents (general method D): a mixture of 5-(6-((2S,6R)-2,6-dimethylmorpholino)-1-((trifluoromethyl)sulfonyl)-1H-benzo[d]imidazol-2-yl)-4-(((1S,2R)-2-hydroxycyclohexyl)amino)-7-(4-methoxybenzyl)thieno[2,3-b]pyridin-6(7H)-one and 5-((1S,6R)-2,6-dimethylmorpholino)-2-(4-(((1S,2R)-2-hydroxycyclohexyl)amino)-7-(4-methoxybenzyl)-6-oxo-6,7-dihydrothieno[2,3-b]pyridin-5-yl)-1H-benzo[d]imidazol-1-yl trifluoromethanesulfonate (0.094 g, 0.13 mmol), TFA (3 mL), and conc. HCl (1 mL). 1H NMR (400 MHz, $CD_3OD$) δ 7.69 (d, J = 9.0 Hz, 1 H), 7.56-7.48 (m, 2 H), 7.40 (d, J = 10.0 Hz, 1 H), 7.20 (d, J = 6.0 Hz, 1 H), 4.10-4.04 (m, 1 H), 4.04-3.89 (m, 3 H), 3.67 (d, J = 11.3 Hz, 2 H), 2.98-2.86 (m, 2 H), 2.02-1.89 (m, 2 H), 1.86-1.68 (m, 3 H), 1.68-1.58 (m, 1 H), 1.52-1.40 (m, 1 H), 1.39-1.33 (m, 1 H), 1.31 (d, J = 6.3 Hz, 6 H); MS ESI $[M + H]^+$ 494.5, calcd for $[C_{26}H_{31}N_5O_3S + H]^+$ 494.2.

| Example/IUPAC name | Structure | Yield; description; salt |
|---|---|---|
| A74: 4-((2-methoxyethyl)amino)-5-(6-(4-methylpiperazin-1-yl)-1H-benzo[d]imidazol-2-yl)thieno[2,3-b]pyridin-6(7H)-one | 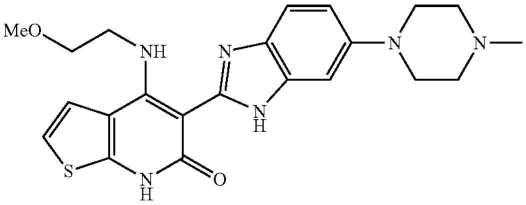 [SMILES: COCCNc1c(-c2nc3ccc(N4CCN(C)CC4)cc3[nH]2)c(=O)[nH]c2sccc12] | 55 mg (33%); dark yellow solid; TFA |

Step 1: Reagents (general method C): a mixture of 7-(4-methoxybenzyl)-5-(5 and 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (crude, 0.30 mmol), 2-methoxyethanamine (0.10 mL, 1.2 mmol), DMF (4 mL). MS ESI $[M + H]^+$ 691.4, calcd for $[C_{31}H_{33}F_3N_6O_5S_2 + H]^+$ 691.2.

Step 2: Reagents (general method D): a mixture of 2-(7-(4-methoxybenzyl)-4-((2-methoxyethyl)amino)-6-oxo-6,7-dihydrothieno[2,3-b]pyridin-5-yl)-5- and 6-(4-methylpiperazin-1-yl)-1H-benzo[d]imidazol-1-yl trifluoromethanesulfonate (crude, 0.30 mmol), TFA (5 mL), and conc. HCl (0.5 mL). 1H NMR (400 MHz, $CD_3OD$) δ 7.68 (d, J = 8.8 Hz, 1 H), 7.62-7.56 (m, 1 H), 7.34 (d, J = 9.0 Hz, 1 H), 7.29 (d, J = 1.8 Hz, 1 H), 7.20 (d, J = 6.0 Hz, 1 H), 3.99-3.86 (m, 2 H), 3.76-3.64 (m, 2 H), 3.58 (d, J = 5.3 Hz, 2 H), 3.42-3.34 (m, 7 H), 3.25-3.12 (m, 2 H), 3.02 (s, 3 H); MS ESI $[M + H]^+$ 439.5, calcd for $[C_{22}H_{26}N_6O_2S + H]^+$ 439.2.

| Example/IUPAC name | Structure | Yield; description; salt |
|---|---|---|
| A75: 4-(((1R,2R)-2-hydroxycyclopentyl)amino)-3-(6-(4-methylpiperazin-1-yl)-1H-benzo[d]imidazol-2-yl)thieno[3,4-b]pyridin-2(1H)-one | 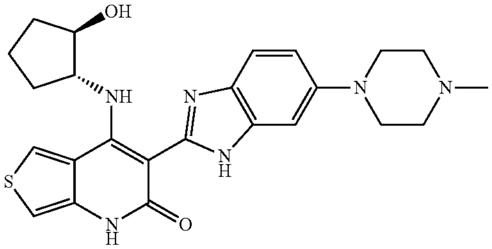 [SMILES: CN1CCN(c2ccc3nc(-c4c(N[C@@H]5CCC[C@H]5O)c5cscc5[nH]c4=O)[nH]c3c2)CC1] | 22 mg (16%); yellow solid; 2 HCl |

Step 1: Reagents (general method C): a mixture of 7-(4-methoxybenzyl)-5-(5 and/or 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (0.19 g, 0.26 mmol), (1R,2R)-2-aminocyclopentanol (0.06 g, 0.64 mmol), DMF (5 mL). MS ESI $[M + H]^+$ 717.2, calcd for $[C_{33}H_{35}F_3N_6O_5S_2 + H]^+$ 717.2.

Step 2: Reagents (general method D): a mixture of 4-(((1R,2R)-2-hydroxycyclopentyl)amino)-1-(4-methoxybenzyl)-3-(5- and (6-(4-methylpiperazin-1-yl)-1-((trifluoromethyl)sulfonyl)-1H-benzo[d]imidazol-2-yl)thieno[3,4-b]pyridin-2(1H)-one (crude, 165 mg), TFA (4 mL), and conc. HCl (1 mL). $^1H$ NMR (400 MHz, $CD_3OD$) δ 8.59 (d, J = 3.3 Hz, 1H), 7.72 (d, J = 9.0 Hz, 1H), 7.44 (dd, J = 9.0, 2.3 Hz, 1H), 7.33 (d, J = 2.0 Hz, 1H), 7.00 (d, J = 3.3 Hz, 1H), 4.19-4.12

-continued

| Example/IUPAC name | Structure | Yield; description; salt |
|---|---|---|
| (m, 1H), 4.00-3.97 (m, 2H), 3.74-3.65 (m, 2H), 3.43-3.35 (m, 2H), 3.30-3.21 (m, 2H), 3.19-3.10 (m, 1H), 3.03 (s, 3H), 1.99-1.87 (m, 2H), 1.76-1.65 (m, 2H), 1.57-1.44 (m, 1H), 1.44-1.28 (m, 1H); MS ESI [M + H]$^+$ 465.4, calcd for [$C_{24}H_{28}N_6O_2S$ + H]$^+$ 465.2. | | |
| A76: 4-amino-5-(6-((2S,6R)-2,6-dimethylmorpholino)-1H-benzo[d]imidazol-2-yl)thieno[2,3-b]pyridin-6(7H)-one | 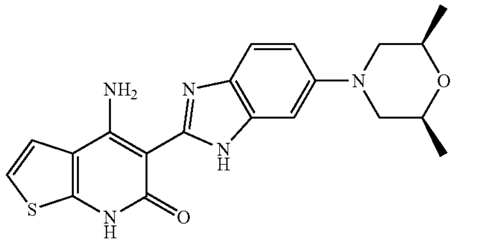 [SMILES: C[C@@H]1CN(c2ccc3nc(-c4c(N)c5ccsc5[nH]c4=O)[nH]c3c2)C[C@H](C)O1] | 49 mg (31%); greenish-yellow solid; TFA |
| Reagents (general method A2): ethyl 2-(6-((2S,6R)-2,6-dimethylmorpholino)-1H-benzo[d]imidazol-2-yl)acetate (0.10 g, 0.32 mmol), 2-aminothiophene-3-carbonitrile (0.32 g, 0.32 mmol), LDA (1.0 M in THF/hex, 1.1 mL, 1.1 mmol), THF (1 mL), 45° C., 1.5 h. 50 mg of mixture of uncyclized and cyclized was obtained which was recyclized with KOBu$^t$ (1.0 M in THF, 1.3 mL, 1.3 mmol), in THF (10 mL), 45° C., 2 h; $^1$H NMR (400 MHz, $CD_3OD$) δ 7.69 (d, J = 9.5 Hz, 1 H), 7.52 (d, J = 6.0 Hz, 1 H), 7.49-7.45 (m, 1 H), 7.37 (d, J = 9.0 Hz, 1 H), 7.19 (d, J = 5.8 Hz, 1 H), 4.03-3.92 (m, 2 H), 3.71-3.61 (m, 2 H), 2.92-2.77 (m, 2 H), 1.31 (d, J = 6.3 Hz, 6 H); MS ESI [M + H]$^+$ 396.3, calcd for [$C_{20}H_{21}N_5O_2S$ + H]$^+$ 396.1. | | |
| A77: (R)-5-(6-(4-methylpiperazin-1-yl)-1H-benzo[d]imidazol-2-yl)-4-((tetrahydro-2H-pyran-3-yl)amino)thieno[2,3-b]pyridin-6(7H)-one | 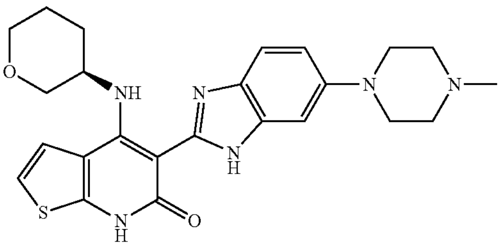 [SMILES: CN1CCN(c2ccc3nc(-c4c(N[C@@H]5CCCOC5)c5ccsc5[nH]c4=O)[nH]c3c2)CC1] | 66 mg (38%); yellow solid; TFA |
| Step 1: Reagents (general method C): a mixture of 7-(4-methoxybenzyl)-5-(5 and 6-(4-methyl-piperazin-1-yl)-1-((trifluoromethyl)sulfonyl)-1H-benzo[d]imidazol-2-yl)-6-oxo-6,7-dihydrothieno[2,3-b]pyridin-4-yl trifluoromethanesulfonate (crude, 0.30 mmol), (R)-tetrahydro-2H-pyran-3-amine (crude in DCM, 1.5 mmol), DMF (5 mL). MS ESI [M + H]$^+$ 717.4, calcd for [$C_{33}H_{35}F_3N_6O_5S_2$ + H]$^+$ 717.2. Step 2: Reagents (general method D): a mixture of (R)-2-(7-(4-methoxybenzyl)-6-oxo-4-((tetrahydro-2H-pyran-3-yl)amino)-6,7-dihydrothieno[2,3-b]pyridin-5-yl)-5- and 6-(4-methylpiperazin-1-yl)-1H-benzo[d]imidazol-1-yl trifluoromethanesulfonate (crude, 0.30 mmol), TFA, and conc. HCl. 1H NMR (400 MHz, $CD_3OD$) δ 7.67 (d, J = 8.8 Hz, 1 H), 7.56 (d, J = 5.8 Hz, 1 H), 7.37-7.26 (m, 2 H), 7.21 (d, J = 6.0 Hz, 1 H), 4.00-3.80 (m, 3 H), 3.75-3.59 (m, 3 H), 3.53-3.41 (m, 2 H), 3.40-3.34 (m, 2 H), 3.29-3.11 (m, 3 H), 3.01 (s, 3 H), 2.14-1.96 (m, 1 H), 1.83-1.66 (m, 2 H), 1.42-1.25 (m, 1 H); MS ESI [M + H]$^+$ 465.3, calcd for [$C_{24}H_{28}N_6O_2S$ + H]$^+$ 465.2. | | |

Example B

HPK1 Inhibition Assay

Active HPK1 (MAP4K1) was purchased as an N-terminal GST fusion of human HPK1 (aa 1-346) from Invitrogen (cat #PV6355). HPK1 activity was measured using an indirect ELISA detection system. GST-HPK1 (0.6 nM) was incubated in the presence of 12 μM ATP (Sigma cat #A7699), 5 mM MOPS (pH 7.2), 2.5 mM β-glycerol-phosphate, 5 mM $MgCl_2$, 0.4 mM EDTA, 1 mM EGTA, 0.05 mM DTT, in a 96 well microtitre plate pre-coated with 0.5 μg/well bovine myelin basic protein (MBP) (Millipore, cat #13-110). The reaction was allowed to proceed for 30 min, followed by 5 washes of the plate with Wash Buffer (phosphate buffered saline supplemented with 0.2% Tween 20), and incubation for 30 min with a 1:3000 dilution of anti-phospho-threonine rabbit polyclonal antibody (Cell Signaling cat #9381). The plate was washed 5 times with wash buffer, incubated for 30 min in the presence of goat anti-rabbit horse radish peroxidase conjugate (BioRad cat #1721019, 1:3000 concentration), washed an additional 5 times with wash buffer, and incubated in the presence of TMB substrate (Sigma cat #T0440). The colorimetric reaction was allowed to continue for 5 min, followed by addition of stop solution (0.5 N $H_2SO_4$), and quantified by detection at 450 nm with a monochromatic plate reader (Molecular Devices M5).

Compound inhibition was determined at either a fixed concentration (10 μM) or at a variable inhibitor concentration (typically 50 μM to 0.1 μM in a 10 point dose response titration). Compounds were pre-incubated in the presence of enzyme for 15 min prior to addition of ATP and the activity remaining quantified using the above described activity assay. The % inhibition of a compound was determined using the following formula; % inhibition=100×(1−(experimental value−background value)/(high activity control−background value)). The $IC_{50}$ value was determined using a non-linear 4 point logistic curve fit (XLfit4, IDBS) with the formula; (A+(B/(1+((x/C)^D)))), where A=background value, B=range, C=inflection point, D=curve fit parameter.

Example C

FLT3 Inhibition Assay

FLT3 and LCK compound inhibition were determined using FRET based Z'-LYTE Kinase Assay Kit with Tyrosine 2 peptide as the substrate (Invitrogen cat #PV3191). The FLT3 kinase assay was performed according to the manufacturer's suggested specifications with an ATP concentration of 940 μM and 1 nM FLT3 (Invitrogen cat #PV3182) and 180 μM ATP and 25 nM LCK (Invitrogen cat #P3043) for the LCK kinase reaction. The % inhibition values were determined according to the manufacturer's directions and $IC_{50}$ values were obtained using a non-linear 4 point logistic curve fit (XLfit4, IDBS).

In Table 1 below, $IC_{50}$ value ranges for exemplary compounds are given. The $IC_{50}$ ranges are indicated as "A," "B," and "C," for values less than or equal to 0.05 μM; those greater than 0.05 μM and less than or equal to 0.5 μM; and those greater than 0.5 μM, respectively.

TABLE 1

Inhibition Data of HPK1, Lck and Flt3

| | $IC_{50}$ Range | | |
|---|---|---|---|
| Example | HPK1 | Lck | Flt3 |
| A1 | A | B | A |
| A2 | A | B | A |
| A3 | C | — | — |
| A4 | A | B | A |
| A5 | C | C | — |
| A6 | B | — | — |
| A7 | A | B | A |
| A8 | A | B | A |
| A9 | A | A | A |
| A10 | A | B | A |
| A11 | A | | |
| A12 | A | — | — |
| A13 | A | B | A |
| A14 | A | A | A |
| A15 | A | A | A |
| A16 | A | — | — |
| A17 | A | A | A |
| A18 | A | B | A |
| A19 | B | | |
| A20 | C | | |
| A21 | A | C | B |
| A22 | A | B | A |
| A23 | A | A | A |
| A24 | A | A | A |
| A25 | A | — | — |
| A26 | A | — | — |
| A27 | A | A | A |
| A28 | A | — | — |
| A29 | A | B | — |
| A30 | A | A | A |
| A31 | A | B | A |
| A32 | C | A | — |
| A33 | A | B | A |
| A34 | A | A | A |
| A35 | A | A | A |
| A36 | A | A | A |
| A37 | A | A | A |
| A38 | A | A | A |
| A39 | A | A | A |
| A40 | A | A | A |
| A41 | A | A | A |
| A42 | A | A | A |
| A43 | A | B | A |
| A44 | A | A | A |
| A45 | A | A | A |
| A46 | A | B | A |
| A47 | A | — | — |
| A48 | A | A | A |
| A49 | C | — | — |
| A50 | C | C | — |
| A51 | A | — | — |
| A52 | A | A | A |
| A53 | A | A | A |
| A54 | A | B | A |
| A55 | A | B | A |
| A56 | A | — | — |
| A57 | A | B | A |
| A58 | A | B | A |
| A59 | — | — | — |
| A60 | B | B | — |
| A61 | A | B | A |
| A62 | B | — | — |
| A63 | A | — | — |
| A64 | A | B | A |
| A65 | A | B | A |
| A66 | A | A | A |
| A67 | A | B | A |
| A68 | A | A | A |
| A69 | — | B | A |
| A70 | — | A | A |
| A71 | A | A | A |
| A72 | A | C | A |
| A73 | B | — | — |
| A74 | A | — | — |
| A75 | A | — | — |
| A76 | A | — | — |
| A77 | A | — | — |

Example D

In vitro Phosphorylation Assays

Jurkat E6.1 cells were obtained from American Type Culture Collection (ATCC, Manassas, Va.), and maintained according to the supplier's instructions. Cells were washed three times and starved in RPMI 1640 medium supplemented with 0.5% fetal calf serum for 18 h at 37° C. Serum starved cells were pretreated with the indicated concentration of inhibitor for 4 hours before stimulation with 10 μg/ml α-CD3 antibody (BioLegend, Inc., San Diego, Calif.) for 10 min at 37° C. The cells were washed once in phosphate-buffered saline (pH 7.4) containing 10 mm sodium pyrophosphate, 10 mm sodium fluoride, 10 mm EDTA, and 1 mm sodium orthovanadate. Protein lysates were prepared using ice-cold radioimmunoprecipitation assay (RIPA) lysis buffer. A total of 100 μg of cell lysate was loaded onto Bis-Tris gels (Life Technologies, Carlsbad, Calif.) with full-range molecular weight marker as a size reference, and resolved by SDS-PAGE electrophoresis. Proteins were transferred to PVDF membrane (Millipore, Billerica, Mass.), blocked and probed with antibodies for phospho-SLP-76 (Ser376) (rabbit polyclonal #13177; Cell Signaling Technology Inc., Danvers, Mass.), SLP-76 (rabbit polyclonal #4958; Cell Signaling Technology Inc., Danvers, Mass.), phospho-ERK (mouse monoclonal sc-7383; Santa Cruz Biotechnology Inc., Santa Cruz, Calif.) and ERK1/2 (rabbit polyclonal 06-182; Millipore, Billerica, Mass.). Secondary antibodies were diluted 1 in 15,000 and incubated for 1 h at rt. Protein bands were visualized and quantified using Odyssey near infrared imager (LI-COR, Lincoln, Nebr.).

Table 2 below lists effects of representative compounds of the present invention against SLP-76 serine 376 phosphorylation and ERK1/2 T202/Y204 phosphorylation in α-CD3 stimulated Jurkat E6.1 cells.

TABLE 2

Effects of HPK1 inhibitors against SLP-76 serine 376 phosphorylation and ERK1/2 T202/Y204 phosphorylation in α-CD3 stimulated Jurkat E6.1 cells.

| Compound Example | SLP76 S376 Phosphorylation Onset-Substantive* Inhibition (μM) | ERK1/2 T202/Y204 Phosphorylation Onset Inhibition (μM) |
|---|---|---|
| A1 | 0.3-1.0 | >3.0 |
| A30 | 0.3-1.0 | >3.0 |
| A43 | 0.1-0.3 | >3.0 |
| A18 | 0.3-1.0 | >3.0 |
| A10 | 1.0-3.0 | >3.0 |
| A57 | 0.3-1.0 | >3.0 |
| A23 | 0.3-1.0 | >3.0 |
| A58 | 0.1-0.3 | >3.0 |
| A34 | 1.0-3.0 | 3.0 |
| A21 | >3.0 | >3.0 |
| A37 | 0.1-0.3 | 1.0-3.0 |

*>75% inhibition as estimated by immunoblot analysis

Example E

Syngeneic CT26 Cell Line Xenograft Model

The CT26 WT cell line, which is an N-nitroso-N-methylurethane-(NNMU) induced, mouse-derived, undifferentiated colon carcinoma cell line, was obtained from American Type Culture Collection (ATCC CRL-2638, Manassas, Va., D.C., USA). Cells were grown in Roswell Park memorial Institute medium commonly referred to as RPMI 1640 Medium containing 4.5 g/L glucose, 0.11 g/L sodium pyruvate, 1.5 g/L sodium bicarbonate, L-glutamine & 2.385 g/L HEPES plus 10% fetal bovine serum. Six to eight week old female BALB/c mice were purchased from Jackson Laboratories and received and acclimated at the MaRS-TMDT Animal Resources Centre for 1 week prior to the start of the experiment. The mice were fed ad libitum autoclaved water and Rodent Lab Diet (Harlan Teklad LM-485) consisting of 19% crude protein, 5% crude fat, and 5% crude fiber. Mice were housed in microisolator cages and maintained in an environment with a 12 h light cycle at 20-22° C. and 40-60% humidity. On the day of implantation, CT26 cells were harvested and re-suspended with serum free RPMI1640 to a concentration of $1\times10^7$/mL and each mouse was injected subcutaneously with a volume of 0.1 mL containing $1\times10^6$ CT26 cells in the right rear flank. After 6 d, palpable tumors with an average volume of ~65 $mm^3$ (calculated using the formula: tumor volume=width$^2$×length/2) had formed. At this time, animals were separated into five groups of eight animals per group such that each group contained animals bearing tumors of similar average size and treatment was initiated. For dosing, Example A1 was dissolved in water to a concentration of 7.5 mg/mL or 15 mg/mL for dosing of the 75 mg/kg and the 150 mg/kg doses, respectively. As a positive control and to investigate the combinatorial activity of Example A1, a rat IgG2b anti-PD1 antibody (BioXcell (N.H., USA)) was dosed used. The five groups were treated with: i) 10 mL/kg water QD for 21 d administered by oral gavage (PO) plus 150 μg rat IgG2b isotype control antibody dosed by intraperitoneal (IP) injection on day 0, 3, 6 and 10 (the control arm); ii) 150 μg anti-PD-1 antibody dosed by intraperitoneal (IP) injection on day 0, 3, 6 and 10; iii) 75 mg/kg Example A1 QD for 21 days administered PO; iv) 150 mg/kg Example A1 QD for 21 days administered PO v) 150 mg/kg Example A1 QD for 21 days administered PO plus 150 μg anti-PD-1 antibody dosed by intraperitoneal (IP) injection on day 0, 3, 6 and 10. Toxicity was evaluated by body weight measurements and clinical observations. Tumour measurements and body weights were taken three times per week. Percent tumor growth inhibition (TGI) was calculated by the formula:

$$\%\ TGI=100\times[1-(TV_{f,treated}-TV_{i,treated})/(TV_{f,control}-TV_{i,control})]$$

Figure 2:
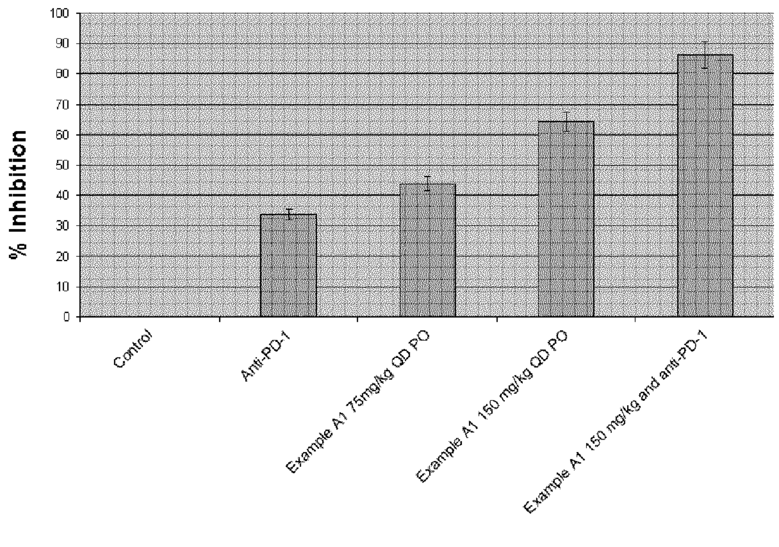
FIG. 2 is a graph illustrating the tumour growth inhibition percentage following administration of compound A1 alone and in combination with an anti-PD1 antibody.

Tumour growth inhibition at day 21, is shown in FIG. 2. A dose-dependent effect was observed in response to treatment with Example A1, with 75 mg/kg and 150 mg/kg QD inhibiting tumour growth by 44% and 64%, respectively. Whilst the anti-PD-1 antibody alone resulted in an average TGI of 34%, when combined with 150 mg/kg QD Example A1, the TGI increased to 86%.

According to University Health Network (UHN) Animal Use Protocols (AUPs), mice in efficacy experiments should be sacrificed when the tumour size is above 1500 $mm^3$ or if the body weight of the animal decreases or if the animals are displaying clinical signs that require termination for humane reasons. In this study, the compound was well tolerated with all animals gaining weight over the course of the study and no animals were terminated due to clinical signs. A tumour size of <1500 $mm^3$ at day 21 was used as a cutoff to represent survival. Using this cutoff, at day 21 no animals survived in the control arm, 1 of 8 animals (12.5%) survived in the anti-PD-1 arm, 2 of 8 animals (25%) survived in the 75 mg/kg/day Example A1 arm, 3 of 8 animals (37.5%) survived in the 150 mg/kg/day Example A1 arm, and 7 of 8 animals (87.5%) survived in the 150 mg/kg/day Example A1 and anti-PD-1 arm. These results demonstrate that compounds of the invention, as exemplified by compound A1, have in vivo antitumor activity and can be efficaciously combined with other immunomodulatory approaches.

Example F

EAE Disease Progression Model

Figure 3:
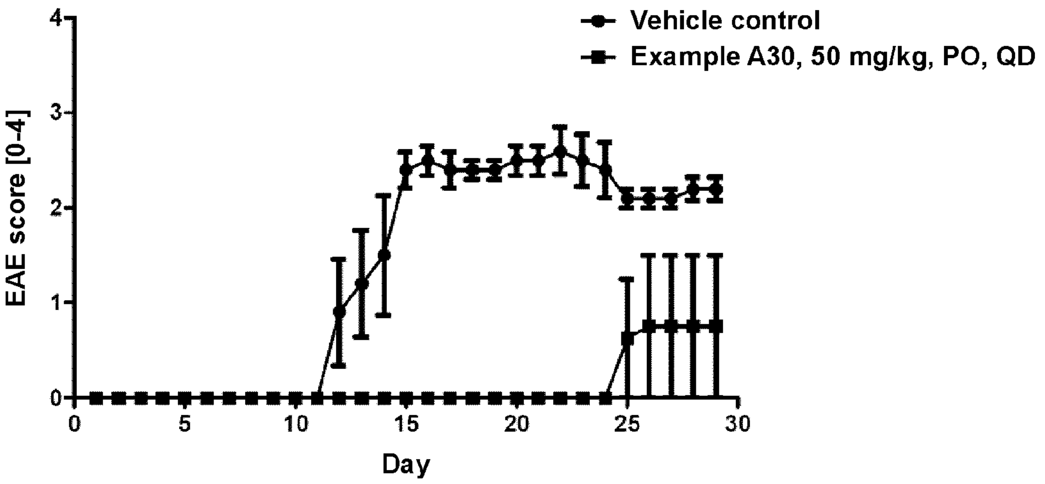
FIG. 3 shows the effect of compound example A30 in the EAE disease progression model.

C57/BL6 mice were obtained from Jackson Laboratories. The Institutional Animal Care and Use Committee of the University Health Network approved all animal procedures. Mice were subcutaneously (SC) immunized with MOG35-55 peptide emulsified in Complete Freund's Adjuvant (CFA) supplemented with *Mycobacterium tuberculosis*. On days 0 and 2 after immunization, the mice were intraperitoneal (IP) injected with pertussis toxin. Clinical signs of EAE were monitored daily, according to the following criteria: 0, no disease; 1, decreased tail tone; 2, hind limb weakness or partial paralysis; 3, complete hind limb paralysis; 4, front and hind limb paralysis; 5, death, or sacrifice due to moribund state. For treatment with compound during EAE induction, mice were dosed orally (PO) with 50 mg/kg A30 (n=4) or water (vehicle control; n=5) every day (QD). Data are the mean score±SEM. The test results is shown in FIG. 3.

What is claimed is:
1. A compound or a pharmaceutically acceptable salt thereof, wherein the compound is
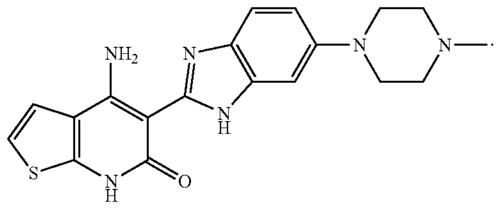 [SMILES: CN1CCN(c2ccc3nc(-c4c(N)c5ccsc5[nH]c4=O)[nH]c3c2)CC1]
2. A pharmaceutical composition comprising a compound of claim 1 and a pharmaceutically acceptable carrier or diluent.
* * * * *